(12) United States Patent
Jung et al.

(10) Patent No.: US 9,842,995 B2
(45) Date of Patent: Dec. 12, 2017

(54) AMINE-BASED COMPOUNDS AND ORGANIC LIGHT-EMITTING DEVICES COMPRISING THE SAME

(71) Applicant: SAMSUNG DISPLAY CO., LTD., Yongin, Gyeonggi-Do (KR)

(72) Inventors: Hyejin Jung, Yongin (KR); Seokhwan Hwang, Yongin (KR); Youngkook Kim, Yongin (KR); Jongwoo Kim, Yongin (KR); Jino Lim, Yongin (KR); Hyungseok Jang, Yongin (KR)

(73) Assignee: Samsung Display Co., Ltd., Yongin, Gyeonggi-do (KR)

(*) Notice: Subject to any disclaimer, the term of this patent is extended or adjusted under 35 U.S.C. 154(b) by 244 days.

(21) Appl. No.: 14/706,083

(22) Filed: May 7, 2015

(65) Prior Publication Data

US 2016/0149141 A1 May 26, 2016

(30) Foreign Application Priority Data

Nov. 21, 2014 (KR) ........................ 10-2014-0163822

(51) Int. Cl.
*H01L 51/00* (2006.01)
*C07D 405/12* (2006.01)
(Continued)

(52) U.S. Cl.
CPC ........ *H01L 51/0061* (2013.01); *C07D 405/12* (2013.01); *C07D 405/14* (2013.01); *C07D 409/14* (2013.01); *C09K 11/06* (2013.01); *H01L 51/006* (2013.01); *H01L 51/0072* (2013.01); *H01L 51/0073* (2013.01); *C07C 211/54* (2013.01); *H01L 51/0054* (2013.01); *H01L 51/0058* (2013.01); *H01L 2251/308* (2013.01)

(58) Field of Classification Search
CPC ................ C07C 211/54; C07D 405/02; C07D 405/10–405/12

See application file for complete search history.

(56) References Cited

U.S. PATENT DOCUMENTS

2005/0221124 A1* 10/2005 Hwang ................ C07F 9/5728
428/690
2009/0004485 A1 1/2009 Zheng et al.
(Continued)

FOREIGN PATENT DOCUMENTS

KR 10-2005-0097670 10/2005
KR 10-2012-0066076 6/2012
(Continued)

*Primary Examiner* — Mike M Dollinger
*Assistant Examiner* — Christina Wales
(74) *Attorney, Agent, or Firm* — Lee & Morse, P.C.

(57) ABSTRACT

An amine-based compound is represented by Formula 1:

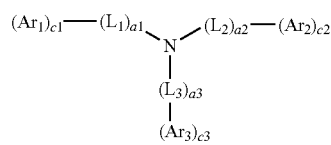

wherein $L_1$ to $L_3$, $Ar_1$ to $Ar_3$, a1 to a3, and c1 to c3 are as defined in the specification. An organic light-emitting device includes the amine-based compound.

20 Claims, 4 Drawing Sheets

(51) Int. Cl.
*C07D 405/14* (2006.01)
*C07D 409/14* (2006.01)
*C09K 11/06* (2006.01)
*C07C 211/54* (2006.01)

(56) References Cited

U.S. PATENT DOCUMENTS

2012/0248426 A1* 10/2012 Kato ............... C07D 209/86
 257/40
2013/0306958 A1 11/2013 Ito et al.
2017/0092869 A1* 3/2017 Mun ............... H01L 51/0061

FOREIGN PATENT DOCUMENTS

| KR | 10-2014-0032948 | 3/2014 |
| WO | WO-2012/157474 A1 | 11/2012 |

* cited by examiner

| 190 |
|-----|
| 150 |
| 110 |

| 190 |
|-----|
| 150 |
| 110 |
| 210 |

| 220 |
|-----|
| 190 |
| 150 |
| 110 |

| 220 |
|---|
| 190 |
| 150 |
| 110 |
| 210 |

AMINE-BASED COMPOUNDS AND ORGANIC LIGHT-EMITTING DEVICES COMPRISING THE SAME

CROSS-REFERENCE TO RELATED APPLICATION

Korean Patent Application No. 10-2014-0163822, filed on Nov. 21, 2014, in the Korean Intellectual Property Office, and entitled: "Amine-Based Compounds and Organic Light-Emitting Devices Comprising The Same," is incorporated by reference herein in its entirety.

BACKGROUND

1. Field

Embodiments relate to an amine-based compound, and an organic light-emitting device including the same.

2. Description of the Related Art

Organic light-emitting devices (OLEDs), which are self-emitting devices, have advantages such as wide viewing angles, excellent contrast, quick response, high brightness, excellent driving voltage characteristics, and can provide multicolored images.

An organic light-emitting device may have a structure in which a first electrode, a hole transport region, an emission layer, an electron transport region, and a second electrode are sequentially disposed in the stated order on a substrate. Holes injected from the first electrode move to the emission layer via the hole transport region, while electrons injected from the second electrode move to the emission layer via the electron transport region. Carriers such as holes and electrons recombine in the emission layer to generate excitons. When the excitons drop from an excited state to a ground state, light is emitted.

SUMMARY

Embodiments are directed to an amine-based compound represented by Formula 1:

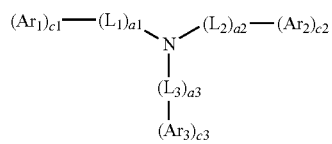

Formula 1 wherein, in Formula 1, $L_1$ to $L_3$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a3 are each independently an integer selected from 0 to 3, wherein at least two $L_1$s are the same or different when a1 is 2 or greater, at least two $L_2$s are the same or different when a2 is 2 or greater, and at least two $L_3$s are the same or different when a3 is 2 or greater;

$Ar_1$ is a group represented by Formula 2;

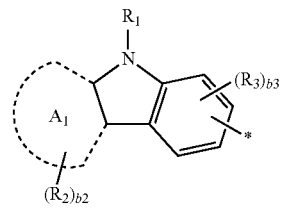

Formula 2

$Ar_2$ is a group represented by Formula 3A or a group represented by Formula 3B;

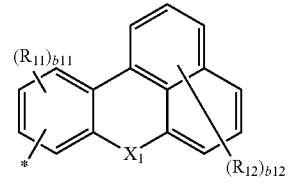

Formula 3A

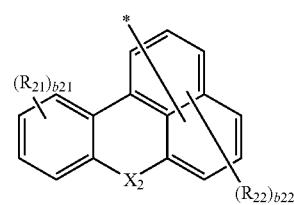

Formula 3B $Ar_3$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and c1 to c3 are each independently an integer selected from 1 to 3, wherein at least two $Ar_1$s are the same or different when c1 is 2 or greater, at least two $Ar_2$s are the same or different when c2 is 2 or greater, and at least two $Ar_3$s are the same or different when c3 is 2 or greater, and in Formulae 2, 3A, and 3B, $A_1$ is a ring selected from benzene, naphthalene, fluorene, phenanthrene and pyrene;

$R_1$ is selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$X_1$ and $X_2$ are each independently O or S;

$R_2$, $R_3$, $R_{11}$, $R_{12}$, $R_{21}$, and $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, and —$B(Q_6)(Q_7)$;

b2 and b21 are each independently an integer selected from 1 to 4, wherein at least two $R_2$s are the same or different when b2 is 2 or greater, and at least two $R_{21}$s are the same or different when b21 is 2 or greater;

b3 and b11 are each independently an integer selected from 1 to 3, wherein at least two $R_3$s are the same or different when b3 is 2 or greater, and at least two $R_{11}$s are the same or different when b11 is 2 or greater;

b12 is an integer selected from 1 to 6, wherein at least two $R_{12}$s are the same or different when b12 is 2 or greater;

b22 is an integer selected from 1 to 5, wherein at least two $R_{22}$s are the same or different when b22 is 2 or greater;

* indicates a binding site with an adjacent atom;

at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_{60}$ alkoxy group, each substituted with at least one of a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{14})(Q_{12})$, —$Si(Q_{13})(Q_{14})(Q_{15})$, and —$B(Q_{16})(Q_{17})$, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$, and —$N(Q_{31})(Q_{32})$, —$Si(Q_{33})(Q_{34})(Q_{35})$, and —$B(Q_{36})(Q_{37})$; and $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

Embodiments are also directed to an organic light-emitting device that includes a first electrode, a second electrode opposite to the first electrode, and an organic layer between the first electrode and the second electrode and including an emission layer. The organic layer includes at least one of the amine-based compounds of Formula 1.

BRIEF DESCRIPTION OF THE DRAWINGS

Features will become apparent to those of skill in the art by describing in detail exemplary embodiments with reference to the attached drawings in which:

FIGS. 1 to 4 illustrate schematic cross-sectional views of organic light-emitting devices according to embodiments of the present disclosure.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "between" two layers, it can be the only layer between the two layers, or one or more intervening layers may also be present. Like reference numerals refer to like elements throughout.

According to an embodiment of the present disclosure, there is provided an amine-based compound represented by Formula 1:

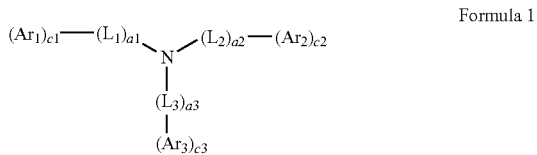

Formula 1 wherein, in Formula 1, $L_1$ to $L_3$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, $L_1$ to $L_3$ in Formula 1 may be each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

For example, according to an embodiment, $L_1$ to $L_3$ in Formula 1 may be each independently selected from:

a phenylene group, a naphthylene group, and a fluorenyl group, and a phenylene group, a naphthylene group, and a fluorenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group.

In some embodiments, $L_1$ to $L_3$ in Formula 1 may be each independently a group represented by one of Formulae 4-1 to 4-33:

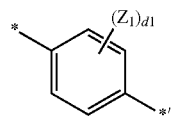

Formula 4-1

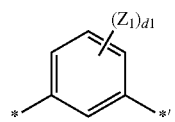

Formula 4-2

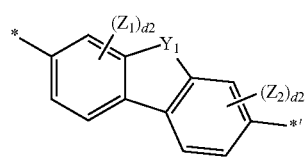

Formula 4-3

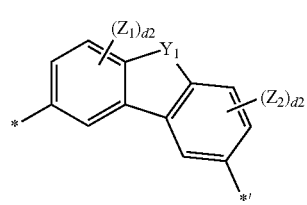

Formula 4-4

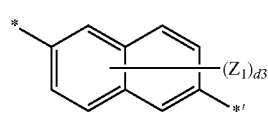

Formula 4-5

-continued

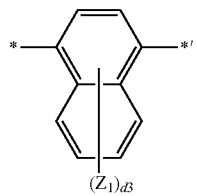

Formula 4-6

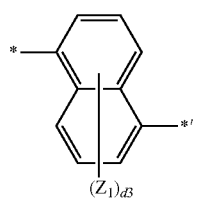

Formula 4-7

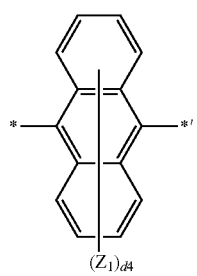

Formula 4-8

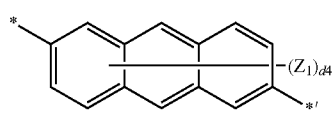

Formula 4-9

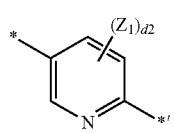

Formula 4-10

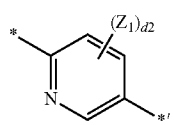

Formula 4-11

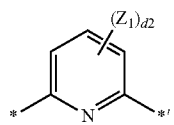

Formula 4-12

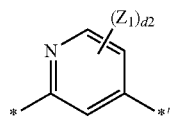

Formula 4-13

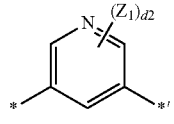

Formula 4-14

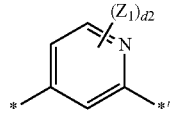

Formula 4-15

-continued

Formula 4-16 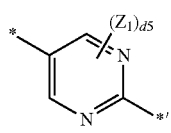

Formula 4-17 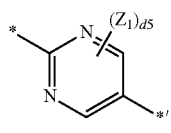

Formula 4-18 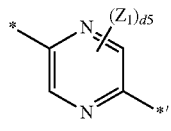

Formula 4-19 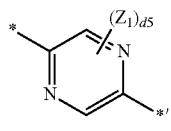

Formula 4-20 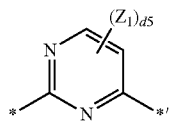

Formula 4-21 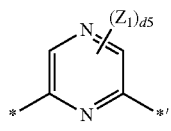

Formula 4-22 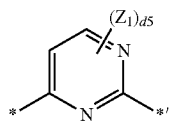

Formula 4-23 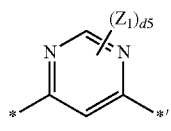

Formula 4-24 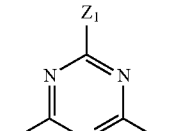

Formula 4-25 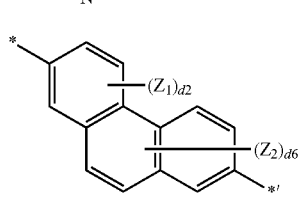

Formula 4-26 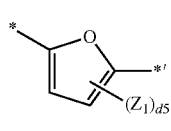

Formula 4-27 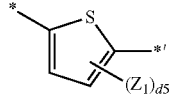

Formula 4-28 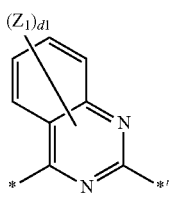

Formula 4-29 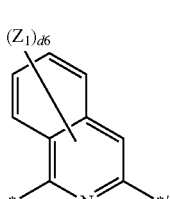

Formula 4-30 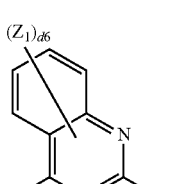

Formula 4-31 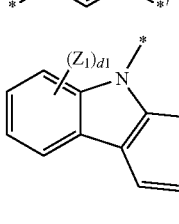

Formula 4-32 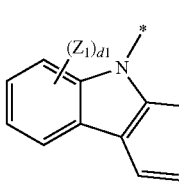

Formula 4-33 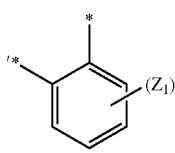

In Formulae 4-1 to 4-33, $Y_1$ may be O, S, $C(Z_3)(Z_4)$, $N(Z_5)$, or $Si(Z_6)(Z_7)$;

$Z_1$ to $Z_7$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

d1 may be an integer selected from 1 to 4;
d2 may be an integer selected from 1 to 3;
d3 may be an integer selected from 1 to 6;

d4 may be an integer selected from 1 to 8;

d5 may be 1 or 2;

d6 may be an integer selected from 1 to 5; and

* and *' may be each a binding site with an adjacent atom.

For example, $L_1$ to $L_3$ in Formula 1 may be each independently a group represented by one of Formulae 4-1 to 4-7.

In some embodiments, $L_1$ to $L_3$ in Formula 1 may be each independently a group represented by one of Formulae 5-1 to 5-27:

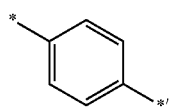

Formula 5-1

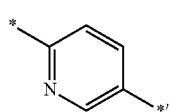

Formula 5-2

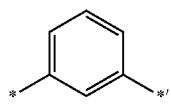

Formula 5-3

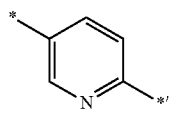

Formula 5-4

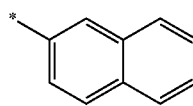

Formula 5-5

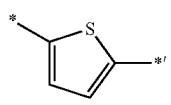

Formula 5-6

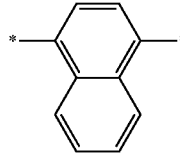

Formula 5-7

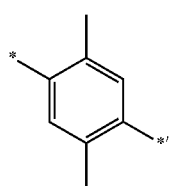

Formula 5-8

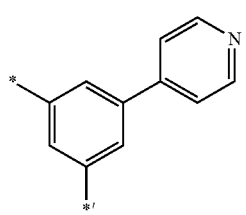

Formula 5-9

-continued

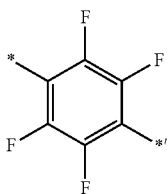

Formula 5-10

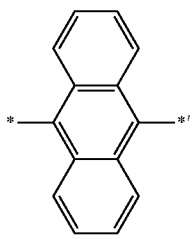

Formula 5-11

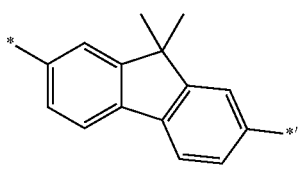

Formula 5-12

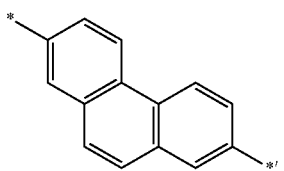

Formula 5-13

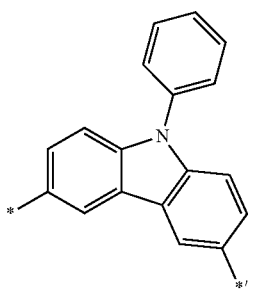

Formula 5-14

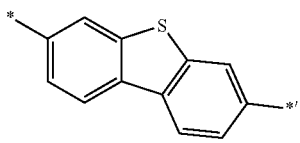

Formula 5-15

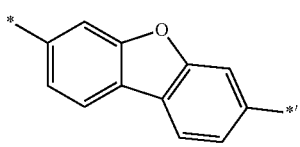

Formula 5-16

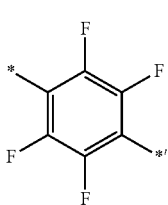

Formula 5-17

In Formulae 5-1 to 5-27, * and *' may be each a binding site with an adjacent atom.

In Formula 1, a1, a2, and a3, which indicate the numbers of $L_1$s, $L_2$s, and $L_3$s, respectively, may be each independently an integer selected from 0 to 3. At least two $L_1$s may be the same or different when a1 is 2 or greater, at least two $L_2$s may be the same or different when a2 is 2 or greater, and at least two $L_3$s may be the same or different when a3 is 2 or greater. When a1, a2, and a3 are 0, *-$(L_1)_{a1}$-*', *-$(L_2)_{a2}$-*', and *-$(L_3)_{a3}$-*', respectively, are a single bond.

For example, a1, a2, and a3 in Formula 1 may be each independently 0, 1, or 2.

In some embodiments, a1 to a3 may be all 0;

a1=1, a2=0, and a3=0;

a1=0, a2=1, and a3=0;

a1=0, a2=0, and a3=1;

a1=1, a2=1, and a3=0;

a1=1, a2=0, and a3=1;

a1=0, a2=1, and a3=1;

a1 to a3 may be all 1; or a1=2, a2=0, and a3=0.

In Formula 1, $Ar_1$ may be a group represented by Formula 2;

$Ar_2$ may be a group represented by Formula 3A or a group represented by Formula 3B;

-continued

Formula 3B

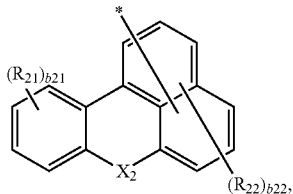

Ar₃ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In Formula 2, $A_1$ may be a ring selected from benzene, a naphthalene, fluorene, phenanthrene, and pyrene. For example, the $A_1$ ring in Formula 2 may be benzene or naphthalene.

In Formula 2, $R_1$ may be selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, $R_1$ in Formula 2 and Ar₃ in Formula 1 may be each independently selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$), wherein $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

For example, $R_1$ in Formula 1 and $Ar_3$ in Formula 1 may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, a dibenzocarbazolyl group, and —Si($Q_{33}$)($Q_{34}$)($Q_{35}$), wherein $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

In some embodiments, $R_1$ in Formula 2 may be each independently selected from:

a phenyl group, a naphthyl group, and a fluorenyl group, and a phenyl group, a naphthyl group, and a fluorenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group.

In some embodiments. $Ar_3$ in Formula 1 may be each independently selected from:

a phenyl group, a naphthyl group, a fluorenyl group, a pyridinyl group, a carbazolyl group, a dibenzofuranyl group, and a dibenzothiophenyl group, and a phenyl group, a naphthyl group, a fluorenyl group, a pyridinyl group, a carbazolyl group, a dibenzofuranyl group, and a dibenzothiophenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group.

In some embodiments, $R_1$ in Formula 2 and $Ar_3$ in Formula 1 may be each independently selected from groups represented by Formulae 6-1 to 6-17:

Formula 6-1

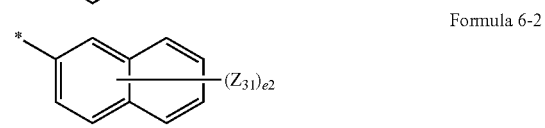

Formula 6-2

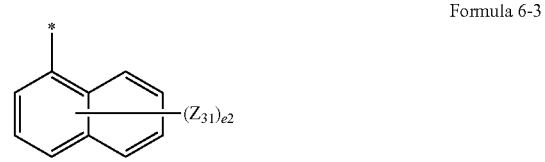

Formula 6-3

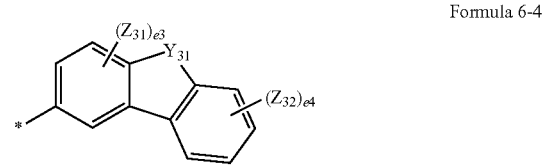

Formula 6-4

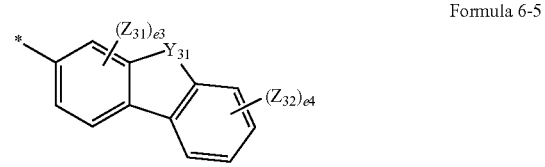

Formula 6-5

Formula 6-6

Formula 6-7

Formula 6-8

-continued

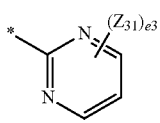
Formula 6-9

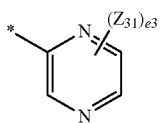
Formula 6-10

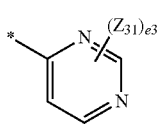
Formula 6-11

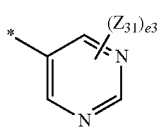
Formula 6-12

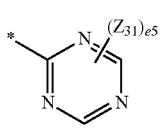
Formula 6-13

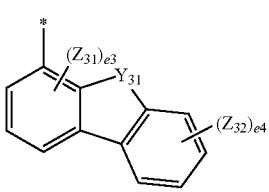
Formula 6-14

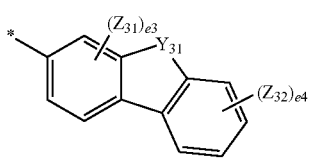
Formula 6-15

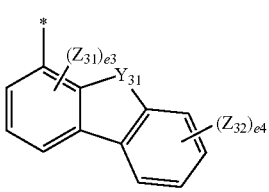
Formula 6-16

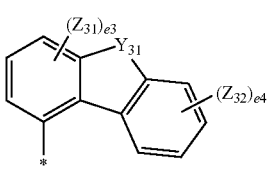
Formula 6-17

In Formulae 6-1 to 6-17, $Y_{31}$ may be O, S, $C(Z_{33})(Z_{34})$, or $N(Z_{35})$;

$Z_{31}$ to $Z_{35}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, a dibenzocarbazolyl group, and —Si$(Q_{33})(Q_{34})(Q_{35})$, wherein $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

e1 may be an integer of 1 to 5;

e2 may be an integer of 1 to 7;

e3 may be an integer of 1 to 3;

e4 may be an integer of 1 to 4;

e5 may be an integer of 1 or 2; and

\* may be a binding site with an adjacent atom.

For example, $R_1$ in Formula 2 may be a group represented by one of Formulae 6-1 to 6-5 and Formulae 6-14 to 6-17.

In some embodiments, $R_1$ in Formula 2 and $Ar_3$ in Formula 1 may be each independently selected from groups represented by Formulae 7-1 to 7-33:

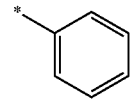
Formula 7-1

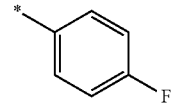
Formula 7-2

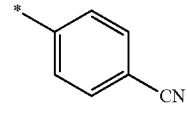
Formula 7-3

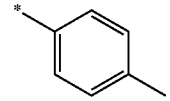
Formula 7-4

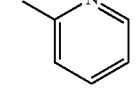
Formula 7-5

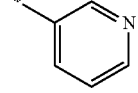
Formula 7-6

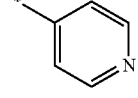
Formula 7-7

-continued
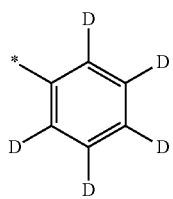
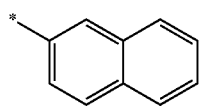
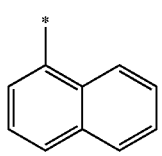
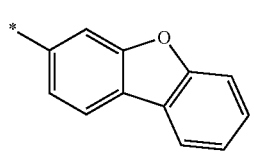
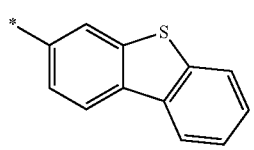
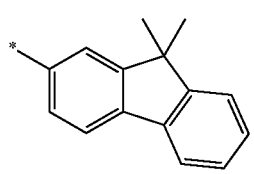
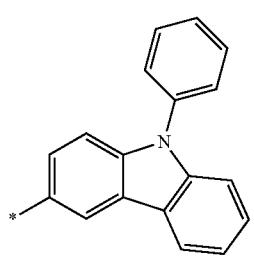
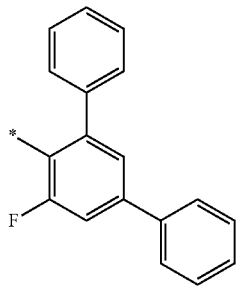
-continued
Formula 7-8
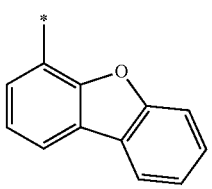
Formula 7-9
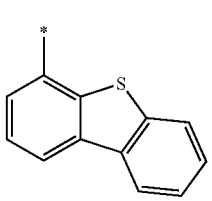
Formula 7-10
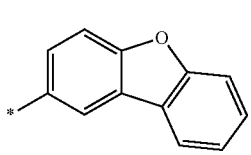
Formula 7-11
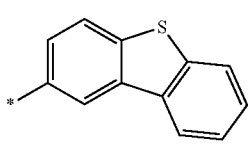
Formula 7-12
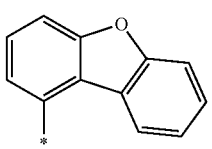
Formula 7-13
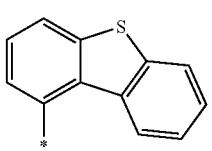
Formula 7-14
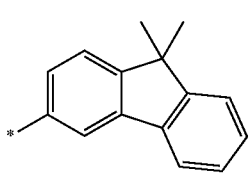
Formula 7-15
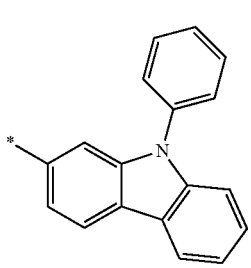
Formula 7-16
Formula 7-17
Formula 7-18
Formula 7-19
Formula 7-20
Formula 7-21
Formula 7-22
Formula 7-23
Formula 7-24
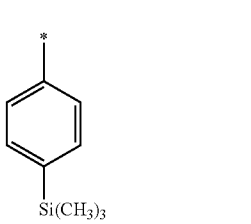

Formula 7-25
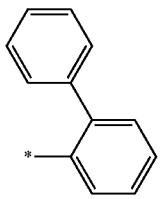

Formula 7-26
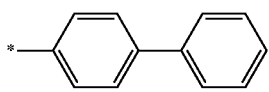

Formula 7-27
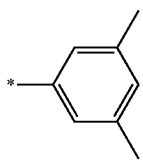

Formula 7-28
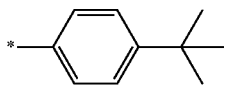

Formula 7-29
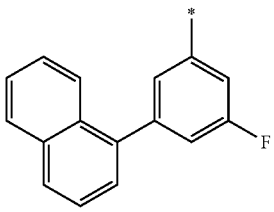

Formula 7-30
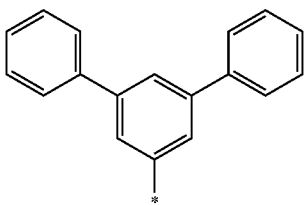

Formula 7-31
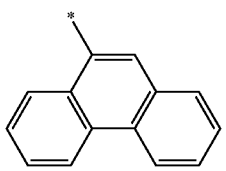

Formula 7-32
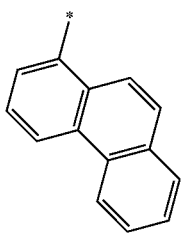

Formula 7-33
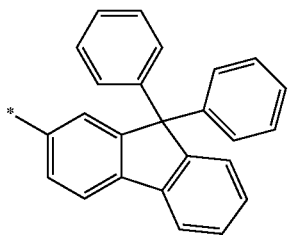

In Formulae 7-1 to 7-33, * may be a binding site with an adjacent atom.

In Formulae 3A and 3B, $X_1$ and $X_2$ may be each independently O or S.

In some embodiments, $X_1$ and $X_2$ in Formulae 3A and 3B may be O.

In Formulae 2, 3A, and 3B, $R_2$, $R_3$, $R_{11}$, $R_{12}$, $R_{21}$, and $R_{22}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, and —$B(Q_6)(Q_7)$.

In some embodiments, in Formulae 2, 3A, and 3B, $R_2$, $R_3$, $R_{11}$, $R_{12}$, $R_{21}$, and $R_{22}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —$Si(Q_3)(Q_4)(Q_5)$, wherein $Q_3$ to $Q_5$ may be each independently selected from a $C_1$-$C_{20}$ alkyl group, a $C_1$-$C_{20}$ alkoxy group, a phenyl group, and a naphthyl group.

In some embodiments, in Formulae 2, 3A, and 3B, $R_2$, $R_3$, $R_{11}$, $R_{12}$, $R_{21}$, and $R_{22}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

In some embodiments, in Formulae 2, 3A, and 3B, $R_2$, $R_3$, $R_{11}$, $R_{12}$, $R_{21}$, and $R_{22}$ may be all hydrogens.

In Formulae 2 and 3B, b2 and b21 may be are each independently an integer selected from 1 to 4, wherein at least two $R_2$s may be the same or different when b2 is 2 or greater, and at least two $R_{21}$s may be the same or different when b21 is 2 or greater.

In Formulae 2 and 3A, b3 and b11 may be each independently an integer selected from 1 to 3, wherein at least two $R_3$s may be the same or different when b3 is 2 or greater, and at least two $R_{11}$s may be the same or different when b11 is 2 or greater.

In Formula 3A, b12 may be an integer selected from 1 to 6, wherein at least two $R_{12}$s may be the same or different when b12 is 2 or greater.

In Formula 3B, b22 may be an integer selected from 1 to 5, wherein at least two $R_{22}$s may be the same or different when b22 is 2 or greater.

For example, in Formulae 2, 3A, and 3B, b2, b3, b11, b12, b21, and b22 may be each independently 1 or 2.

In Formula 1, c1 to c3 may be each independently an integer selected from 1 to 3, wherein at least two $Ar_1$s may be the same or different when c1 is 2 or greater, at least two $Ar_2$s may be the same or different when c2 is 2 or greater, and at least two $Ar_3$s may be the same or different when c3 is 2 or greater. For example, in Formula 1, c1 and c2 may be 1, and c3 may be 1, 2, or 3.

In some embodiments, in according to an embodiment, $Ar_1$ in Formula 1 may be a group represented by one of Formulae 2-1 to 2-6:

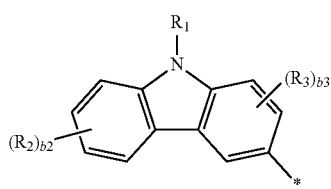

Formula 2-1

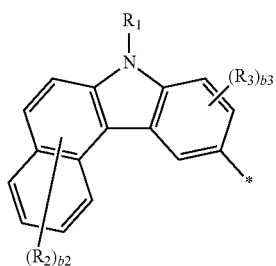

Formula 2-2

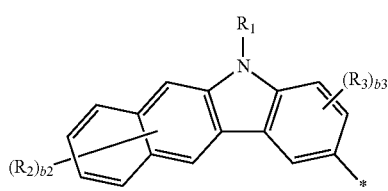

Formula 2-3

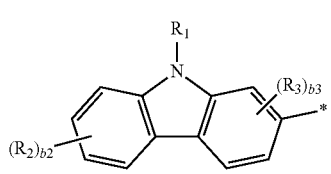

Formula 2-4

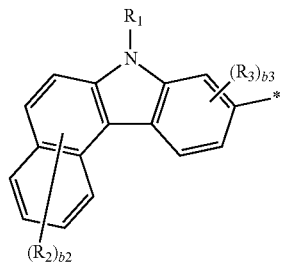

Formula 2-5

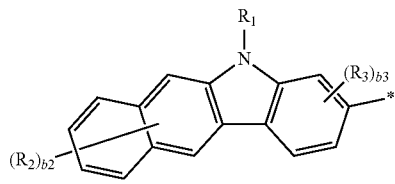

Formula 2-6

In Formulae 2-1 to 2-6, $R_1$ to $R_3$, b2, b3, and * may have the same definitions as described above.

For example, in Formulae 2-1 to 2-6, $R_1$ may be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and —Si($Q_{33}$)($Q_{34}$)($Q_{35}$), wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_2$ and $R_3$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

b2 and b3 may be each independently 1 or 2; and

* may be a binding site with an adjacent atom.

In some embodiments, $Ar_1$ in Formula 1 may be selected from groups represented by Formula 8-1 to 8-21:
Formula 8-1
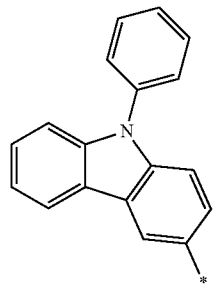
Formula 8-2
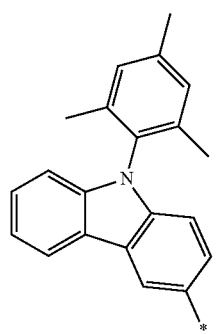
Formula 8-3
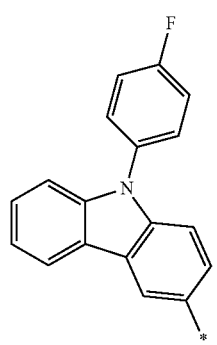
Formula 8-4
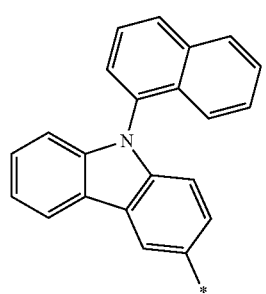
-continued
Formula 8-5
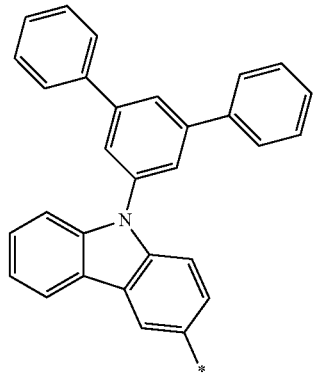
Formula 8-6
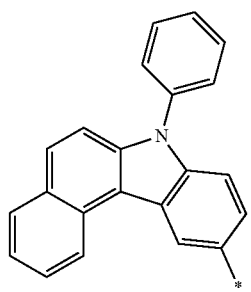
Formula 8-7
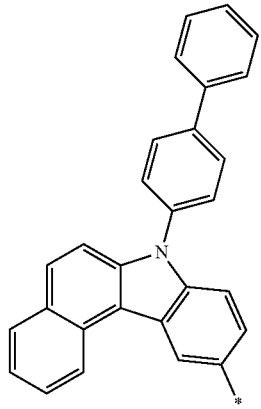
Formula 8-8
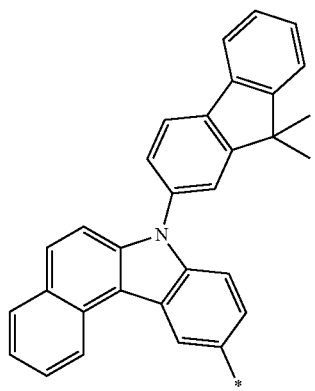

Formula 8-9
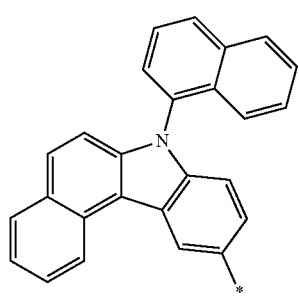
Formula 8-10
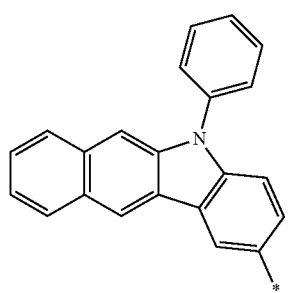
Formula 8-11
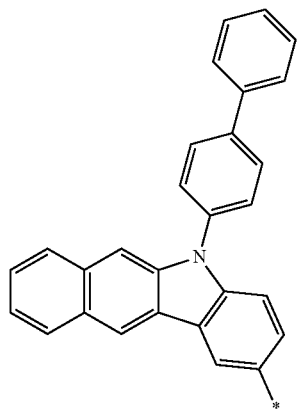
Formula 8-12
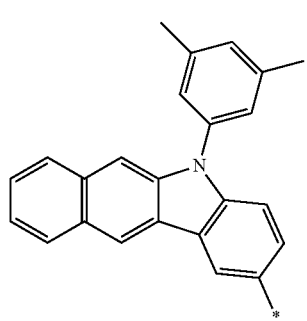
Formula 8-13
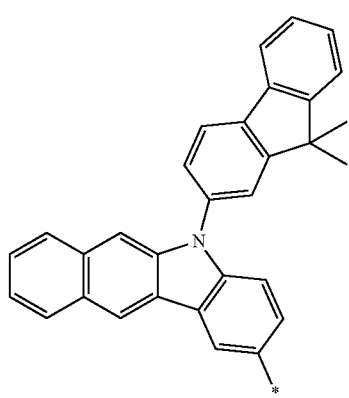
Formula 8-14
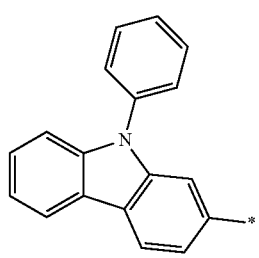
Formula 8-15
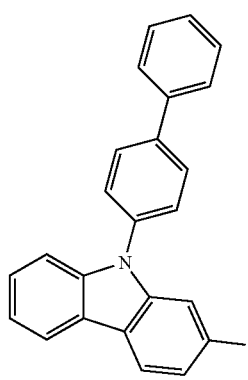
Formula 8-16
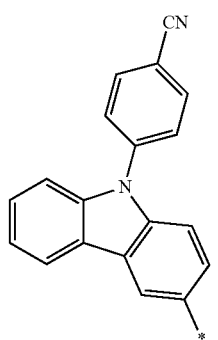
Formula 8-17
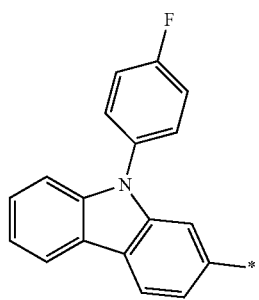

-continued

Formula 8-18
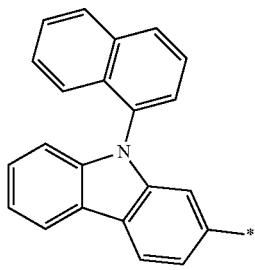

Formula 8-19
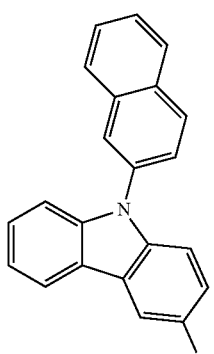

Formula 8-20
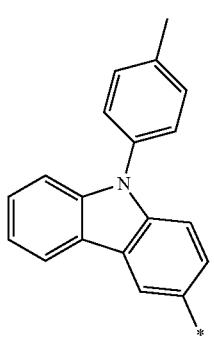

Formula 8-21
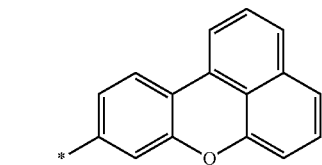

In Formulae 8-1 to 8-21, * may be a binding site with an adjacent atom.

In some embodiments, $Ar_2$ in Formula 1 may be a group represented by one of Formulas 3A-1, 3B-1, 3A-2, and 3B-2:

Formula 3A-1
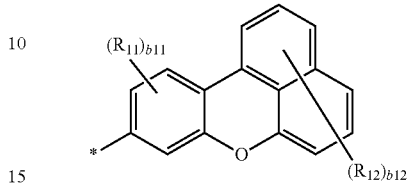

Formula 3B-1
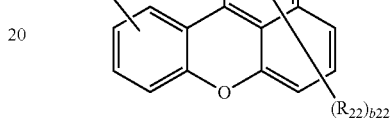

Formula 3A-2
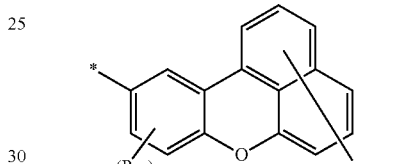

Formula 3B-2
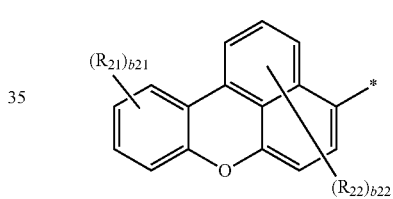

In Formula 3A-1, 3B-1, 3A-2, and 3B-2, $R_{11}$, $R_{12}$, $R_{21}$, $R_{22}$, b11, b12, b21, b22 and * may have the same definitions as described above.

For example, in Formulae 3A-1, 3B-1, 3A-2, and 3B-2, $R_{11}$, $R_{12}$, $R_{21}$, and $R_{22}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

b21 and b22 may be each independently 1 or 2; and

* may be a binding site with an adjacent atom.

In some embodiments, $Ar_2$ in Formula 1 may be selected from a group represented by Formula 9-1 and a group represented by Formula 9-2:

Formula 9-1

-continued

Formula 9-2

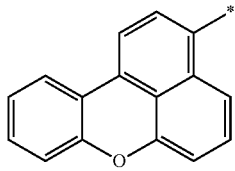

In Formulae 9-1 and 9-2, * may be a binding site with an adjacent atom.

In some embodiments, in the amine-based compound of Formula 1, $L_1$ to $L_3$ may be each independently a group represented by one of Formulae 5-1 to 5-27;

a1 to a3 may be each independently 0, 1, or 2;

$Ar_1$ may be a group represented by one of Formulae 2-1 to 2-6;

$Ar_2$ may be a group represented by one of Formulae 3A-1, 3B-1, 3A-2, and 3B-2; and $Ar_3$ may be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, a dibenzocarbazolyl group, and —Si($Q_{33}$)($Q_{34}$)($Q_{35}$), wherein $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

For example, the amine-based compound of Formula 1 may be one of Compounds 1 to 110:

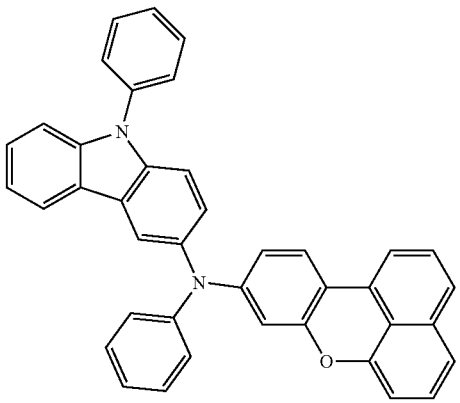

1

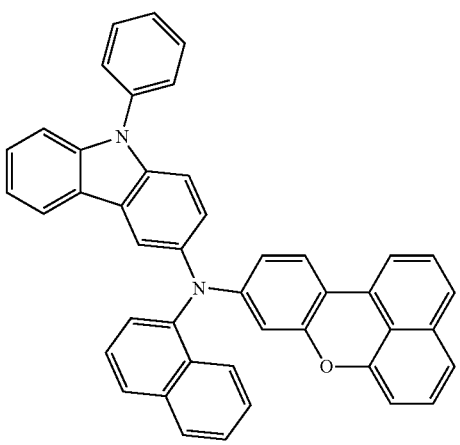

2

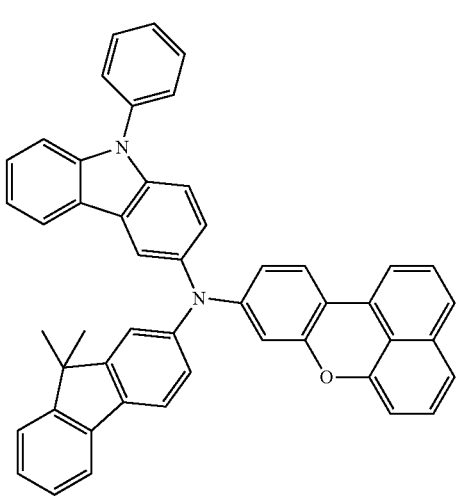

3

4
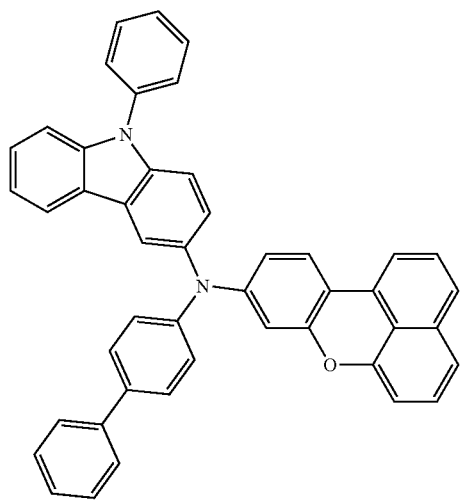
5
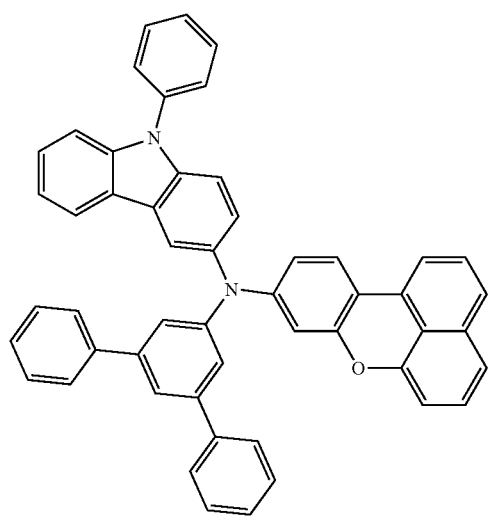
6
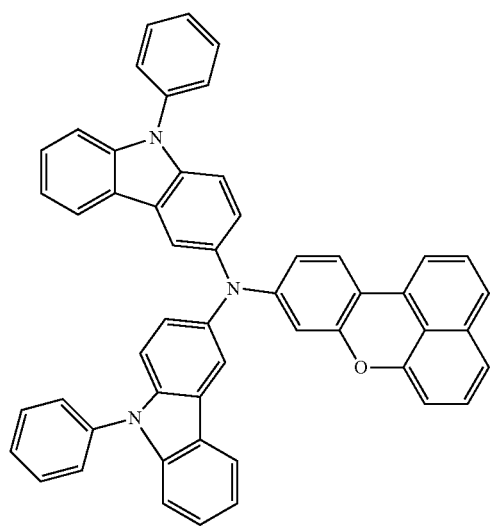
7
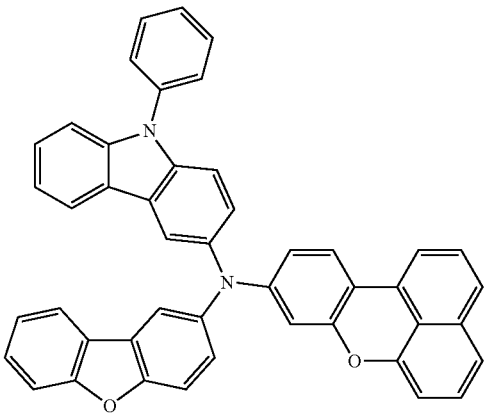
8
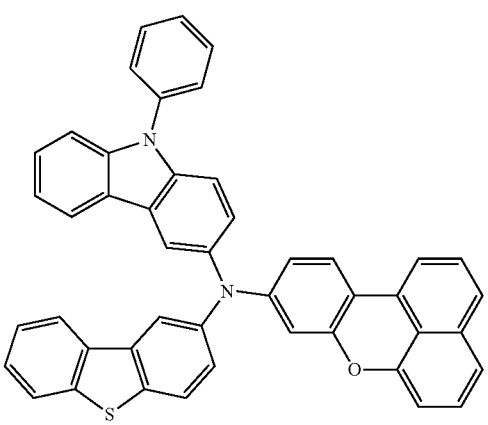
9
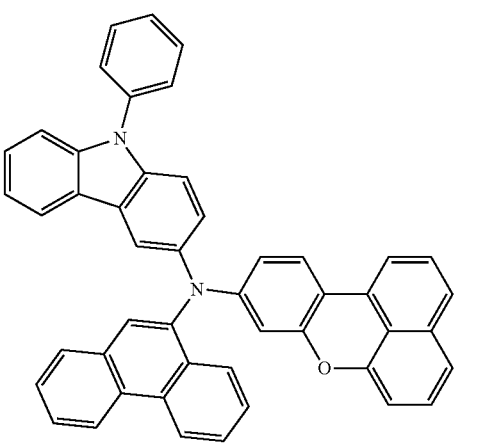

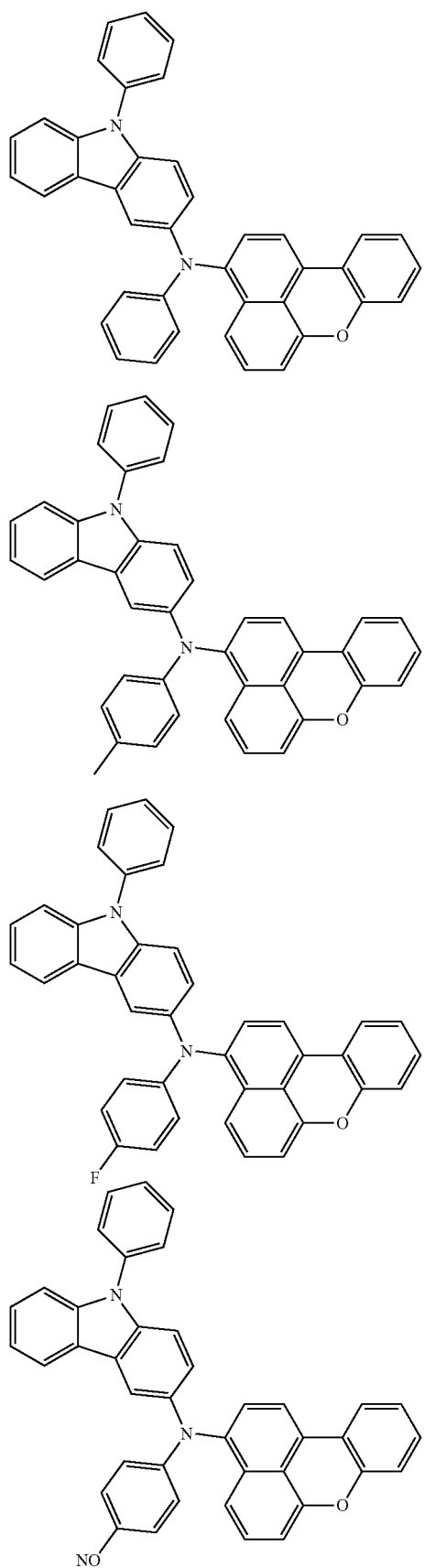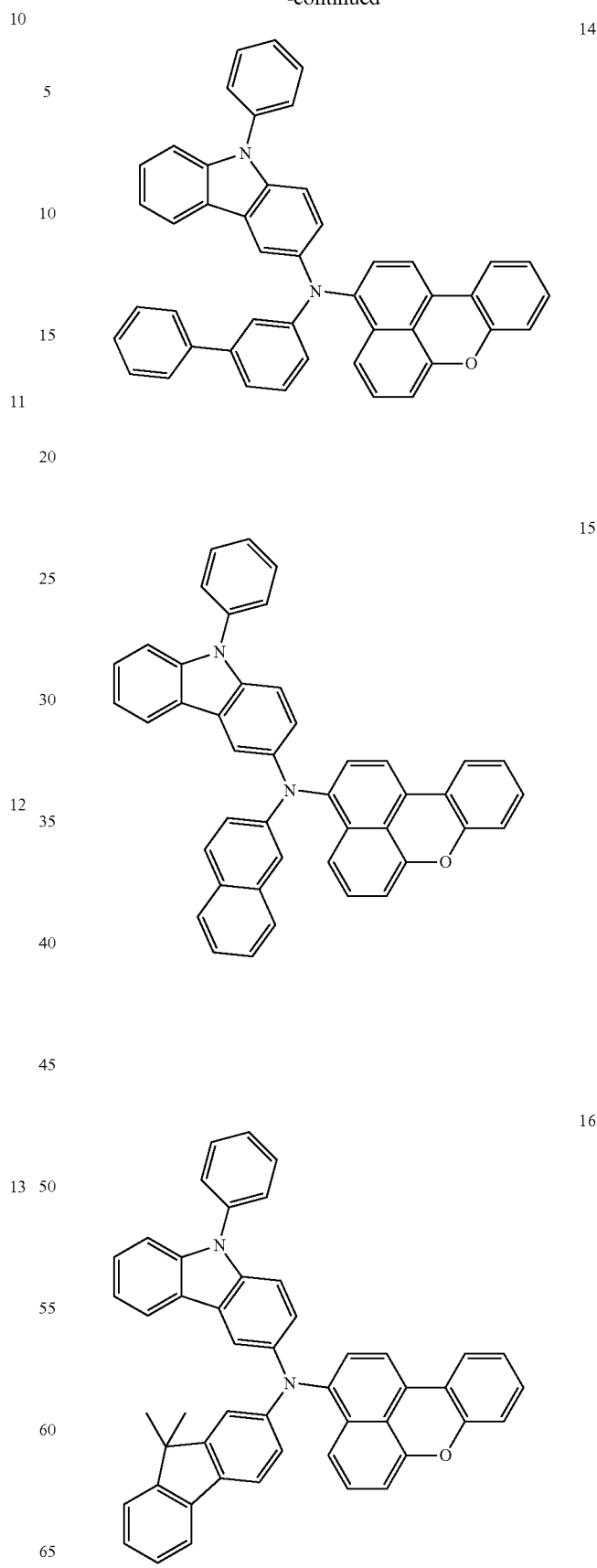

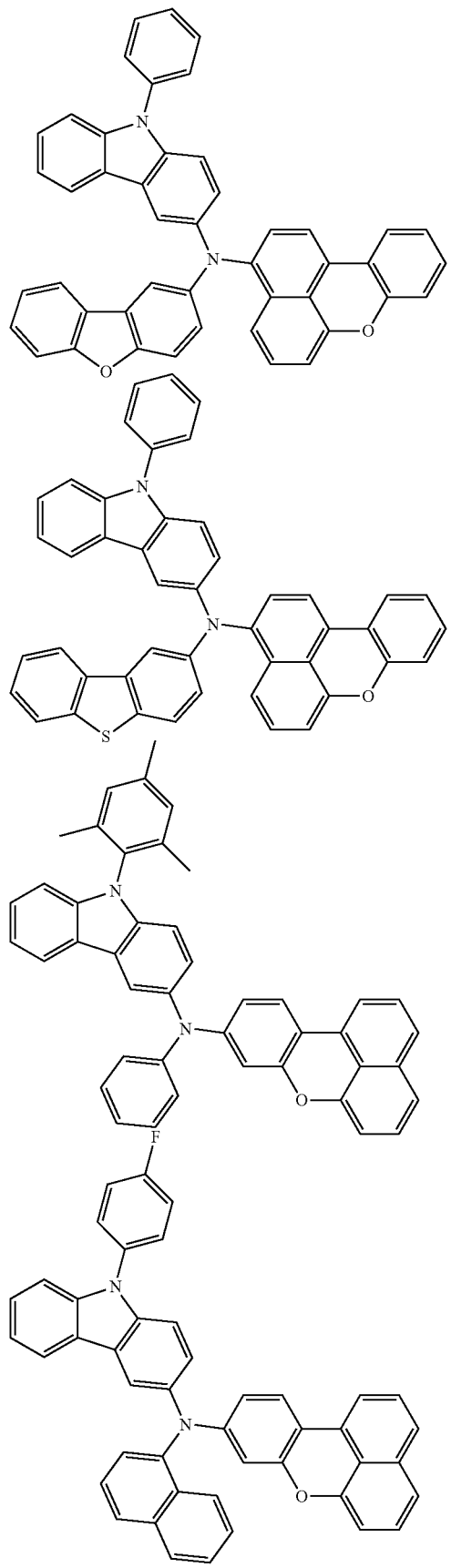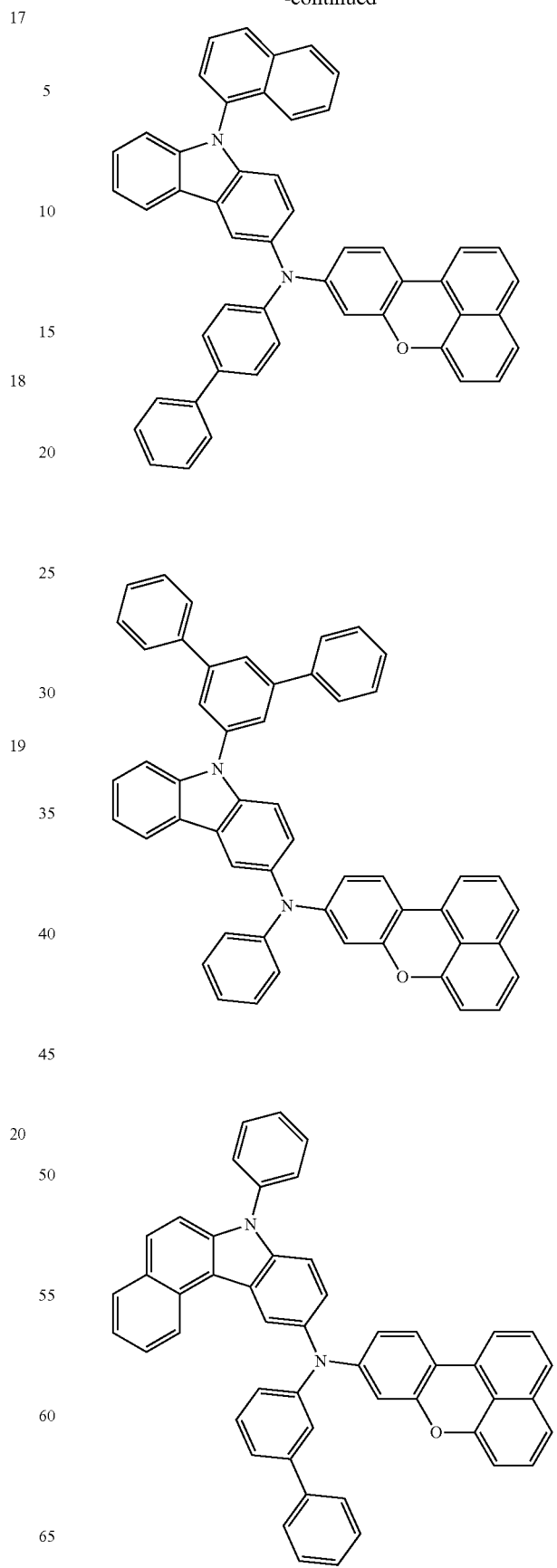

24
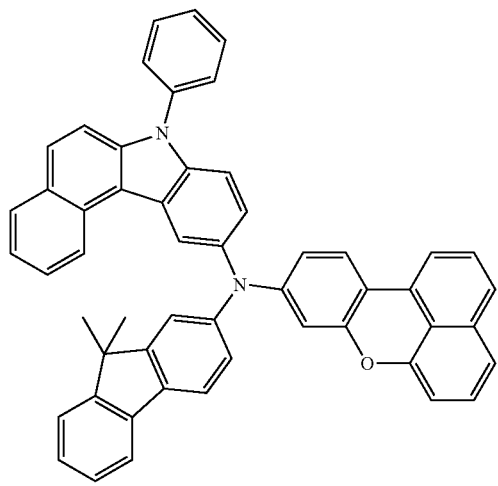
25
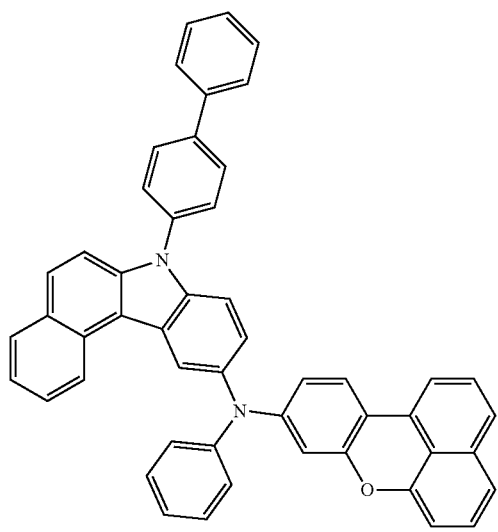
26
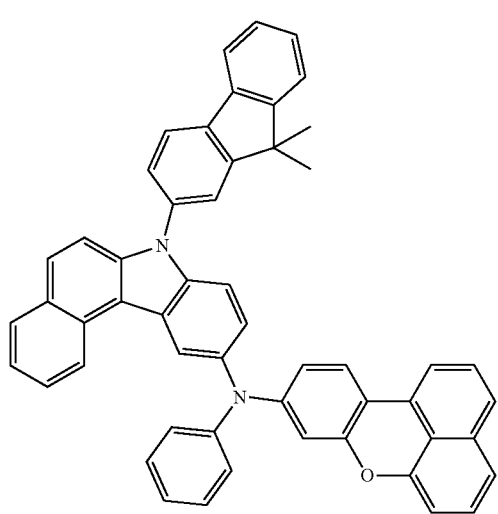
27
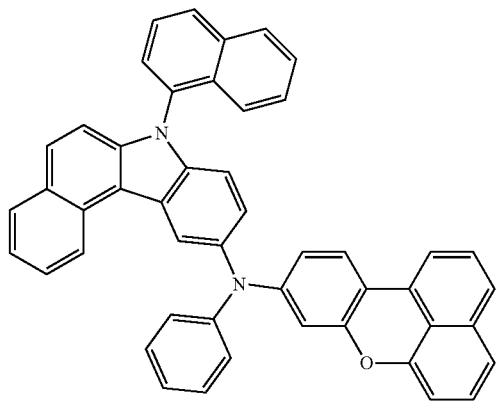
28
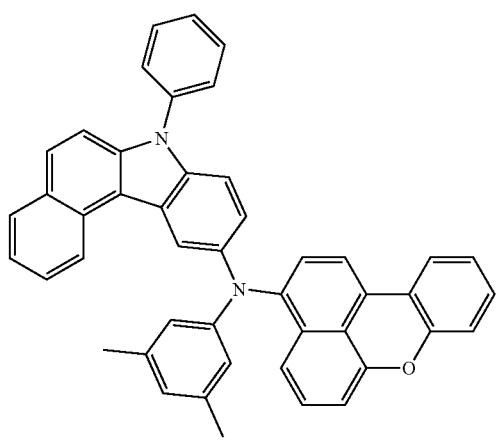
29
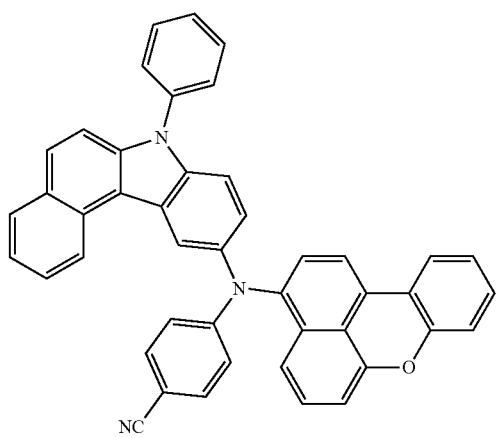

30
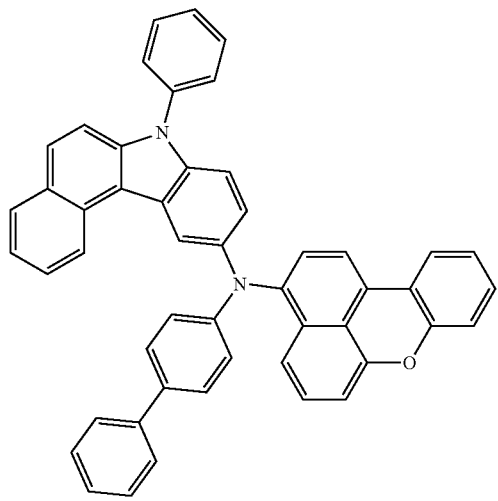
31
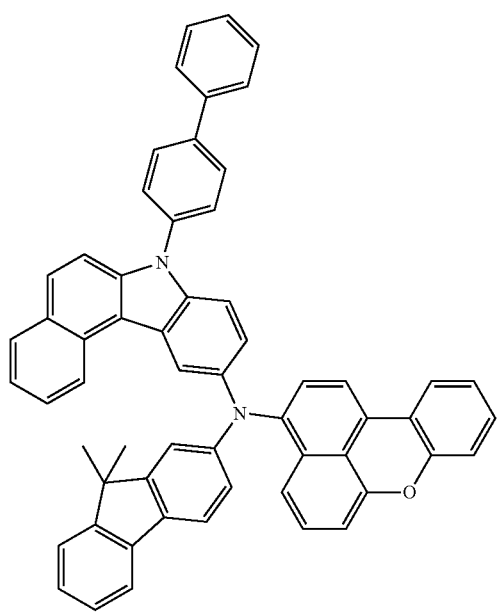
32
33
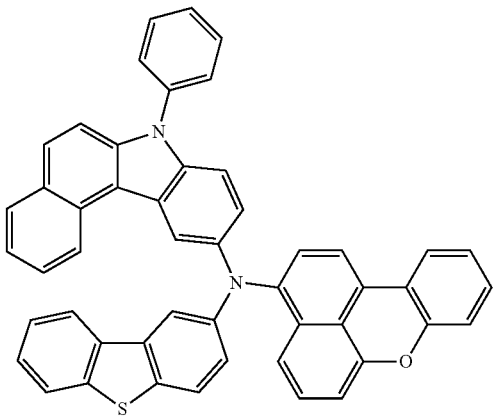
34
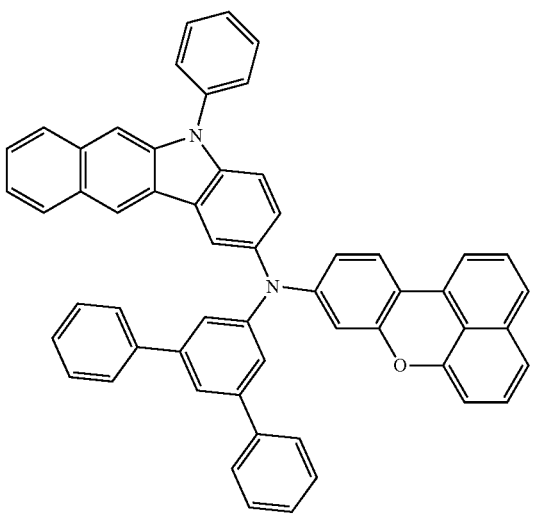
35
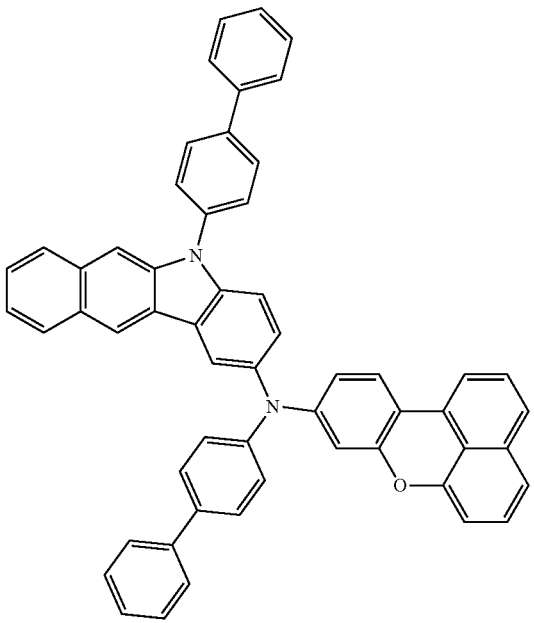
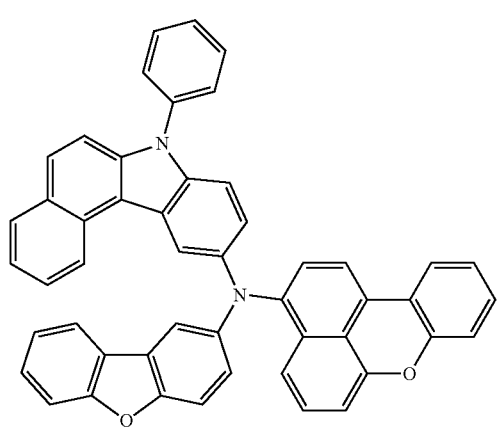

36
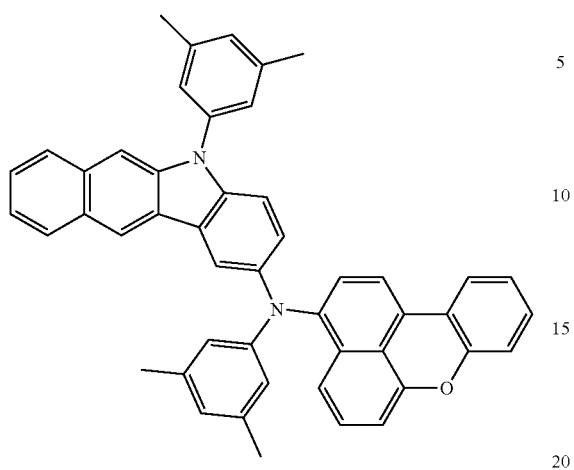
37
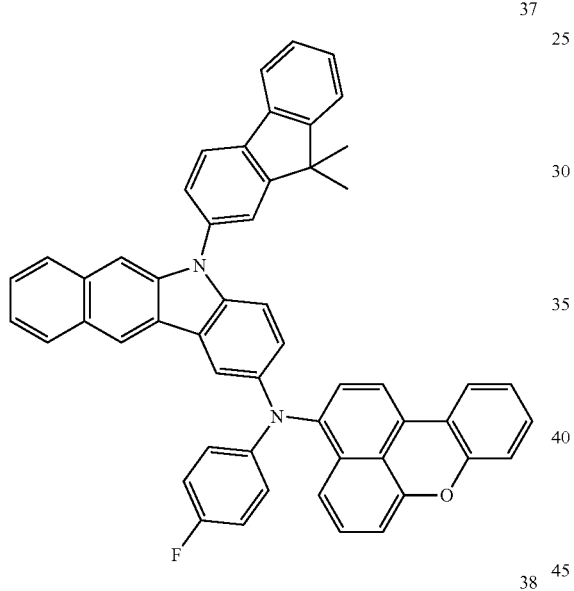
38
39
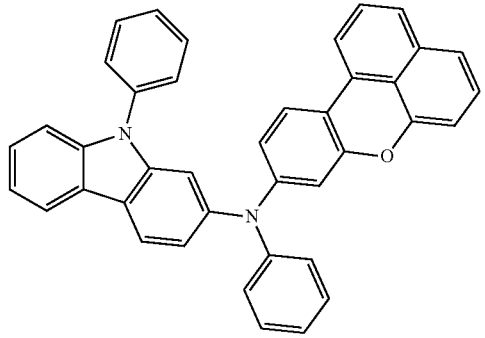
40
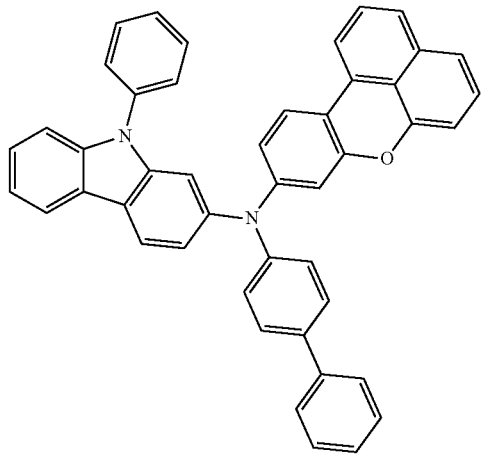
41
42
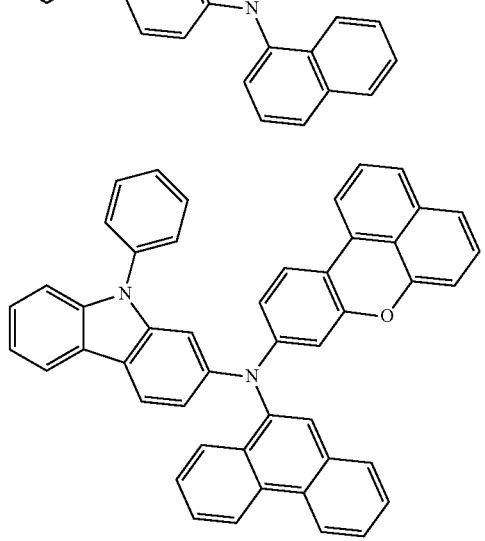

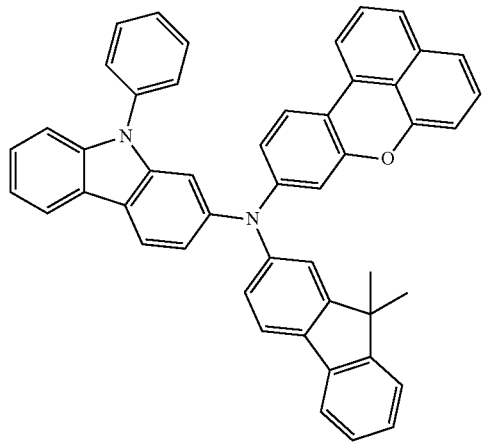
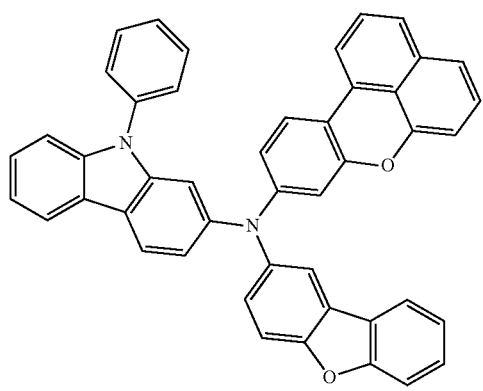
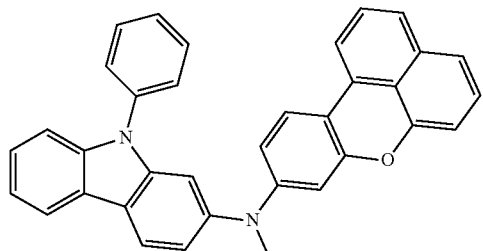
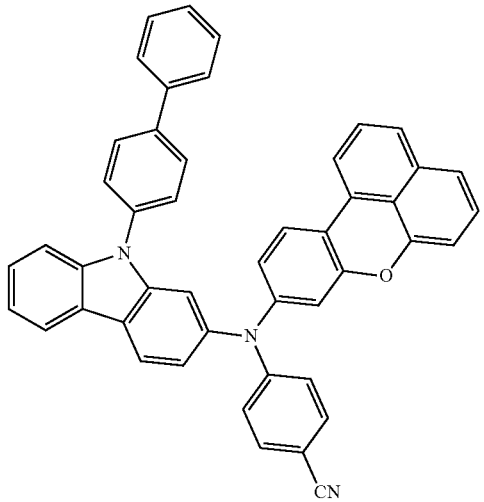
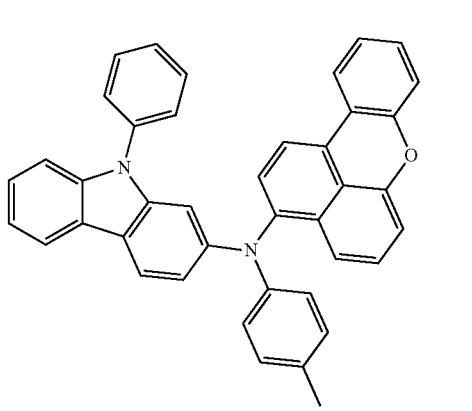
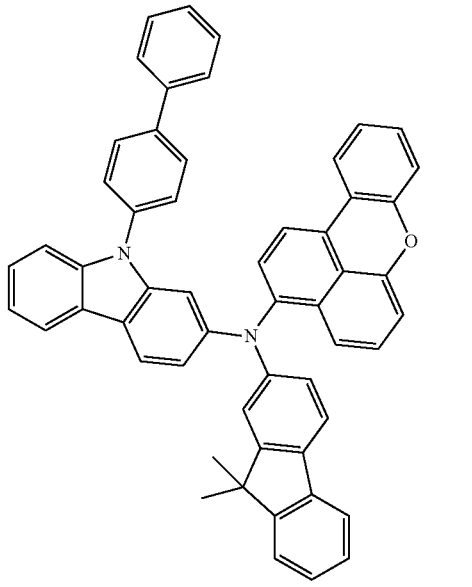

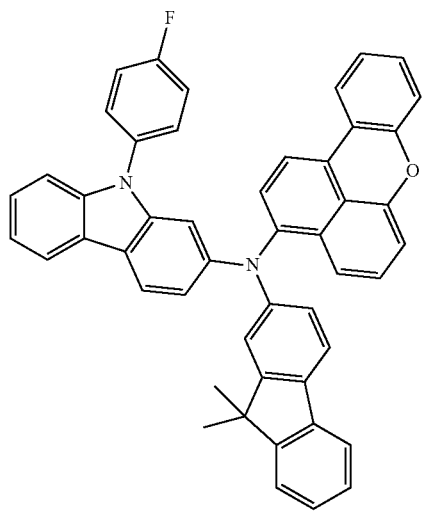
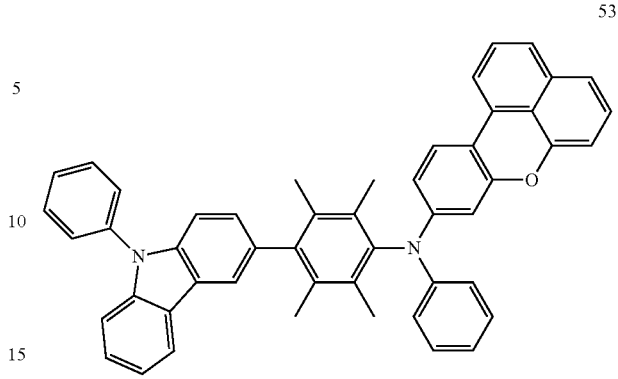
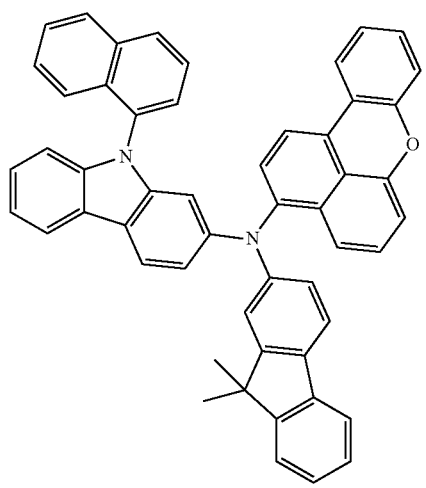
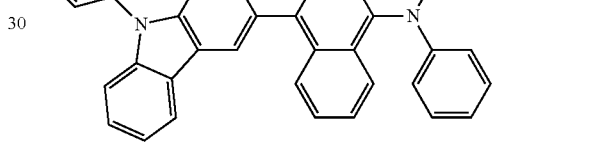
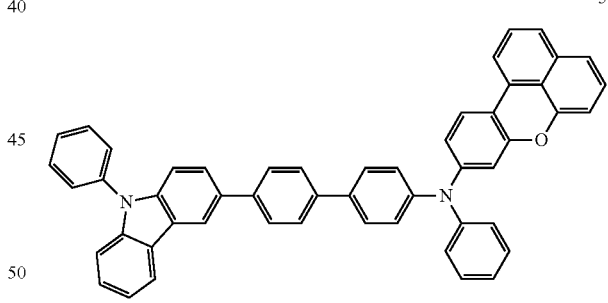
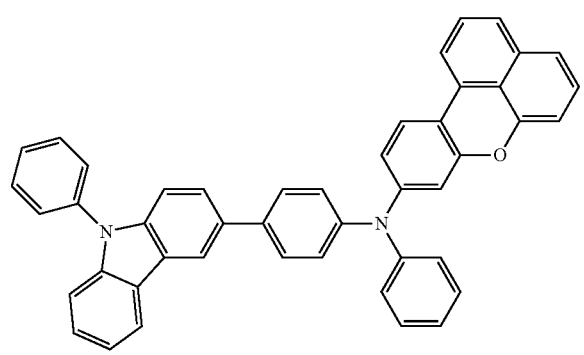
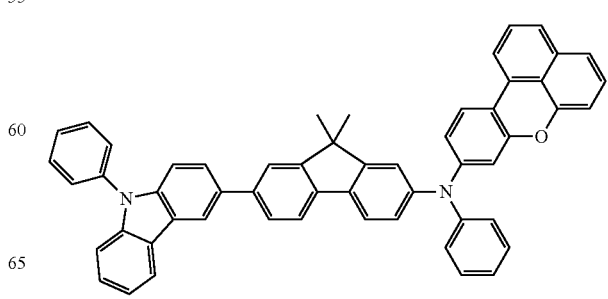

57
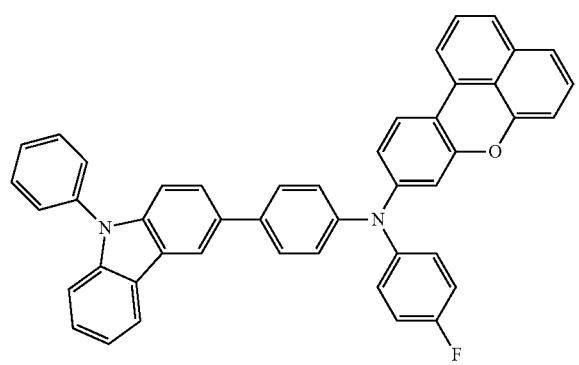
58
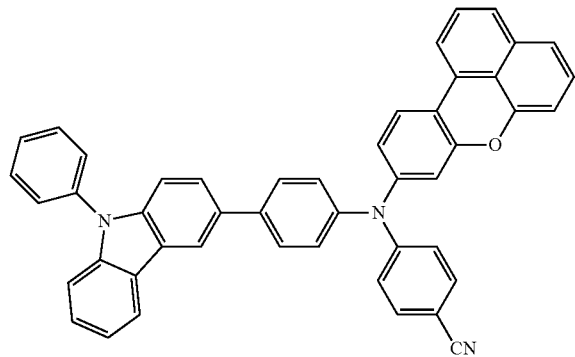
59
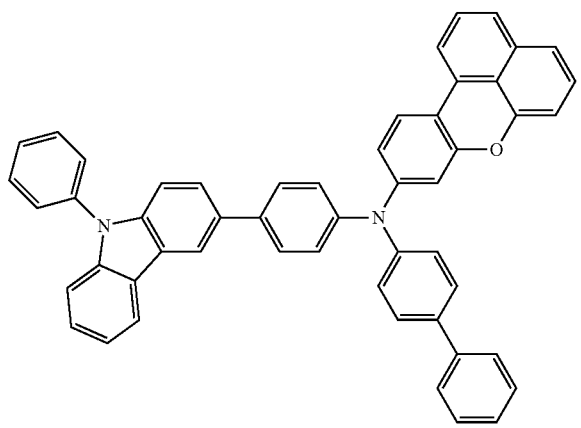
60
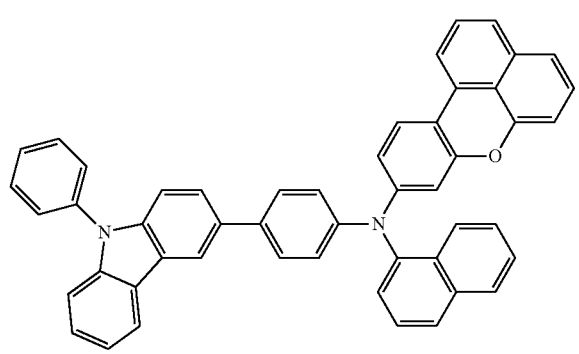
61
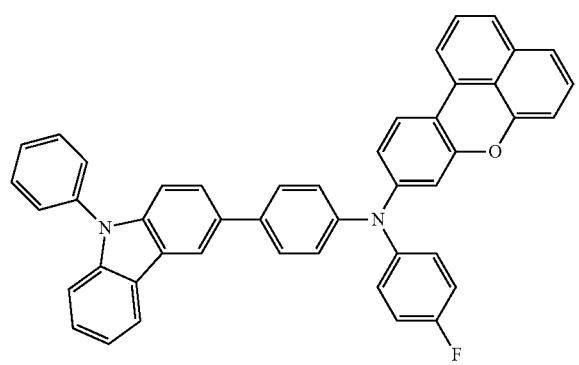
62
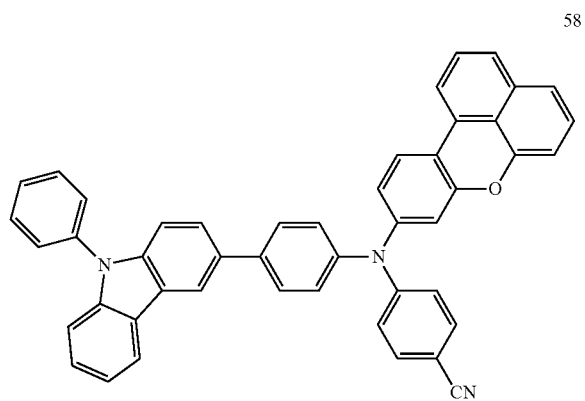
63
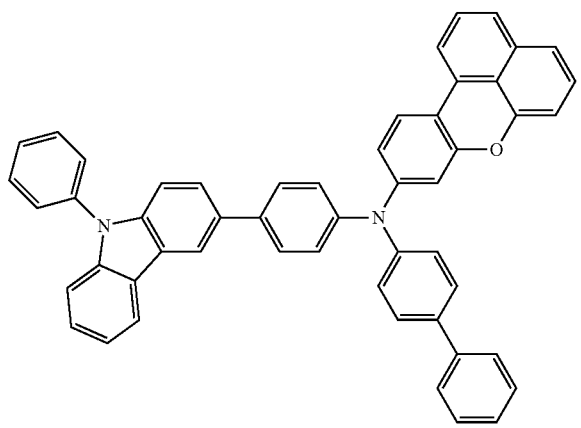
64
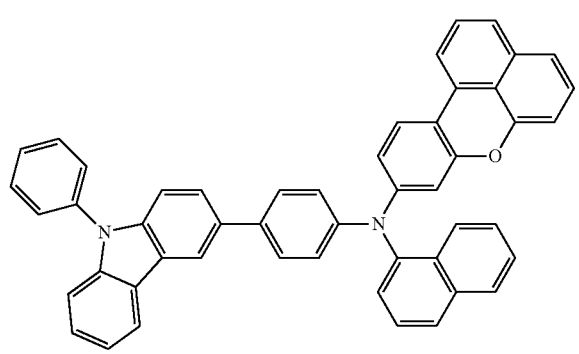

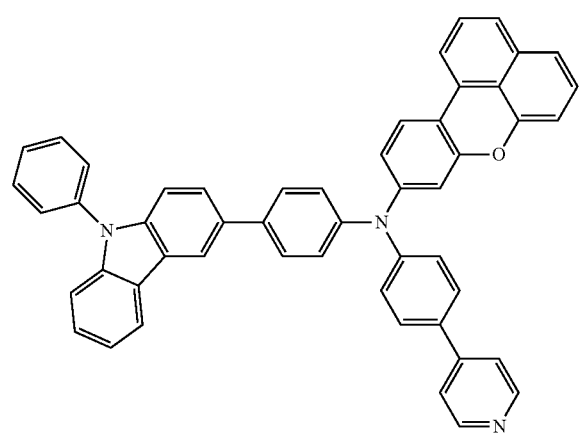
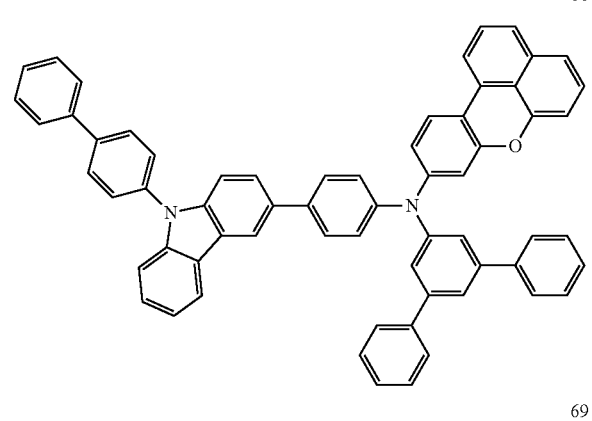
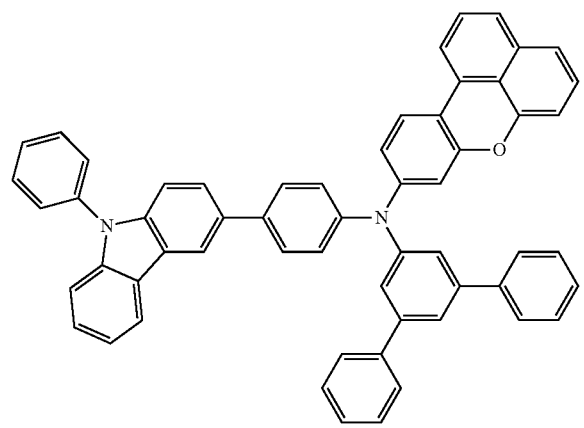
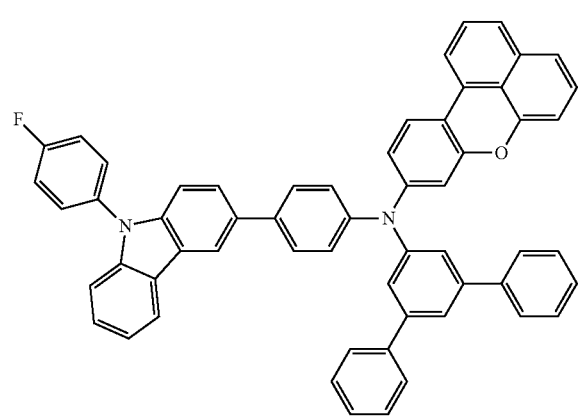

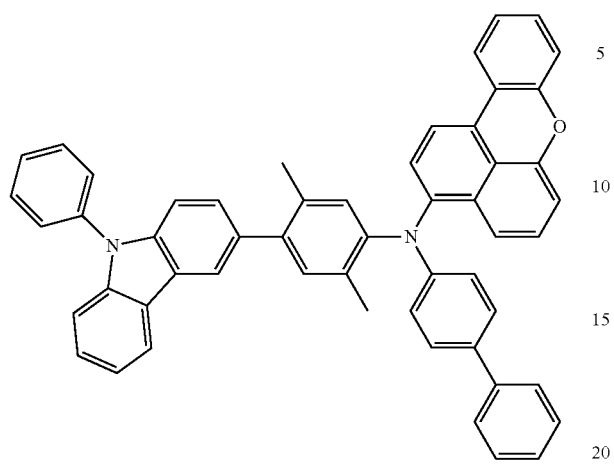
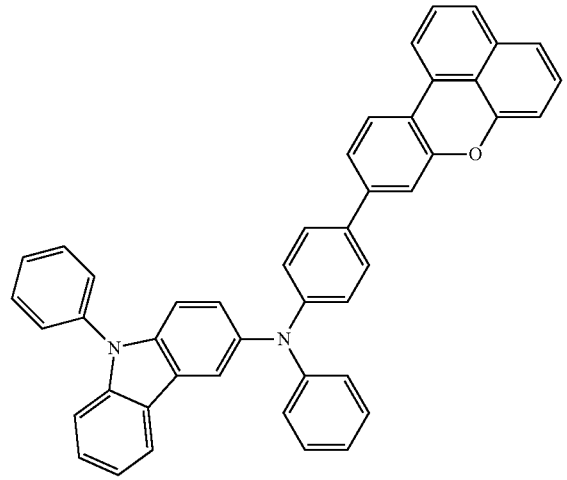
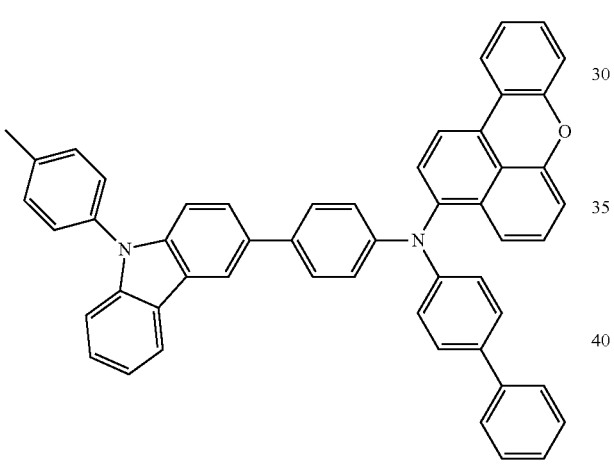
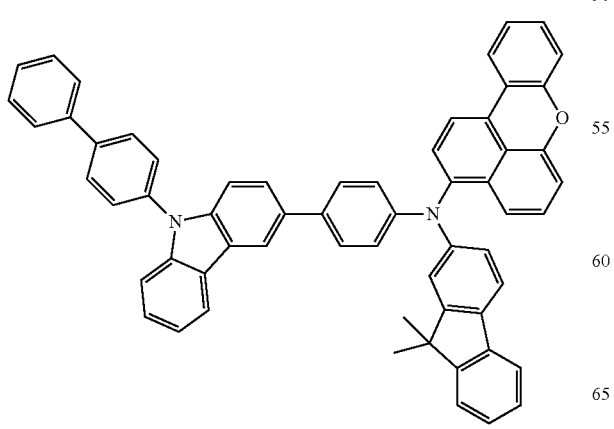
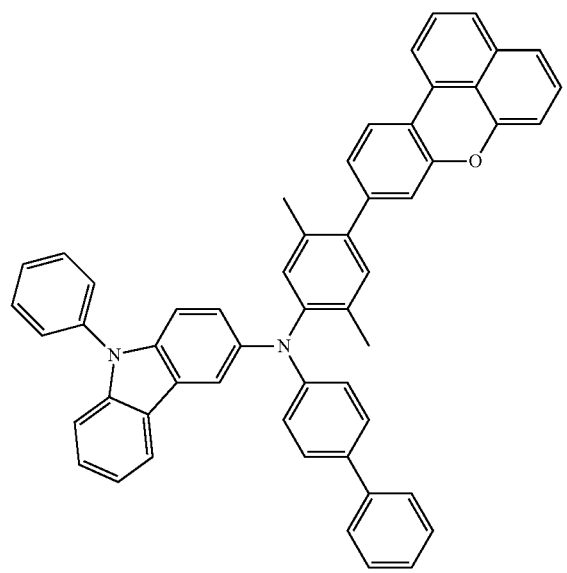

78
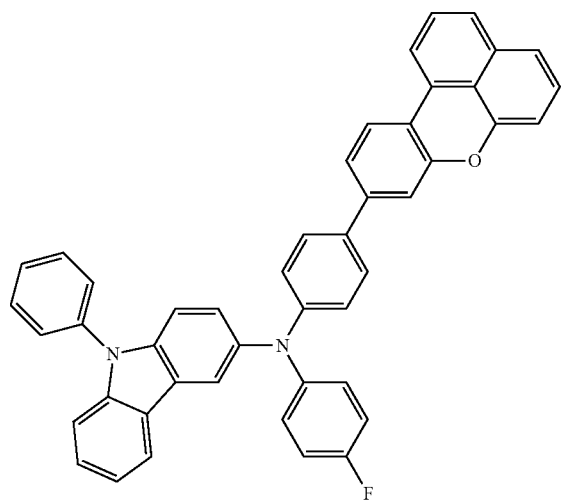
79
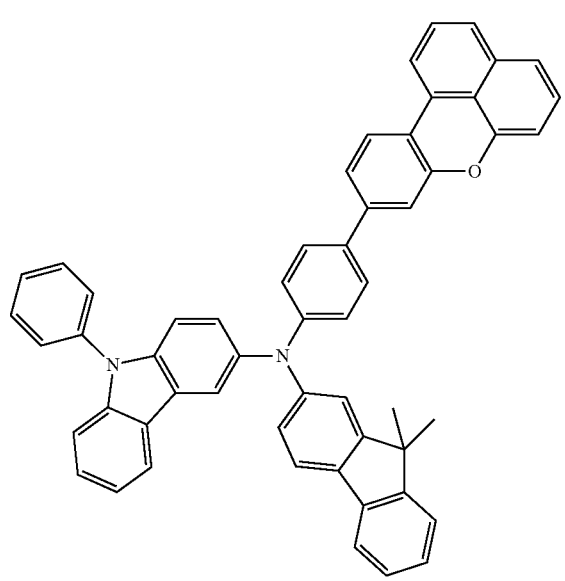
80
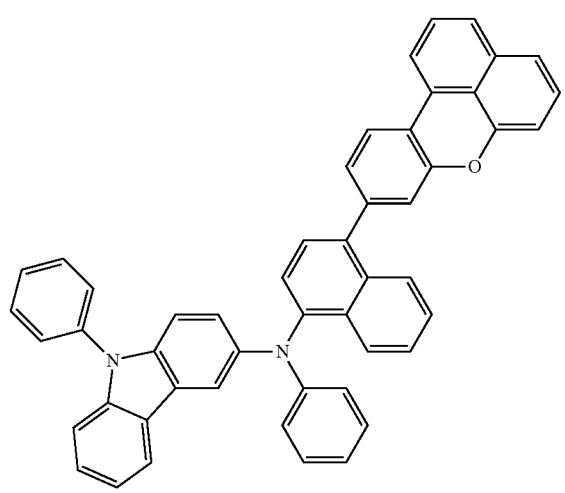
81
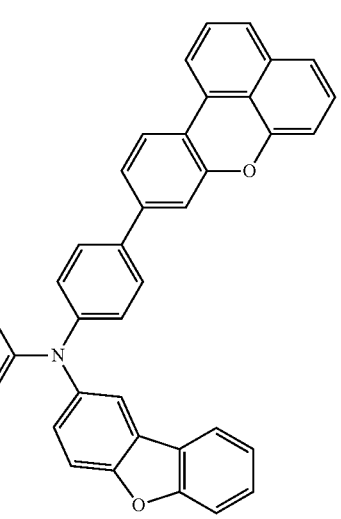
82
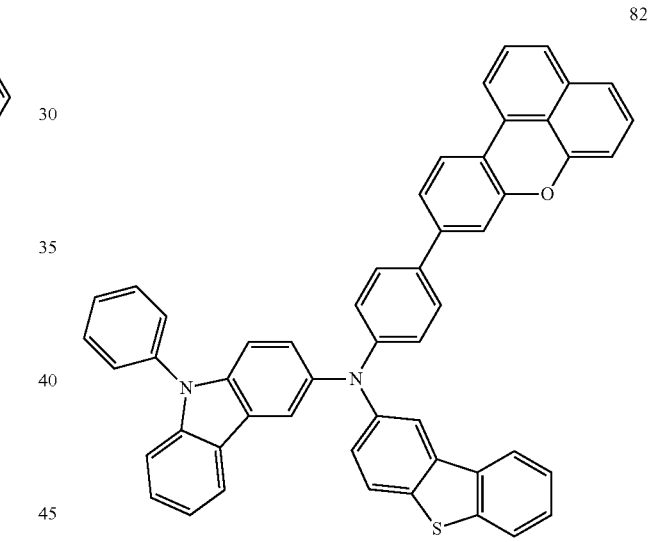
83
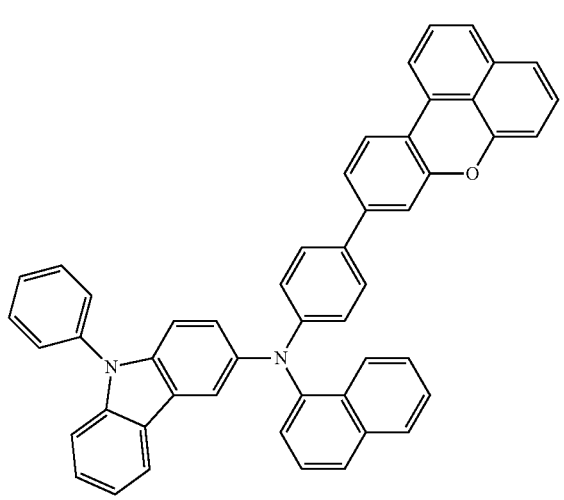

84
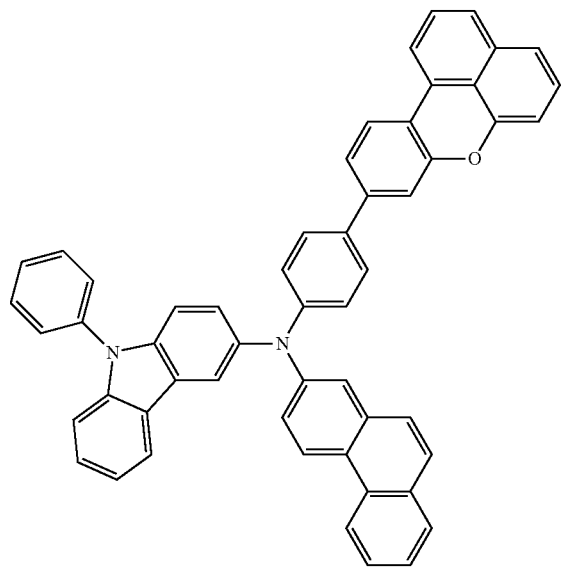
85
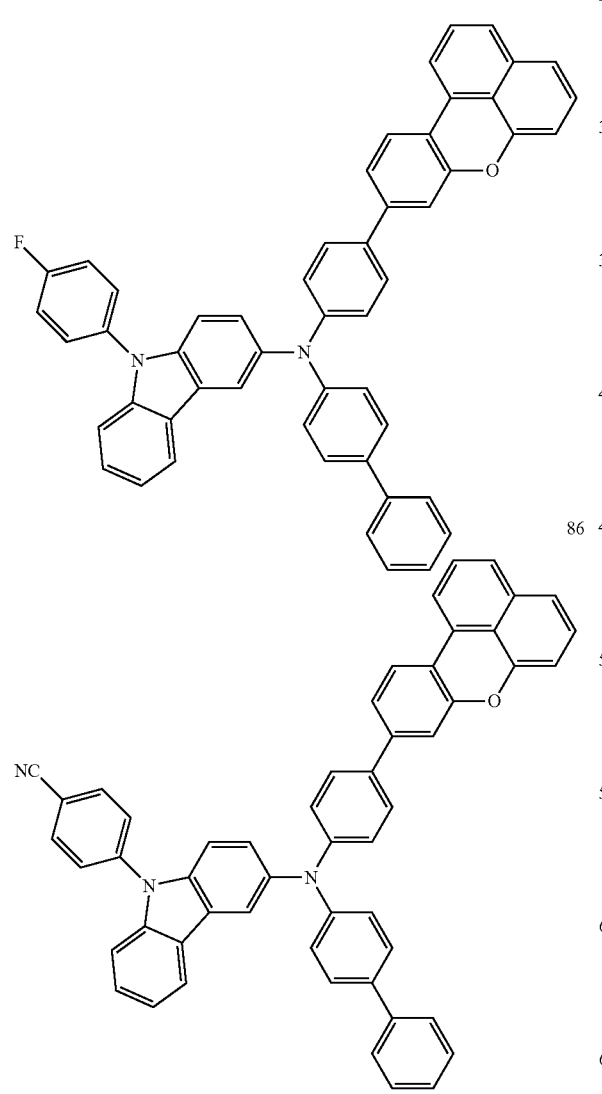
86
87
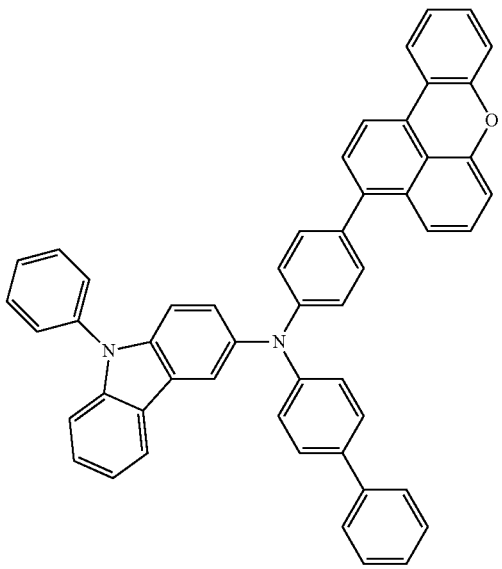
88
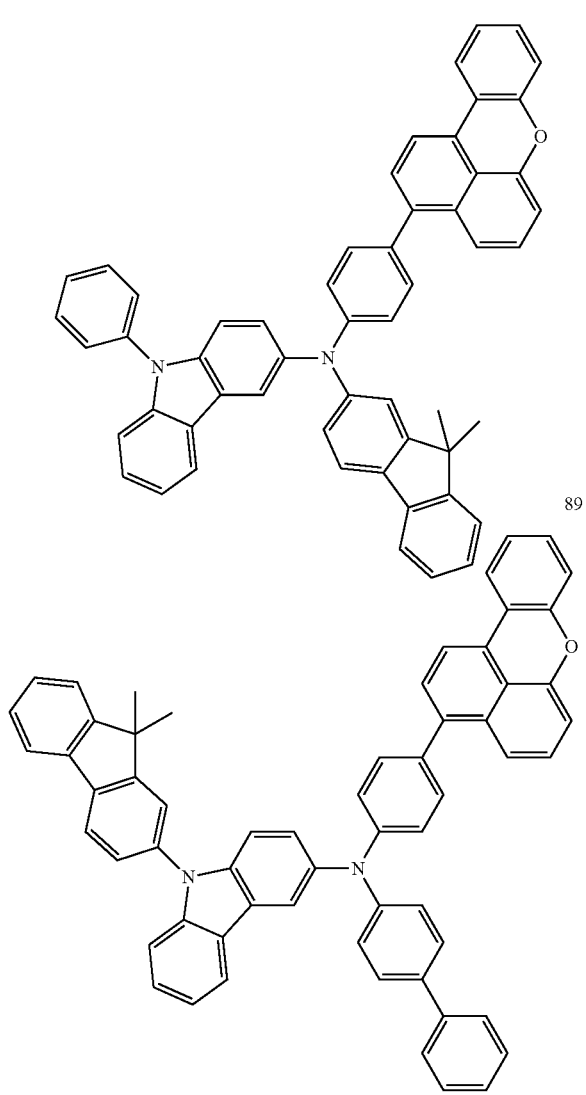
89

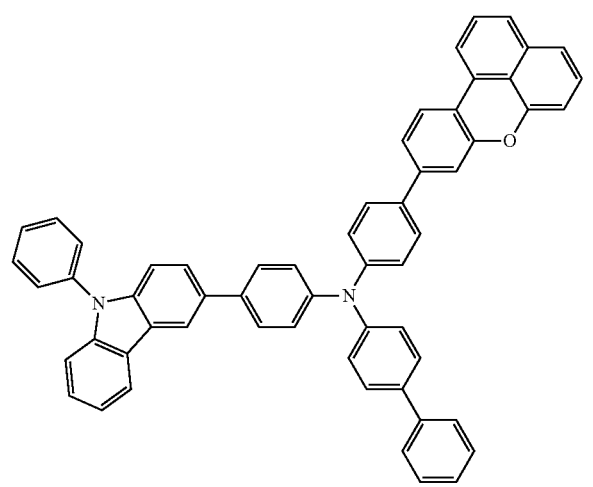
90
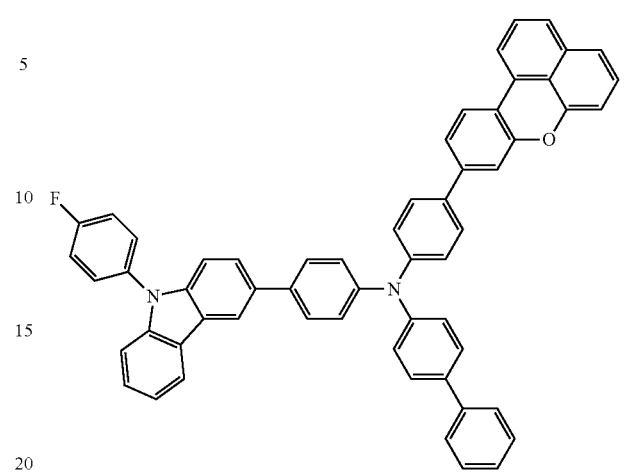
93
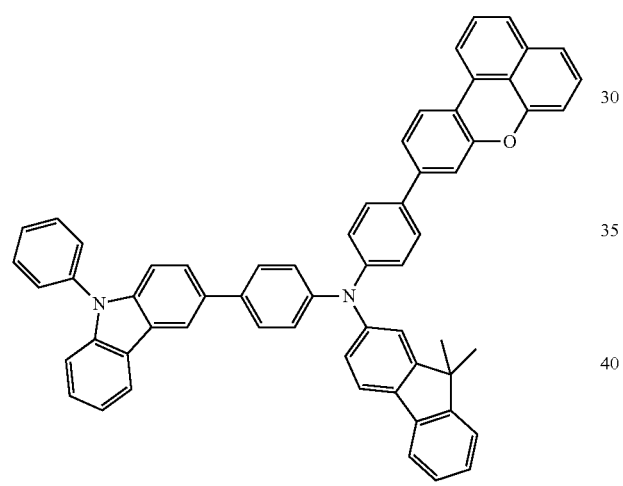
91
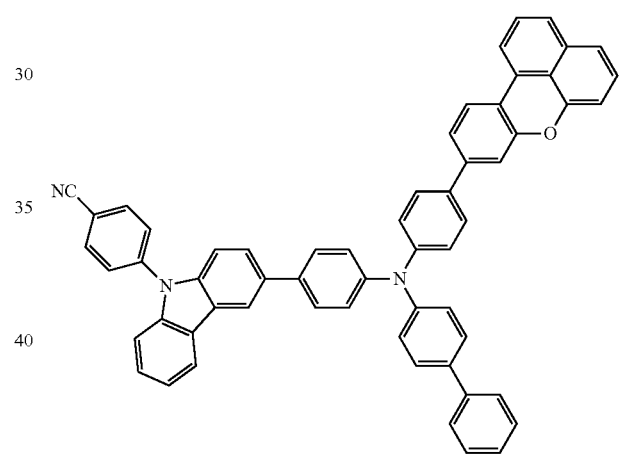
94
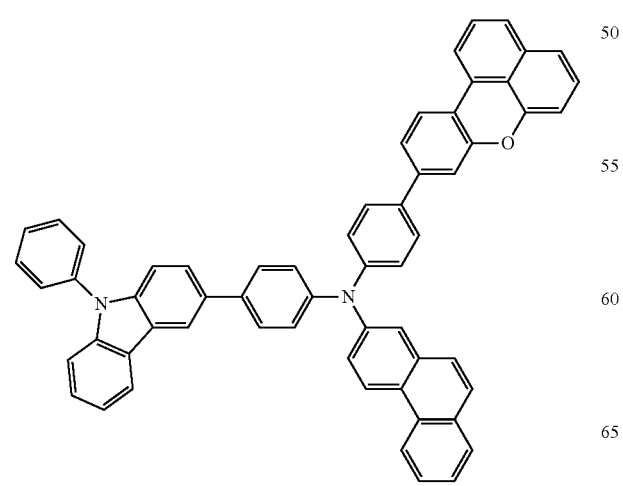
92
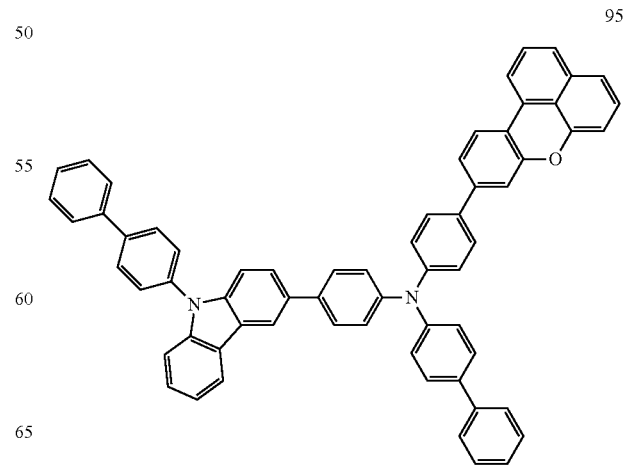
95

-continued
96
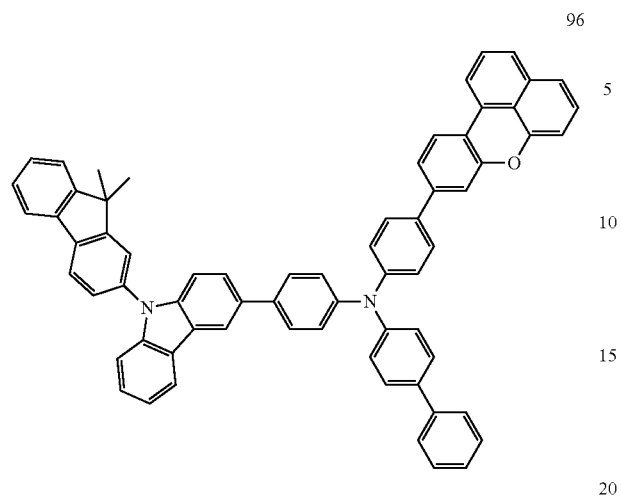
97
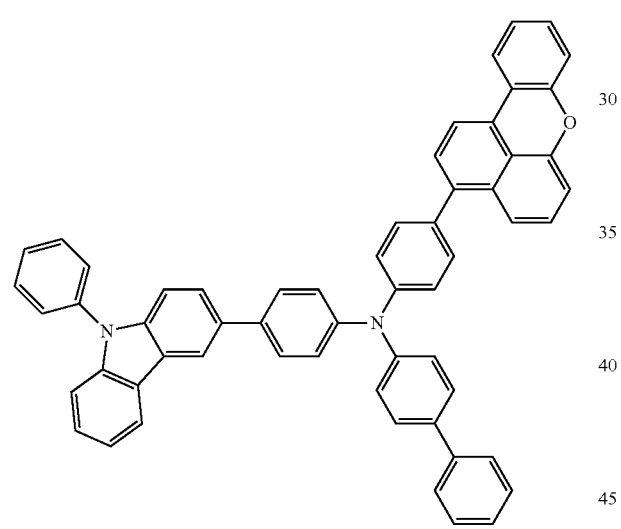
98
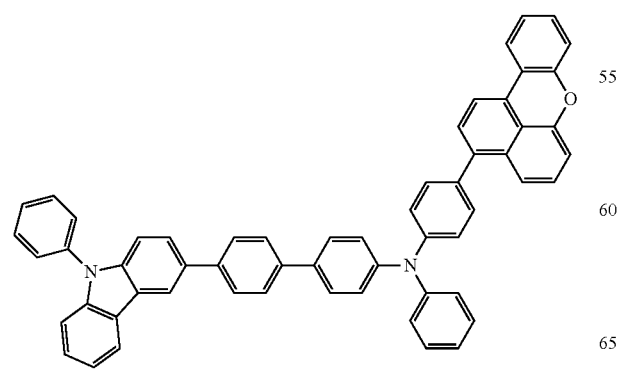
-continued
99
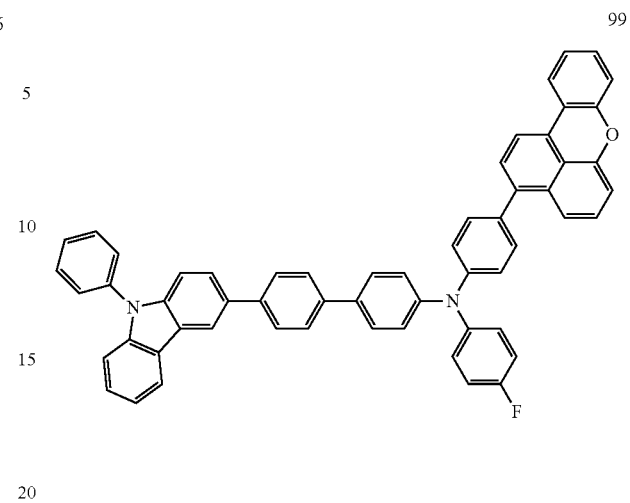
100
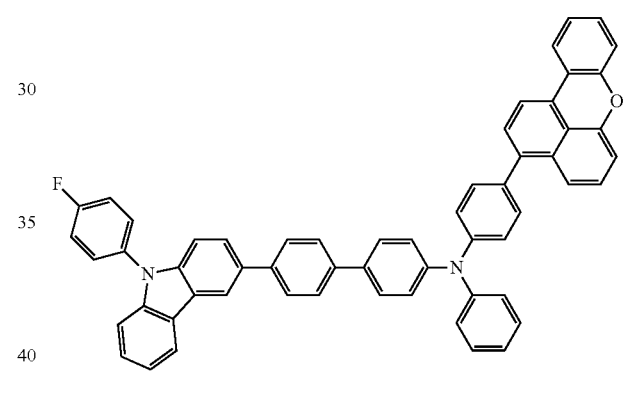
101

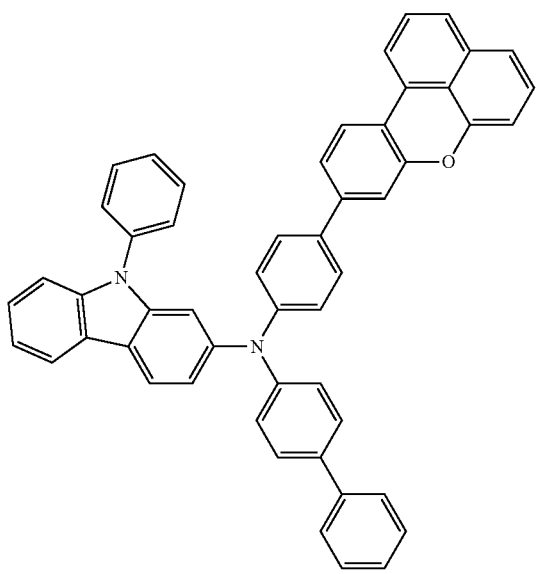
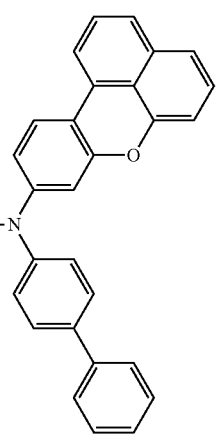
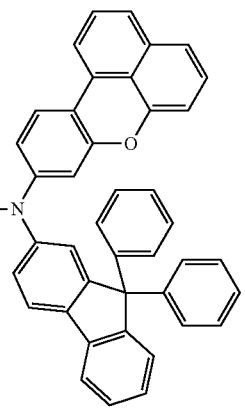
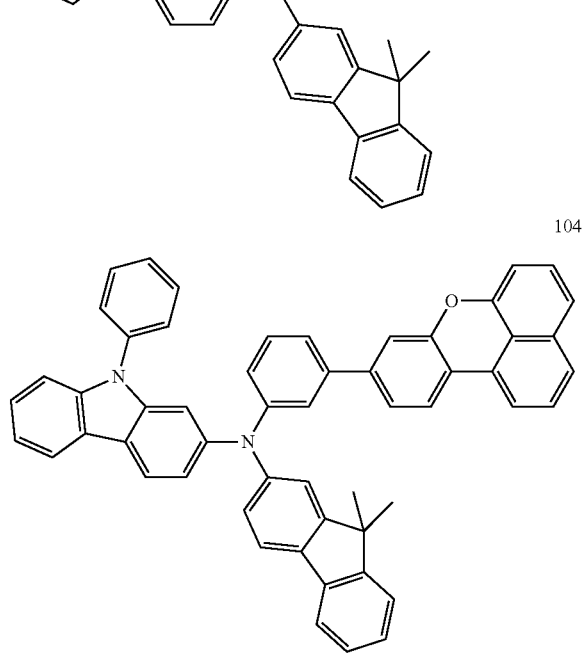
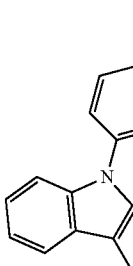

-continued

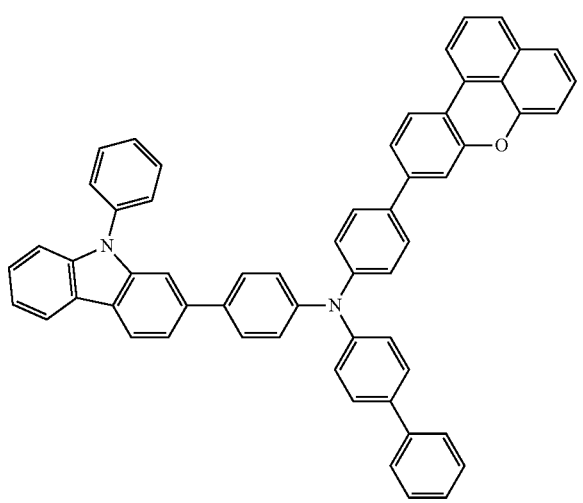

108

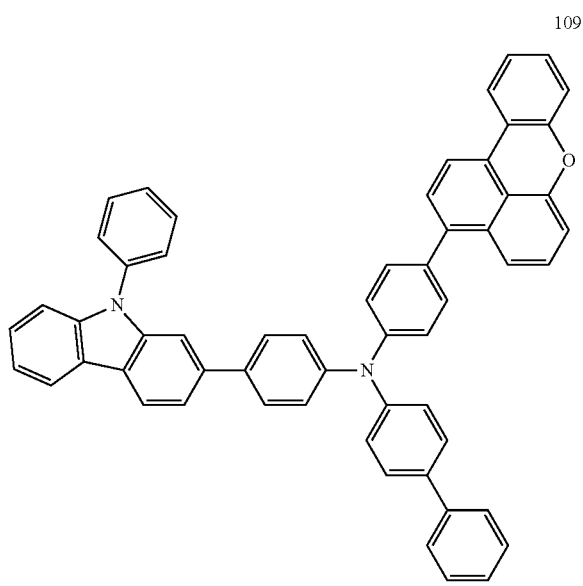

109

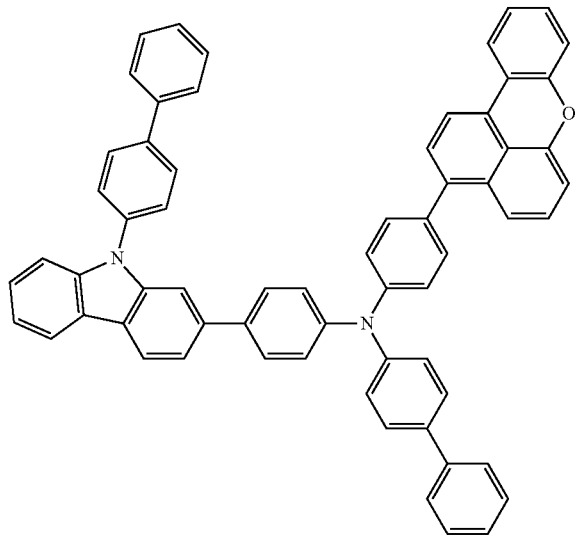

110

The compound represented by Formula 1 may be an amine-based compound in which $Ar_1$ is a group represented by Formula 2 and $Ar_2$ is a group represented by Formula 3A or 3B.

$Ar_2$ in Formula 1 may effectively provide excess electrons from non-paired electron pairs. Accordingly, the amine-based compound of Formula 1 may have a molecular structure with abundant π-electrons. The abundance of π-electrons may increase an electron transition probability, and consequently, the amine-based compound of Formula 1 may provide an improved emission efficiency.

Due to the inclusion of $Ar_1$ (a carbazole-based substituent represented by Formula 2), the amine-based compound of Formula 1 may have improved hole transport capability.

The amine-based compound of Formula 1 may be synthesized using suitable organic synthesis methods, which may be understood based on the following examples that will be described below.

At least one amine-based compounds represented by Formula 1 may be used between a pair of electrodes of an organic light-emitting device. In other implementations, the amine-based compound of Formula 1 may be used as a material for capping layers disposed outwards of a pair of electrodes of an organic light-emitting device. For example, the amine-based compound of Formula 1 may be included in a hole transport region, for example, in a hole transport layer. In some embodiments, the amine-based compound of Formula 1 may be included in an emission layer of the organic light-emitting device.

According to another aspect of the present disclosure, an organic light-emitting device may include a first electrode, a second electrode disposed opposite to the first electrode, and an organic layer disposed between the first electrode and the second electrode and including an emission layer. The organic layer includes at least one of the amine-based compounds of Formula 1.

As used herein, the expression that "(for example, an organic layer may include) at least one of the amine-based compounds of Formula 1" indicates that "(the organic layer may include) one of the amine-based compounds of Formula 1 or at least two different types of the amine-based compounds of Formula 1".

For example, the organic layer may include only Compound 1 as the at least one of amine-based compounds of Formula 1. For example, Compound 1 may be in an hole transport layer of the organic light-emitting device. In some embodiments, the organic layer may include Compounds 1 and 2 as the at least one of amine-based compounds of Formula 1. For example, Compounds 1 and 2 may be in the same layer (for example, both in the hole transport layer) or in different layers (for example, Compound 1 may be in the hole transport layer, and Compound 2 may be in the emission layer).

In some embodiments, the organic layer may include i) a hole transport region disposed between the first electrode (anode) and the emission layer and including at least one of a hole injection layer, a hole transport layer, a buffer layer, and an electron blocking layer, and ii) an electron transport region disposed between the emission layer and the second electrode (cathode) and including at least one of a hole blocking layer, an electron transport layer, and an electron injection layer. At least one of the hole transport region and the emission layer may include the at least one of the amine-based compounds of Formula 1. For example, the hole transport region may include a hole transport layer, and the hole transport layer may include the at least one of the amine-based compounds of Formula 1.

In some embodiments, the hole transport region may include at least one of a hole injection layer and a hole transport layer, and the at least one of a hole injection layer and a hole transport layer may include the at least one of the amine-based compounds of Formula 1.

In some embodiments, the organic light-emitting device may further include at least one of a first capping layer and a second capping layer, the first capping layer being disposed on an optical path along which light generated in the emission layer passes outwardly through the first electrode, and the second capping layer being disposed on an optical path along which the light generated in the emission layer passes outwardly through the second electrode. At least one of the first and second capping layers may include at least one of the amine-based compounds of Formula 1.

For example, the organic light-emitting device may have i) a stack structure in which the first electrode, the organic layer, the second electrode, and the second capping layer are sequentially stacked upon one another in the stated order, ii) a stack structure in which the first capping layer, the first electrode, the organic layer, and the second electrode are sequentially stacked upon one another in the stated order, or iii) a stack structure in which the first capping layer, the first electrode, the organic layer, the second electrode, and the second capping layer are sequentially stacked upon one another in the stated order. At least one of the first capping layer and the second capping layer may include the amine-based compound of Formula 1.

As used herein, the term "organic layer" refers to a single layer and/or a plurality of layers disposed between the first and second electrodes of the organic light-emitting device. The "organic layer" may also include materials other than an organic material.

Figure 1:
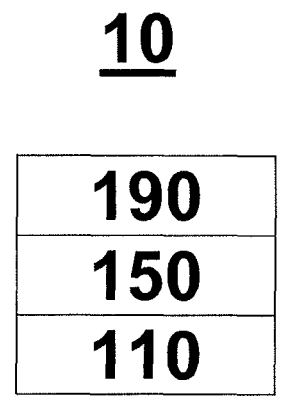

Hereinafter, a structure of an organic light-emitting device according to an embodiment of the present disclosure and a method of manufacturing the same will now be described with reference to FIG. 1.

FIG. 1 illustrates a schematic sectional view of an organic light-emitting device 10 according to an embodiment of the present disclosure. Referring to FIG. 1, the organic light-emitting device 10 includes a first electrode 110, an organic layer 150, and a second electrode 190.

A substrate may be disposed under the first electrode 110 or on the second electrode 190 in FIG. 1. The substrate may be a substrate with good mechanical strength, thermal stability, transparency, surface smoothness, ease of handling, and water resistance. For example, the substrate may be a glass or transparent plastic substrate.

The first electrode 110 may be formed by depositing or sputtering a first electrode-forming material on the substrate. When the first electrode 110 is an anode, a material having a high work function may be used as the first electrode-forming material to facilitate hole injection. The first electrode 110 may be a reflective electrode, a semi-transmissive electrode, or a transmissive electrode. Transparent and conductive materials such as ITO, IZO, $SnO_2$, and ZnO may be used to form the first electrode. The first electrode 110 as a semi-transmissive electrode or a reflective electrode may be formed of at least one material selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure including a plurality of layers. For example, the first electrode 110 may have a three-layered structure of ITO/Ag/ITO.

The organic layer 150 may be disposed on the first electrode 110. The organic layer 150 may include an emission layer (EML).

The organic layer 150 may further include a hole transport region disposed between the first electrode and the EML, and an electron transport region between the EML and the second electrode.

For example, the hole transport region may include at least one of a hole injection layer (HIL), a hole transport layer (HTL), a buffer layer, and an electron blocking layer (EBL). For example, the electron transport layer may include at least one of a hole blocking layer (HBL), an electron transport layer (ETL), and an electron injection layer (EIL). The hole transport region may have a single-layered structure including a single material, a single-layered structure including a plurality of materials, or a multi-layered structure including a plurality of layers including different materials.

In some embodiments, the hole transport region may have a single-layered structure including a plurality of materials, or a multi-layered structure of HIL/HTL, HIL/HTL/buffer layer. HIL/buffer layer, HTL/buffer layer, or HIL/HTL/EBL, wherein these layers forming a multi-layered structure are sequentially disposed on the first electrode 110 in the order stated above.

When the hole transport region includes a HIL, the HIL may be formed on the first electrode 110 by using any of a suitable method, for example, by using vacuum deposition, spin coating, casting, Langmuir-Blodgett (LB) deposition, inkjet printing, laser printing, laser induced thermal imaging (LITI), or the like.

When the HIL is formed using vacuum deposition, the deposition conditions may vary depending on the material that is used to form the HIL and the structure of the HIL. For example, the deposition conditions may be selected from the following conditions: a deposition temperature of about 100° C. to about 500° C., a degree of vacuum of about $10^{-8}$ to about $10^{-3}$ torr, and a deposition rate of about 0.01 to 100 Å/sec.

When the HIL is formed using spin coating, the coating conditions may vary depending on the material that is used to form the HIL and the structure of the HIL. For example, the coating conditions may be selected from the following conditions: a coating rate of about 2,000 rpm to about 5,000 rpm and a heat treatment temperature of about 800° C. to about 200° C.

When the hole transport region includes a HTL, the HTL may be formed on the first electrode 110 or the I-IL by using a suitable method, for example, by using vacuum deposition, spin coating, casting, Langmuir-Blodgett (LB) deposition, inkjet printing, laser printing, laser induced thermal imaging (LITI), or the like. When the HTL is formed using vacuum deposition or spin coating, the conditions for deposition and coating may be similar to the above-described deposition and coating conditions for forming the HIL.

The hole transport region may include the amine-based compound of Formula 1. For example, the hole transport region may include a hole transport layer, and the hole transport layer may include the amine-based compound of Formula 1.

In some embodiments, the hole transport region may include, in addition to at least one amine-based compound of Formula 1, at least one of m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate)(PEDOT/PSS), polyaniline/camphor sulfonic acid (Pani/CSA), polyaniline/poly(4-styrenesulfonate) (PANI/PSS), a compound represented by Formula 201, and a compound represented by Formula 202.

-continued
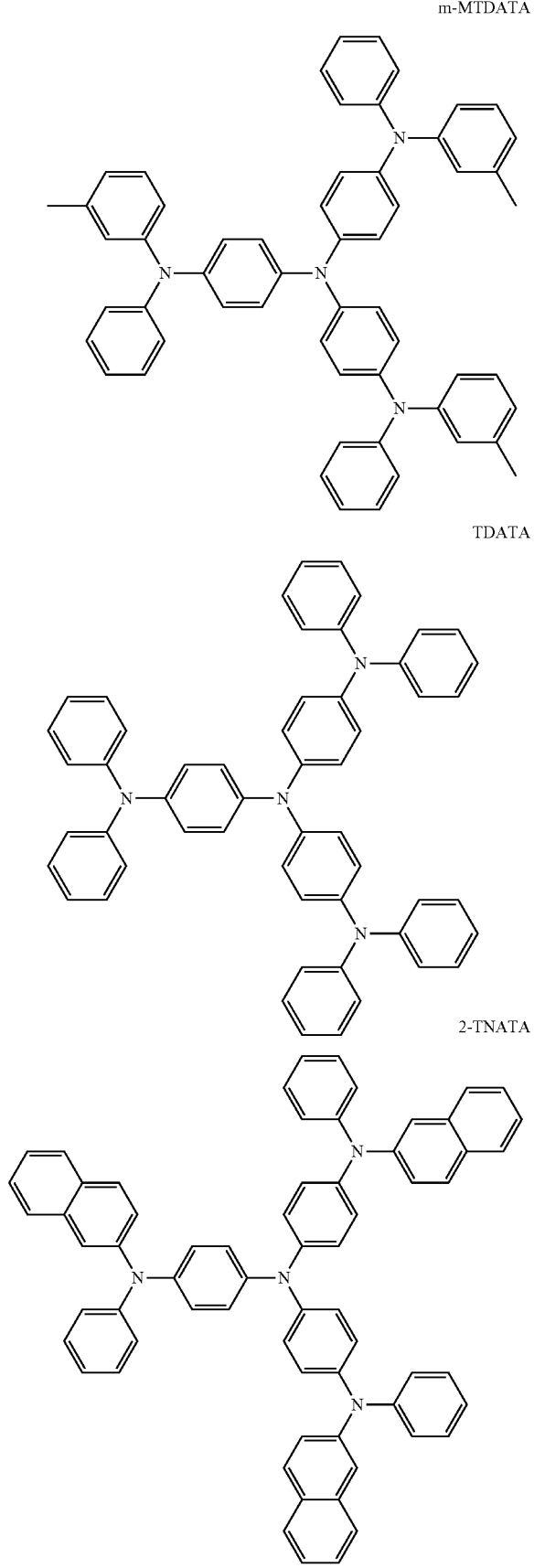
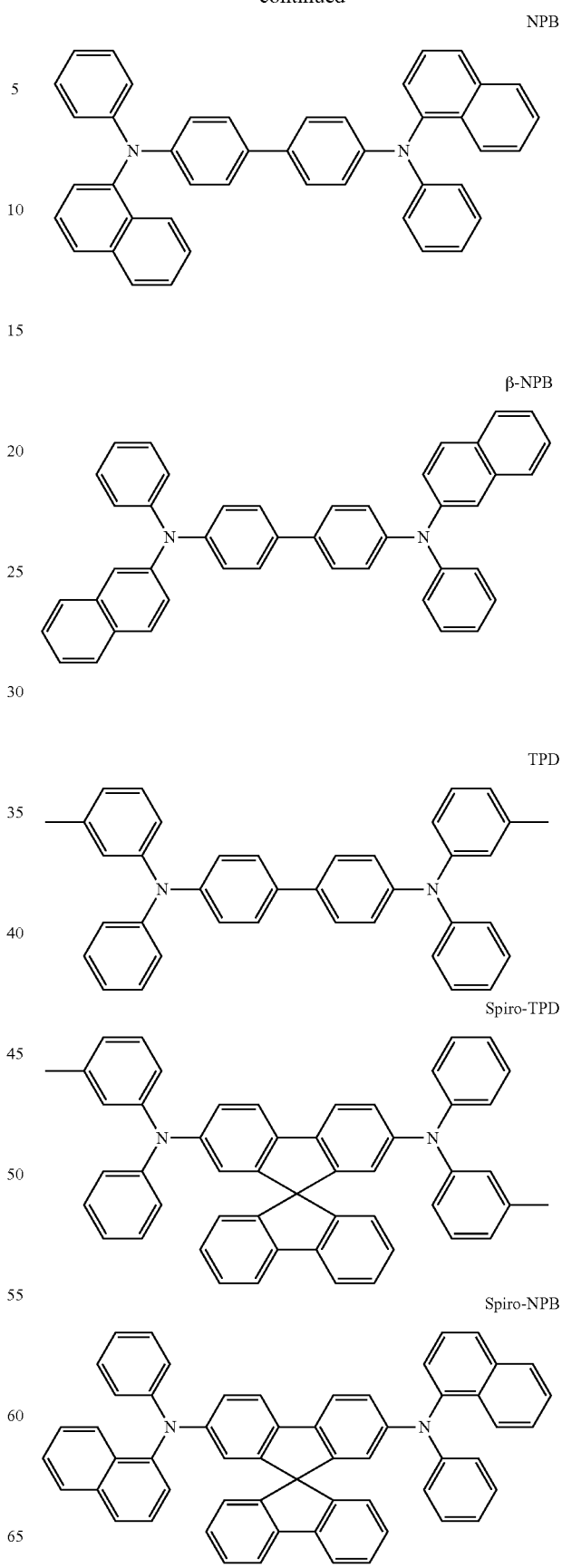

-continued methylated NPB

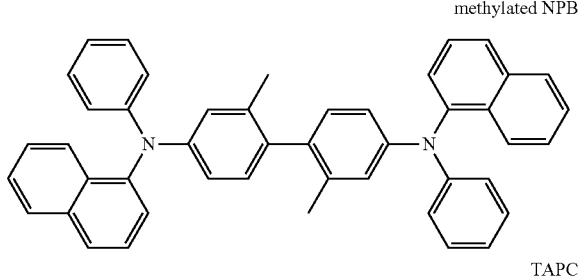

TAPC

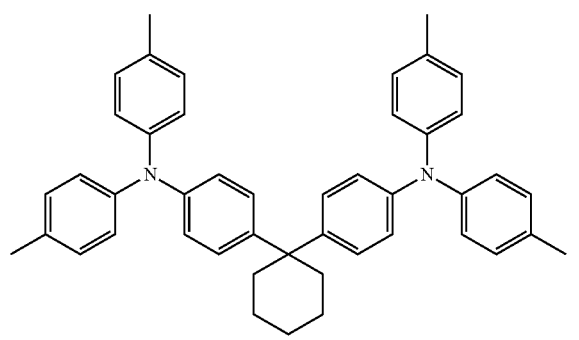

HMTPD

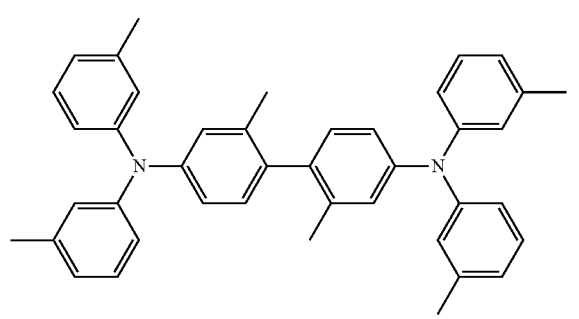

Formula 201

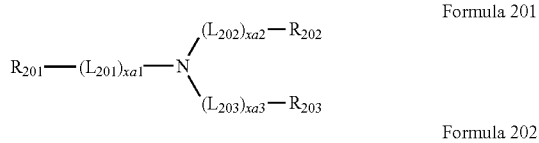

Formula 202

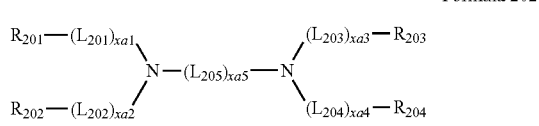

In Formulae 201 and 202, $L_{201}$ to $L_{205}$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xa1 to xa4 may be each independently selected from 0, 1, 2, and 3;

xa5 may be selected from 1, 2, 3, 4, and 5; and $R_{201}$ to $R_{205}$ may be defined as described above herein in conjunction with $R_3$.

The compound of Formula 201 may be a compound represented by Formula 201A:

Formula 201A

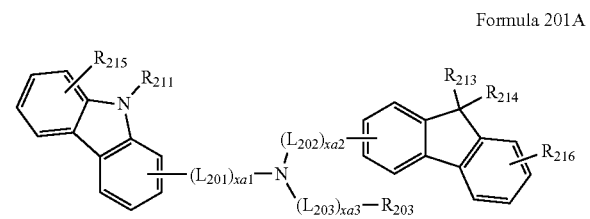

For example, the compound of Formula 201 may be a compound represented by Formula 201A-1:

Formula 201A-1

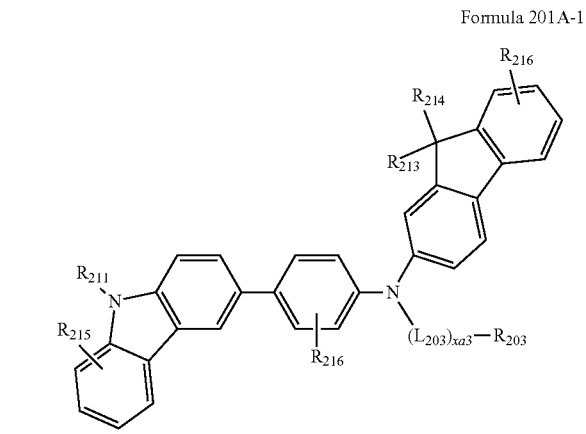

The compound of Formula 202 may be a compound represented by Formula 202A:

Formula 202A

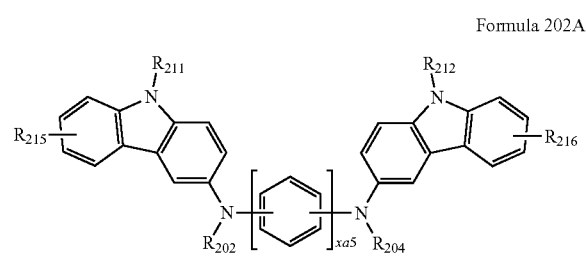

In Formulae 201A, 201A-1, and 202A, $L_{201}$ to $L_{203}$, xa1 to xa3, xa5, and $R_{202}$ to $R_{204}$ may be the same as those described above herein.

$R_{211}$ and $R_{212}$ may be defined as described above herein in conjunction with $R_{203}$.

$R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

For example, in Formulae 201A, 201A-1, and 202A, $L_{201}$ to $L_{203}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently 0 or 1;

$R_{203}$, $R_{204}$, $R_{205}$, $R_{211}$, and $R_{212}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may be each independently selected from:

a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 may be 1 or 2.

In Formulae 201A and 201A-1, $R_{213}$ and $R_{214}$ may be linked to each other to form a saturated or unsaturated ring.

The compound of Formula 201 and the compound of Formula 202 may each independently be selected from Compounds HT1 to HT20, as examples.

HT1

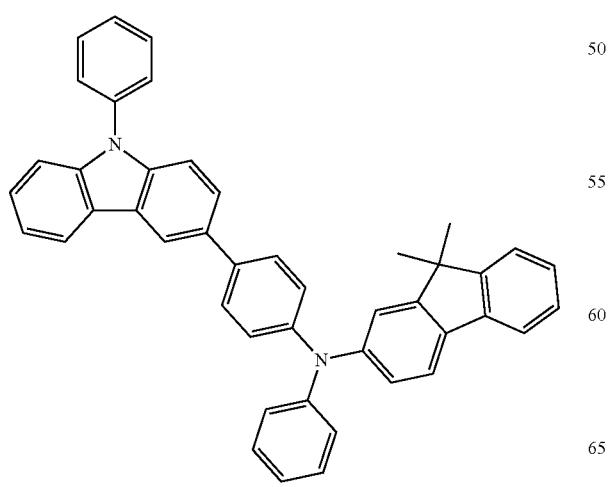

HT2

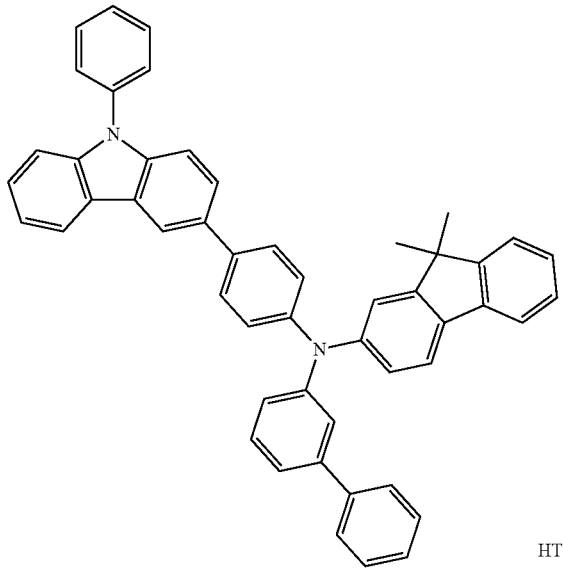

HT3

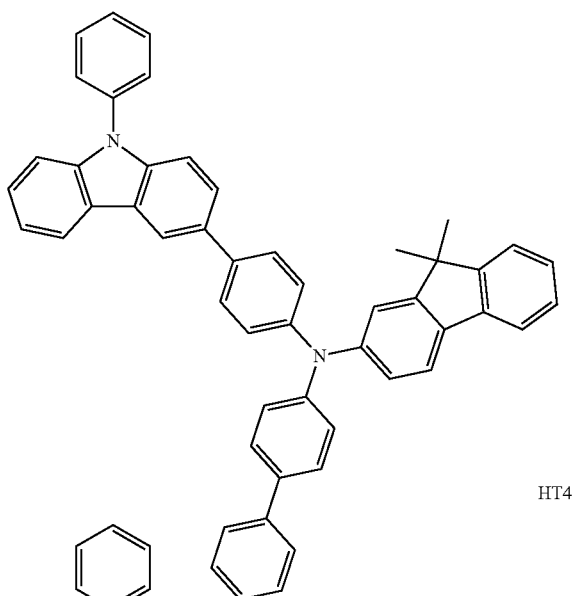

HT4

-continued
HT5
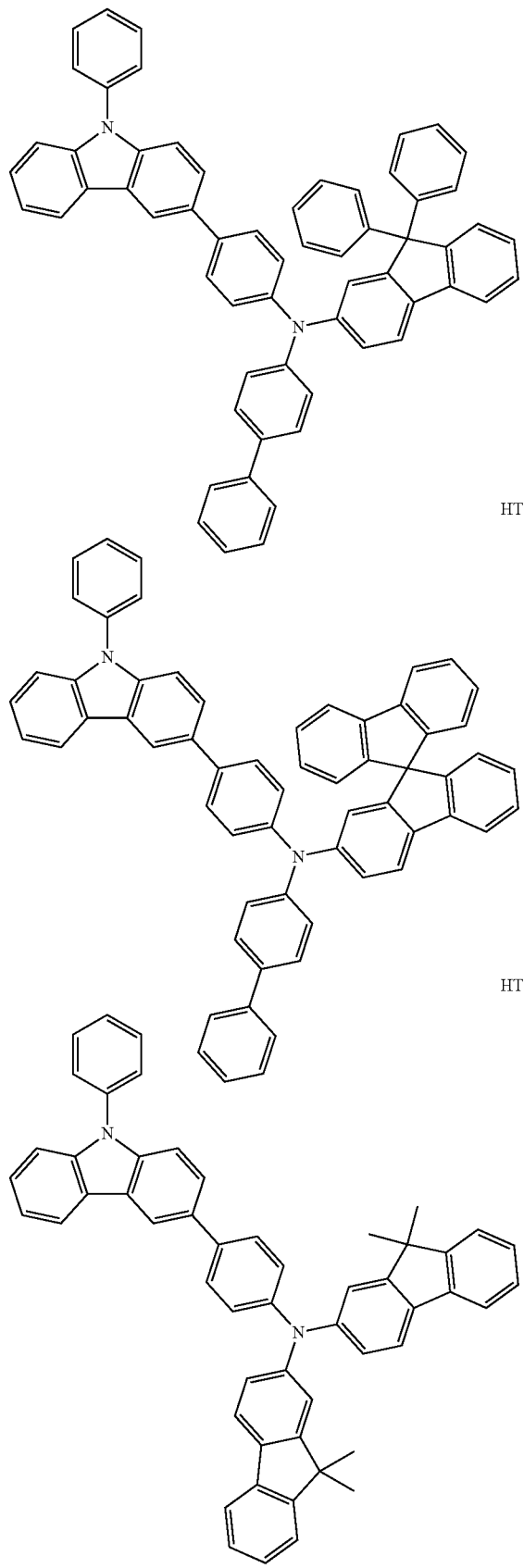
HT6
HT7
-continued
HT8
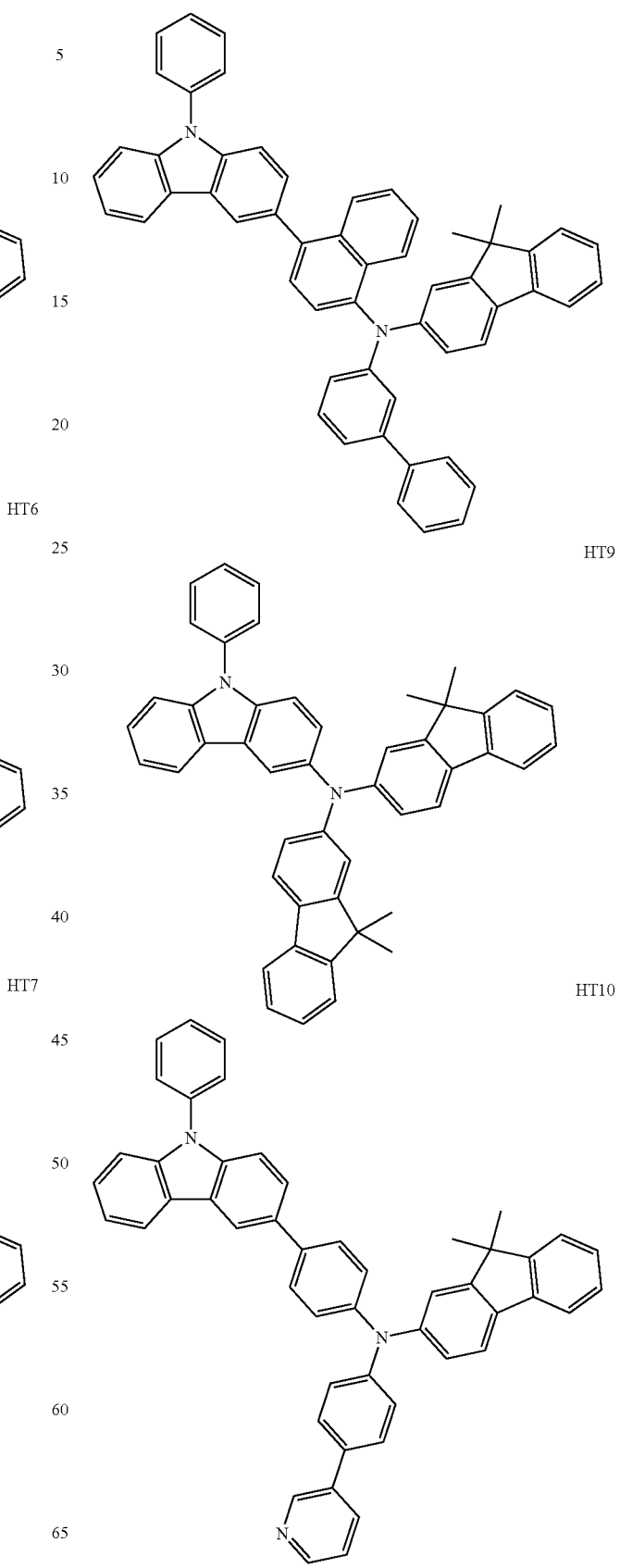
HT9
HT10

HT11
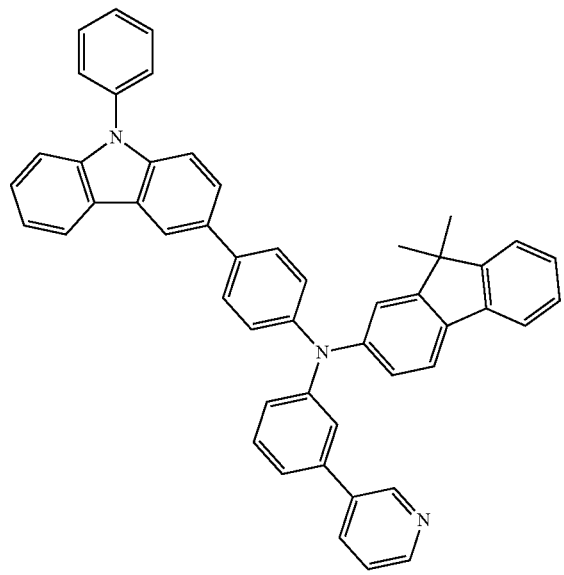
HT12
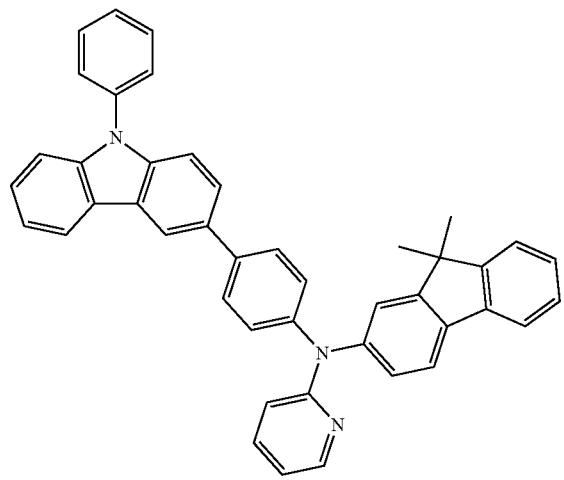
HT13
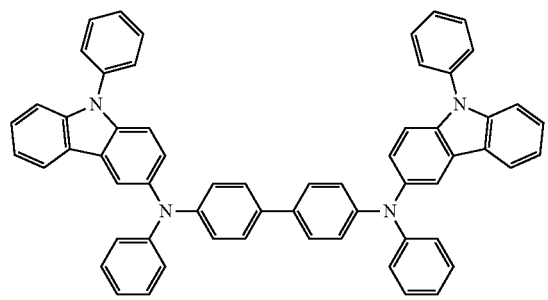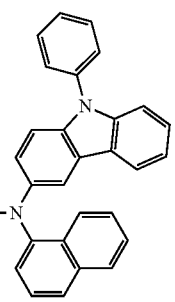
HT14
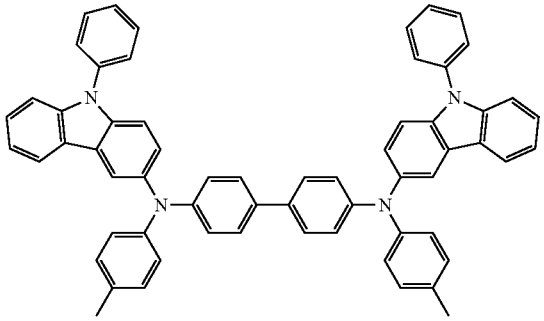
HT15
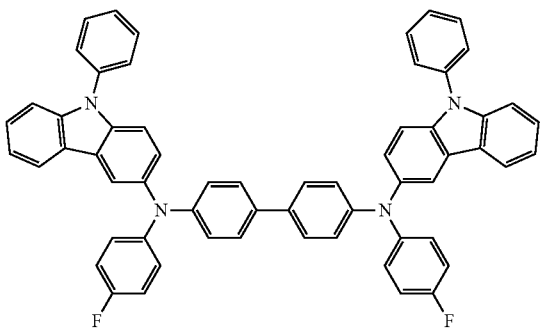
HT16
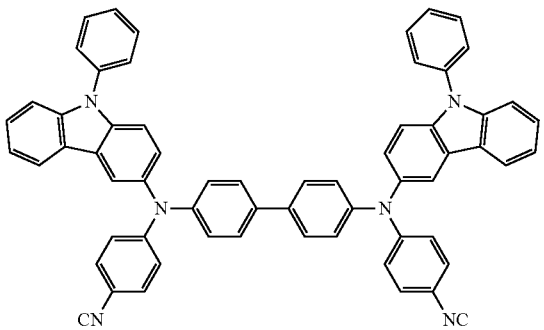
HT17

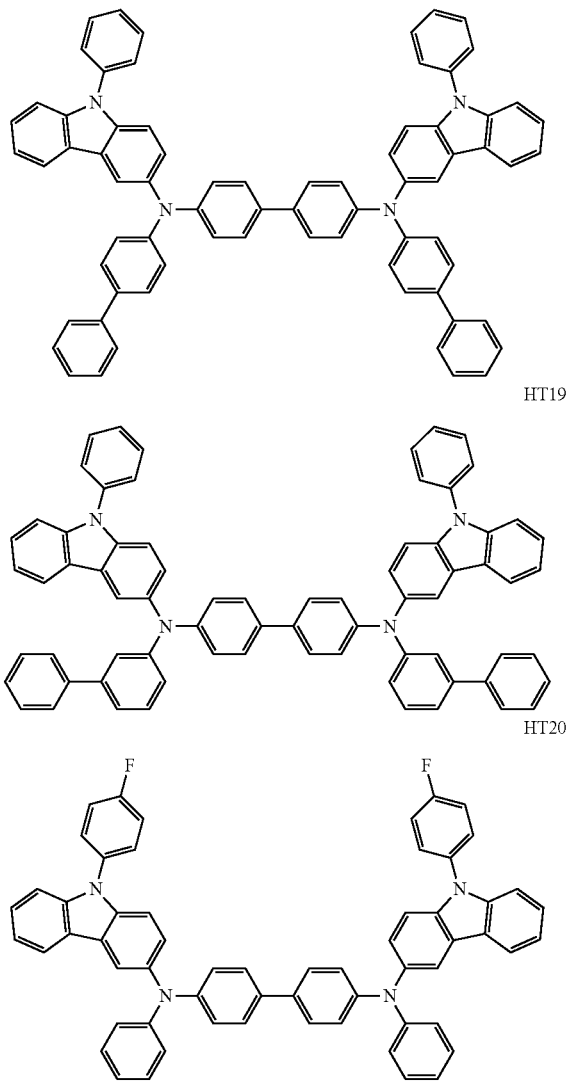

A thickness of the hole transport region may be from about 100 Å to about 10,000 Å, and in some embodiments, from about 100 Å to about 1,000 Å. When the hole transport region includes a HIL and a HTL, a thickness of the HIL may be from about 100 Å to about 10,000 Å, and in some embodiments, from about 100 Å to about 1,000 Å, and a thickness of the HTL may be from about 50 Å to about 2,000 Å, and in some embodiments, from about 100 Å to about 1,500 Å. When the thicknesses of the hole transport region, the HIL, and the HTL are within these ranges, satisfactory hole transport characteristics may be obtained without a substantial increase in driving voltage.

The hole transport region may further include a charge-generating material to improve conductivity, in addition to the materials as described above. The charge-generating material may be homogeneously or inhomogeneously dispersed in the hole transport region.

The charge-generating material may be, for example, a p-dopant. The p-dopant may be one of quinone derivatives, metal oxides, and cyano group-containing compounds. Examples of the p-dopant include quinone derivatives such as tetracyanoquinonedimethane (TCNQ), 2,3,5,6-tetra-fluoro-tetracyano-1,4-benzoquinonedimethane (F4-TCNQ), or the like; metal oxides such as tungsten oxide, molybdenum oxide, or the like; and Compound HT-D1.

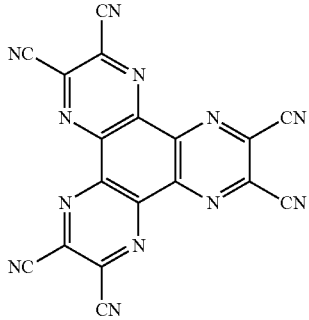

<Compound HT-D1>

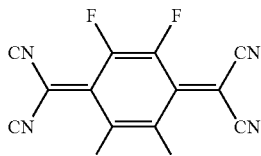

<F4-TCNQ>

The hole transport region may further include at least one of a buffer layer and an EBL, in addition to the HIL and HTL described above. The buffer layer may compensate for an optical resonance distance of light according to a wavelength of the light emitted from the EML, and thus may improve light-emission efficiency. A material in the buffer layer may be a suitable material for use in the hole transport region. The EBL may block migration of electrons from the electron transport region into EML.

The EML may be formed on the first electrode 110 or the hole transport region by using a suitable method, for example, by using vacuum deposition, spin coating, casting, Langmuir-Blodgett (LB) deposition, inkjet printing, laser printing, laser induced thermal imaging (LITI), or the like. When the EML is formed using vacuum deposition or spin coating, the deposition and coating conditions for forming the EML may be similar to the above-described deposition and coating conditions for forming the HIL.

When the organic light-emitting device 10 is a full color organic light-emitting device, the EML may be patterned into a red emission layer, a green emission layer, and a blue emission layer to correspond to individual subpixels, respectively. In some embodiments, the EML may have a structure in which a red emission layer, a green emission layer and a blue emission layer are stacked upon one another, or a structure including a mixture of a red light-emitting material, a green light-emitting material, and a blue light-emitting material without separation of layers for the different color emission, and thus may emit white light.

The EML may include a host and a dopant.

In some embodiments, the host may include a compound represented by Formula 301.

$$Ar_{301}\text{-}[(L_{301})_{xb1}\text{-}R_{301}]_{xb2} \quad \text{Formula 301}$$

In Formula 301, $Ar_{301}$ may be selected from:

a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, and a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$), wherein $Q_{301}$ to $Q_{303}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group:

$L_{301}$ may be defined as described above herein in conjunction with $L_1$, $R_{301}$ may be selected from:

a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3;

xb2 may be selected from 1, 2, 3, and 4.

For example, in Formula 301, $L_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and $R_{301}$ may be selected from a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group.

For example, the host may include a compound represented by Formula 301A:
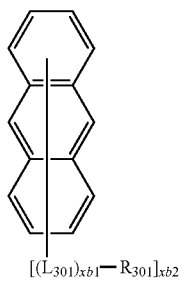
Formula 301A
In Formula 301A, $L_{301}$, xb1, $R_{301}$ and xb2 may be the same as those defined herein.
The compound of Formula 301 may include at least one of Compounds H1 to H42.
H1
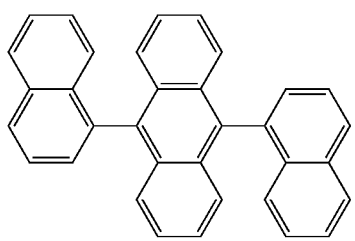
H2
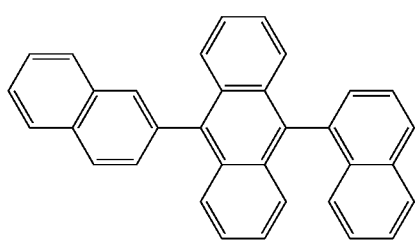
H3
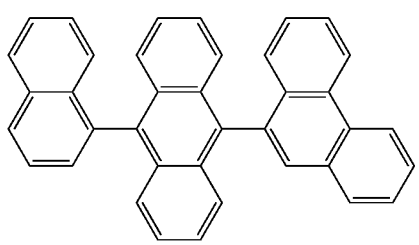
H4
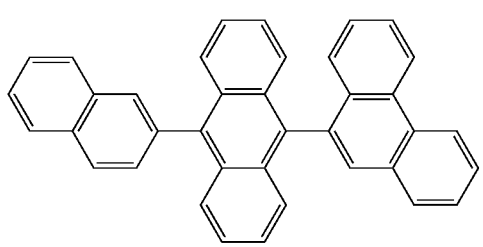
H5
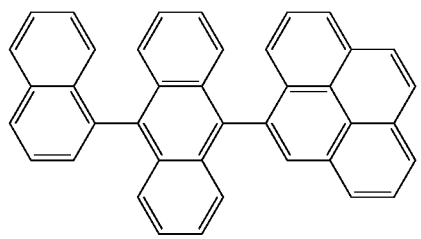
H6
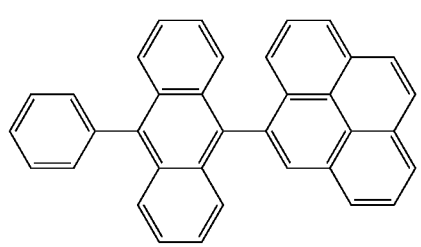
H7
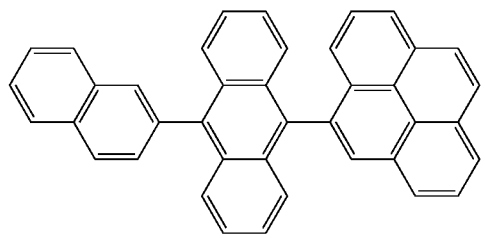
H8
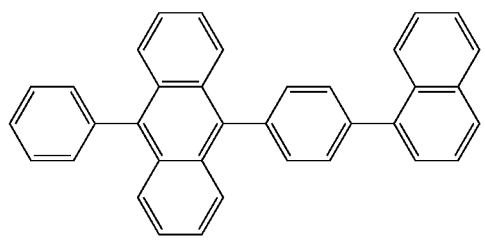
H9
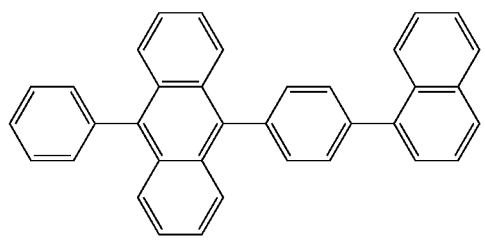
H10

H11
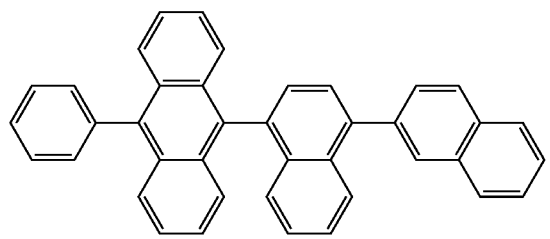
H12
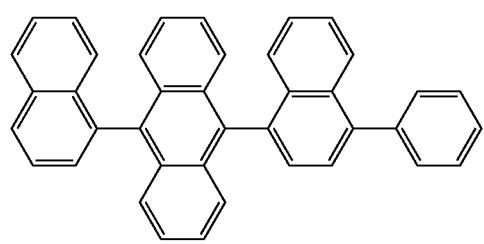
H13
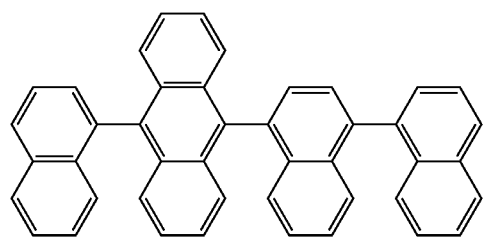
H14
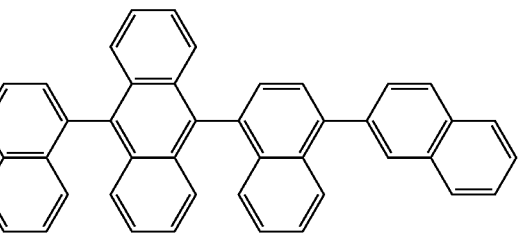
H15
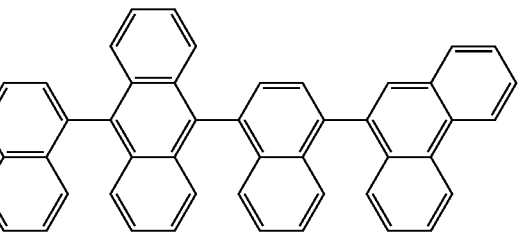
H16
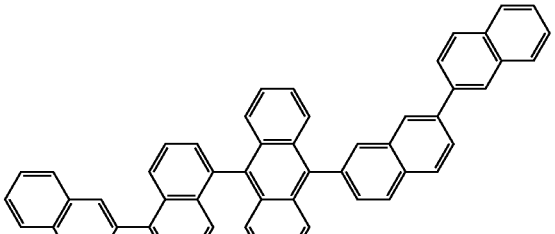
H17
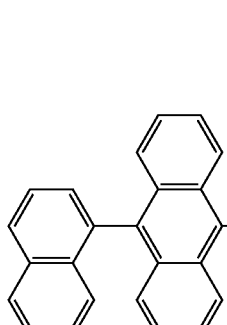
H18
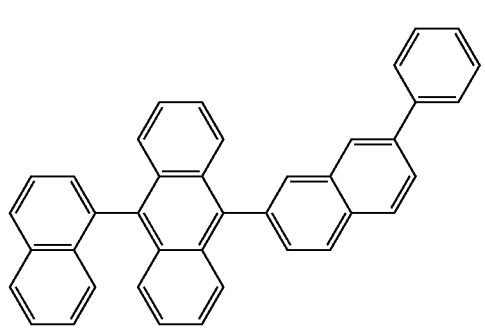
H19
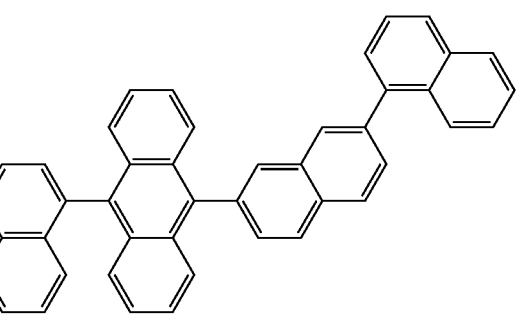
H20
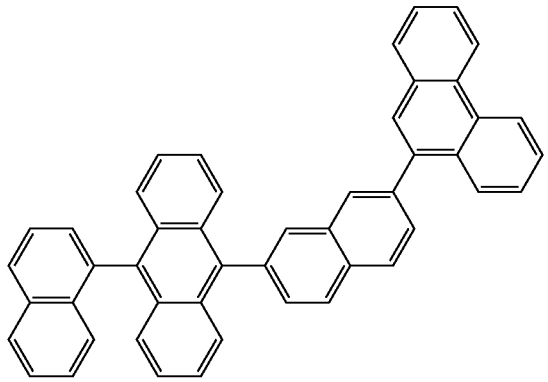
H21
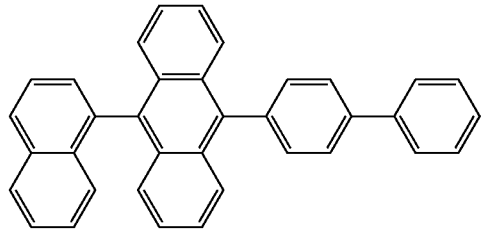

H22 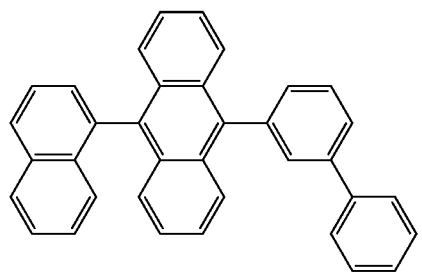
H23 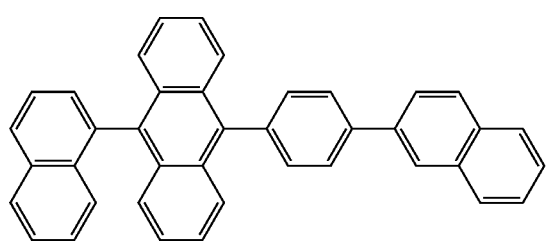
H24 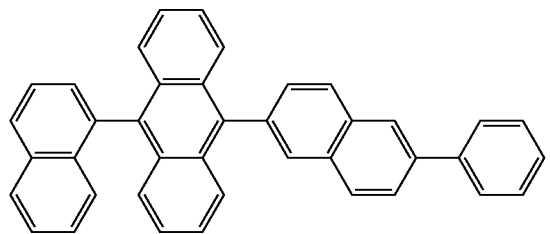
H25 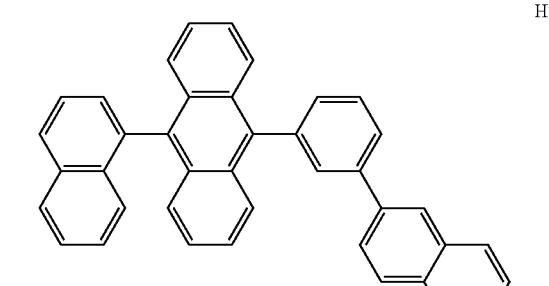
H26 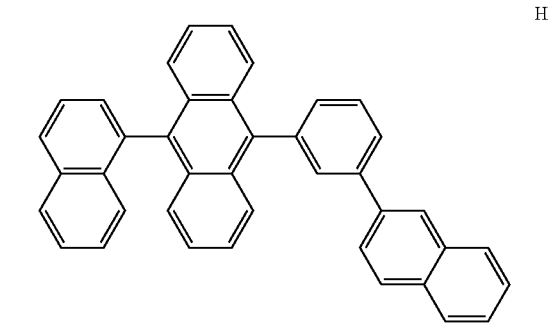
H27 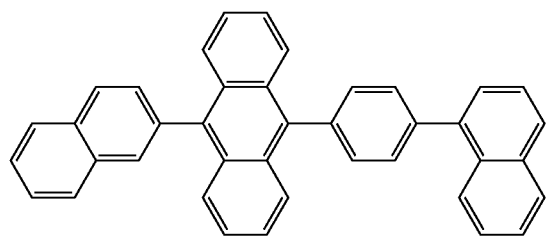
H28 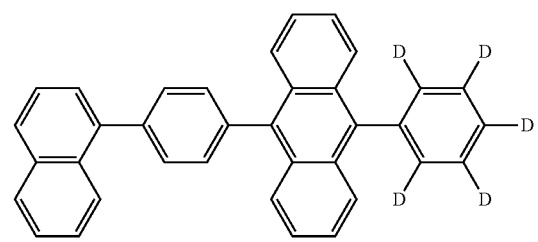
H29 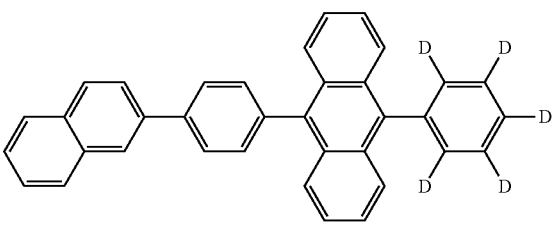
H30 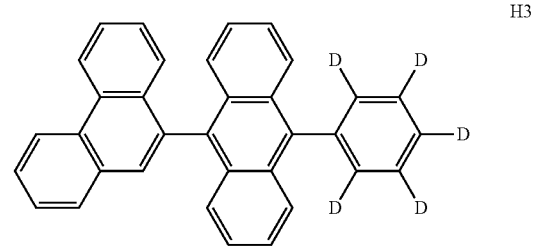
H31 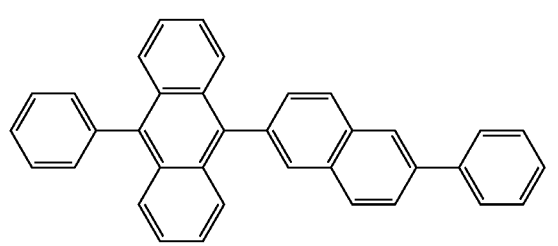
H32 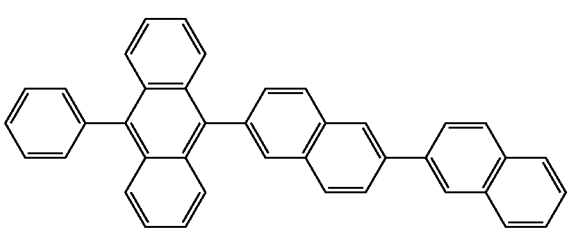

H33
H34
H35
H36
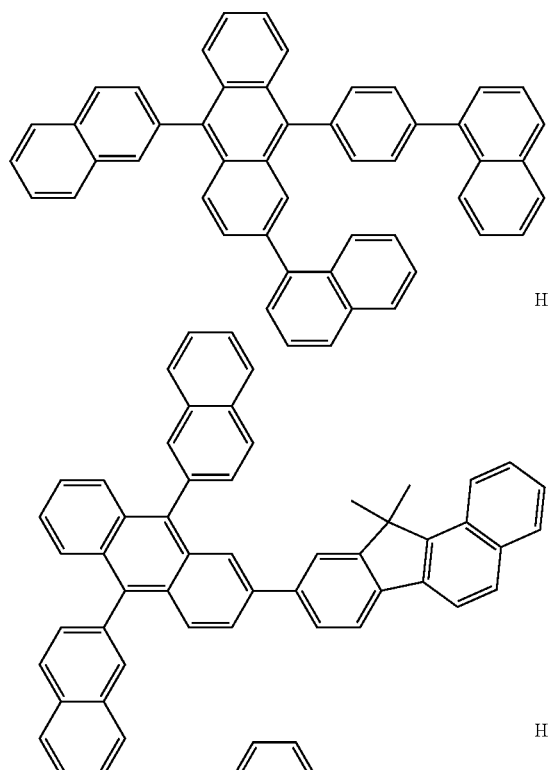
H37
H38
H39
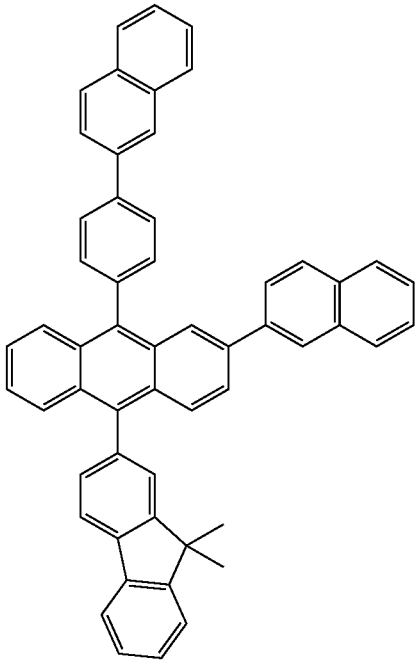
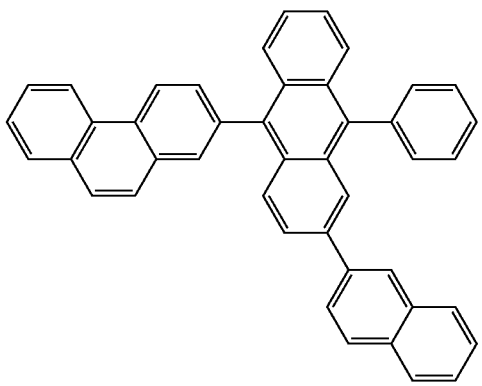
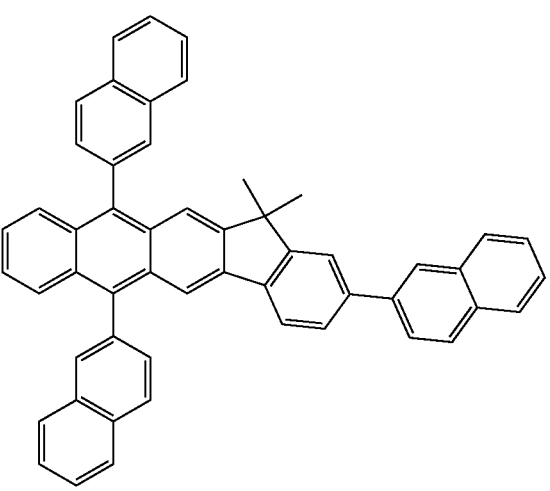

H40
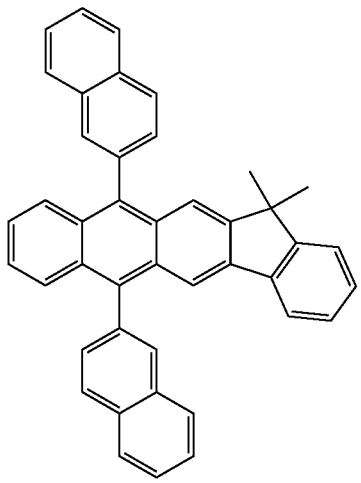
H41
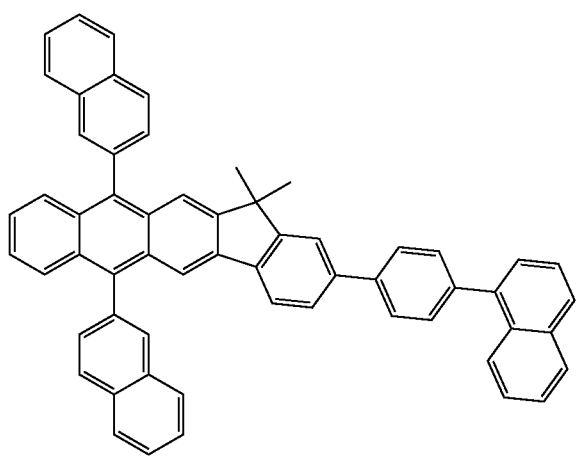
H42
In some embodiments, the host may include at least one of Compounds H43 to H49:
H43
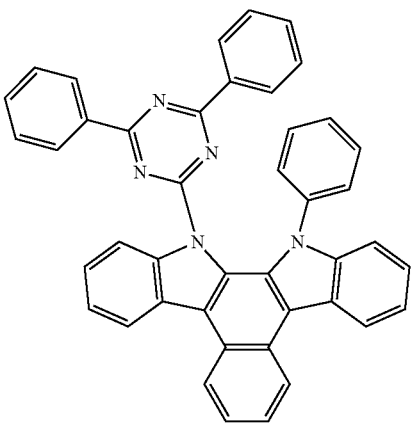
H44
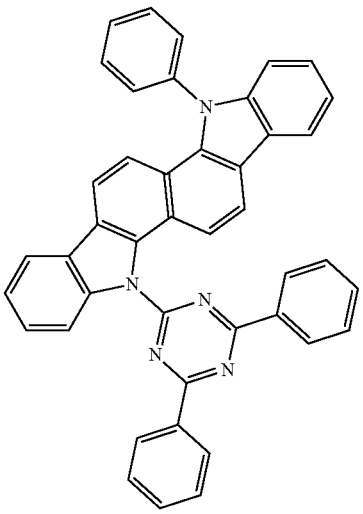
H45
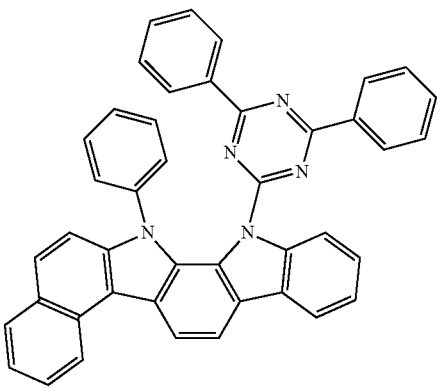

H46

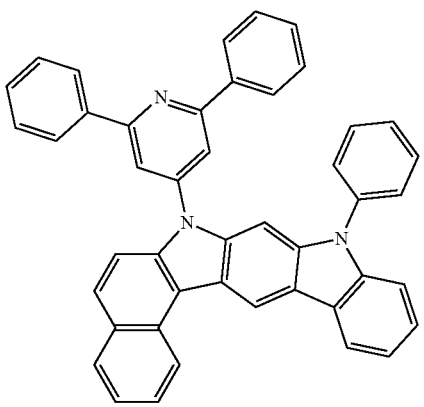

H47

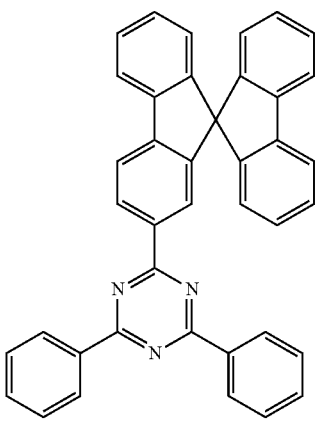

H48

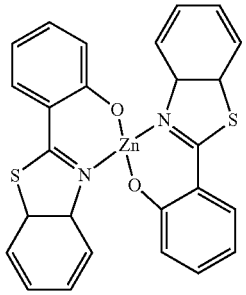

H49

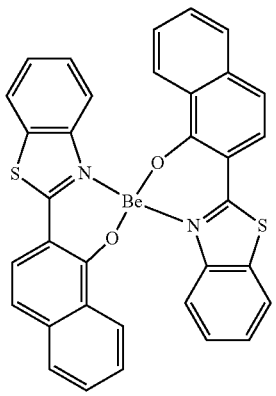

The dopant for the EML may include a phosphorescent dopant or a fluorescent dopant.

The phosphorescent dopant may include an organic metal complex represented by Formula 401:

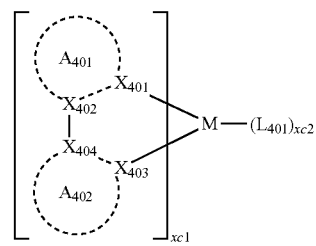

Formula 401

M may be selected from iridium (Ir), platinum (Pt), osmium (Os), titanium (Ti), zirconium (Zr), hafnium (Hf), europium (Eu), terbium (Tb), and thulium (Tm), $X_{401}$ to $X_{404}$ may be each independently a nitrogen or a carbon, the $A_{401}$ and $A_{402}$ rings may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene, at least one of substituents of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isoxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzoimidazole, the substituted benzofuran, the substituted benzothiophene, the substituted isobenzothiophene, the substituted benzoxazole, the substituted isobenzoxazole, the substituted triazole, the substituted oxadiazole, the substituted triazine, the substituted dibenzofuran, and the substituted dibenzothiophene may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{401})(Q_{402})$, —$Si(Q_{403})(Q_{404})(Q_{405})$, and —$B(Q_{406})(Q_{407})$, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{411})(Q_{412})$, —$Si(Q_{413})(Q_{414})(Q_{415})$ and —$B(Q_{416})(Q_{417})$, and —$N(Q_{421})(Q_{422})$, —$Si(Q_{423})(Q_{424})(Q_{425})$, and —$B(Q_{426})(Q_{427})$, $L_{401}$ may be an organic ligand, xc1 may be 1, 2, or 3; and xc2 may be 0, 1, 2, or 3.

For example, $L_{401}$ may be a monovalent, divalent, or trivalent organic ligand. For example, $L_{401}$ may be selected from a halogen ligand (for example, Cl or F), a diketone ligand (for example, acetylacetonate, 1,3-diphenyl-1,3-propanedionate, 2,2,6,6-tetramethyl-3,5-heptanedionate, or hexafluoroacetonate), a carboxylic acid ligand (for example, picolinate, dimethyl-3-pyrazole carboxylate, or benzoate), a carbon monoxide ligand, an isonitrile ligand, a cyano ligand, and a phosphorous ligand (for example, phosphine or phosphite).

For example, $Q_{401}$ to $Q_{407}$, $Q_{411}$ to $Q_{417}$, and $Q_{421}$ to $Q_{427}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group.

When $A_{401}$ in Formula 401 has at least two substituents, the at least two substituents of $A_{401}$ may be linked to each other to form a saturated or unsaturated ring.

When $A_{402}$ in Formula 401 has at least two substituents, the at least two substituents of $A_{402}$ may be linked to each other to form a saturated or unsaturated ring.

When xc1 in Formula 401 is 2 or greater, the plurality of ligands in Formula 401, represented by

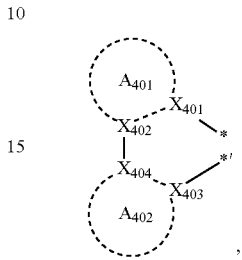

may be identical to or different from each other. When xc1 in Formula 401 is 2 or greater, $A_{401}$ and $A_{402}$ may be linked to $A_{401}$ and $A_{402}$ of another adjacent ligand directly or via a linker (for example, a $C_1$-$C_5$ alkylene group, —N(R')— (where R' is a $C_1$-$C_{10}$ alkyl group or a $C_6$-$C_{20}$ aryl group), or —C(=O)—).

For example, the fluorescent dopant may include a compound represented by Formula 501:

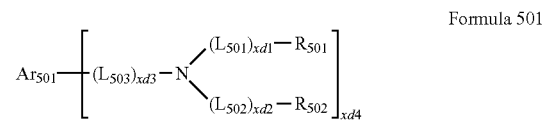

Formula 501

In Formula 501, $Ar_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —$Si(Q_{501})(Q_{502})(Q_{503})$, wherein $Q_{501}$ to $Q_{503}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group;

$L_{501}$ to $L_{503}$ may be defined as described above herein in conjunction with $L_1$;

$R_{501}$ and $R_{502}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may be each independently selected from 0, 1, 2, and 3; and xb4 may be selected from 1, 2, 3, and 4.

For example, the fluorescent host may include at least one of Compounds FD1 to FD9:

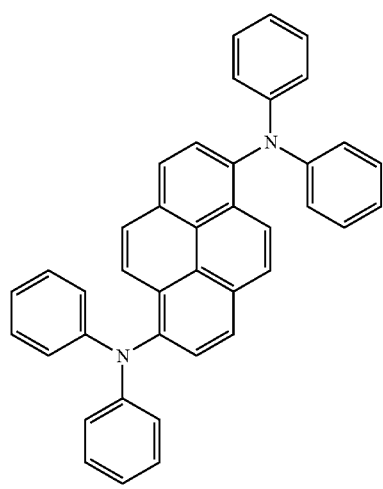

FD1

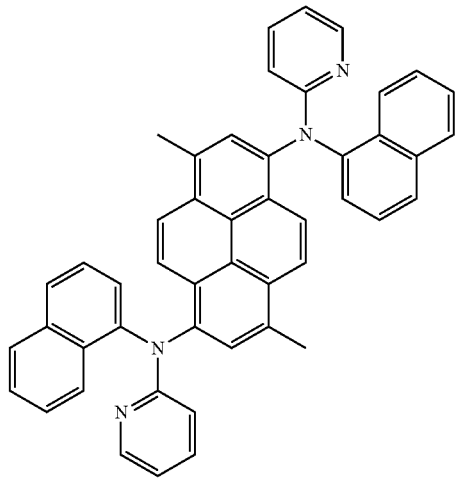

FD2

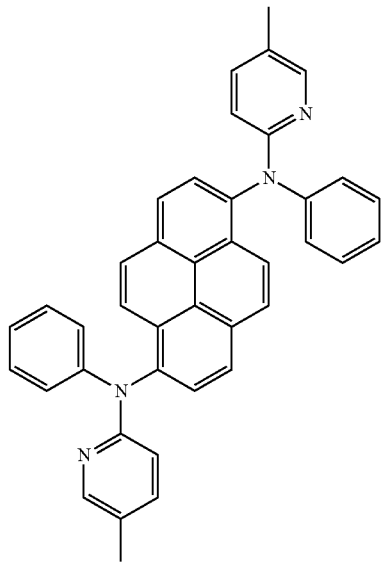

FD3

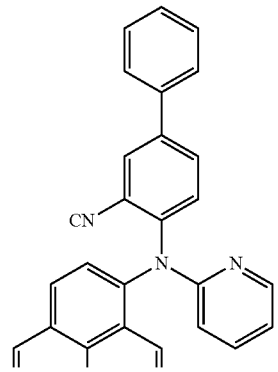

FD4

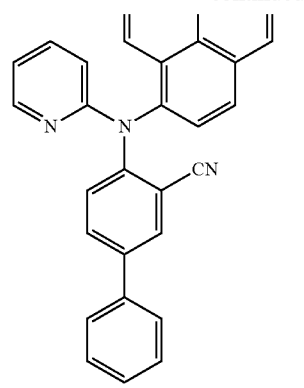

FD5

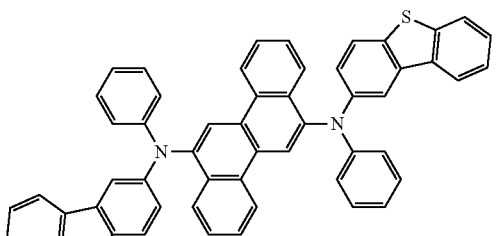

FD8

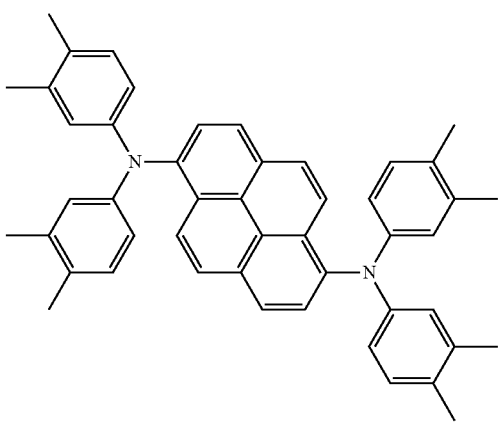

<Compound FD9>

An amount of the dopant in the EML may be from about 0.01 parts to about 15 parts by weight based on 100 parts by weight of the host.

A thickness of the EML may be about 100 Å to about 1,000 Å, and in some embodiments, may be from about 200 Å to about 600 Å. When the thickness of the EML is within these ranges, the EML may have good light emitting ability without a substantial increase in driving voltage.

Next, the electron transport region may be formed on the EML.

The electron transport region may include at least one of a HBL, an ETL, and an EIL. In some embodiments, the electron transport region may have a structure including an ETL/EIL or a HBL/ETL/EIL, wherein the layers forming a structure of the electron transport region may be sequentially stacked on the EML in the order stated above.

In some embodiments, in the organic light-emitting device 10 of FIG. 1, the organic layer 150 may include an electron transport region between the EML and the second electrode 190.

When the electron transport region includes a HBL, the HBL may be formed on the EML by using a suitable method, for example, by using vacuum deposition, spin coating, casting, Langmuir-Blodgett (LB) deposition, inkjet printing, laser printing, laser induced thermal imaging (LITI), or the like. When the HBL is formed using vacuum deposition or spin coating, the deposition and coating conditions for forming the HBL may be similar to the above-described deposition and coating conditions for forming the HIL.

For example, the HBL may include at least one of BCP and Bphen.

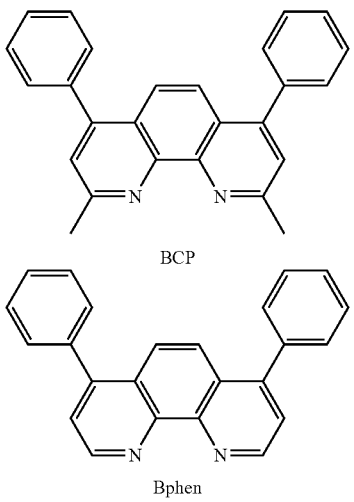

BCP

Bphen

A thickness of the HBL may be from about 20 Å to about 1,000 Å, and in some embodiments, from about 30 Å to about 300 Å. When the thickness of the HBL is within these ranges, the HBL may have improved hole blocking ability without a substantial increase in driving voltage.

The electron transport region may include an ETL. The ETL may be formed on the EML or the HBL by using any of a variety of methods, for example, by using vacuum deposition, spin coating, casting, Langmuir-Blodgett (LB) deposition, inkjet printing, laser printing, laser induced thermal imaging (LITI), or the like. When the ETL is formed using vacuum deposition or spin coating, the deposition and coating conditions for forming the ETL may be similar to the above-described deposition and coating conditions for forming the HIL.

In some embodiments, the ETL may include at least one of a compound represented by Formula 601 and a compound represented by Formula 602:

$$Ar_{601}\text{-}[(L_{601})_{xc1}\text{-}E_{601}]_{xc2} \qquad \text{Formula 601}$$

In Formula 601, $Ar_{601}$ may be selected from a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1\text{-}C_{60}$ alkyl group, a $C_2\text{-}C_{60}$ alkenyl group, a $C_2\text{-}C_{60}$ alkynyl group, a $C_1\text{-}C_{60}$ alkoxy group, a $C_3\text{-}C_{10}$ cycloalkyl group, a $C_1\text{-}C_{10}$ heterocycloalkyl group, a $C_3\text{-}C_{10}$ cycloalkenyl group, a $C_1\text{-}C_{10}$ heterocycloalkenyl group, a $C_6\text{-}C_{60}$ aryl group, a $C_6\text{-}C_{60}$ aryloxy group, a $C_6\text{-}C_{60}$ arylthio group, a $C_1\text{-}C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$), wherein $Q_{301}$ to $Q_{303}$ may be each independently selected from a hydrogen, a $C_1\text{-}C_{60}$ alkyl group, a $C_2\text{-}C_{60}$ alkenyl group, a $C_6\text{-}C_{60}$ aryl group, and a $C_1\text{-}C_{60}$ heteroaryl group:

$L_{601}$ may be defined as described above herein in conjunction with $L_1$;

$E_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1\text{-}C_{20}$ alkyl group, a $C_1\text{-}C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

xe1 may be selected from 0, 1, 2, and 3; and xe2 may be selected from 1, 2, 3, and 4.

Formula 602

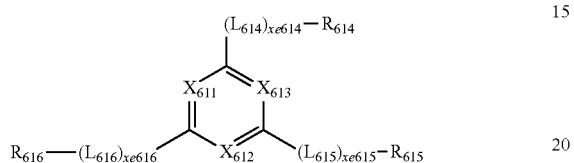

In Formula 602, $X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$, at least one of $X_{611}$ to $X_{613}$ may be N;

$L_{611}$ to $L_{616}$ may be defined as described above in conjunction with $L_1$;

$R_{611}$ to $R_{616}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently selected from, 0, 1, 2, and 3.

The compound of Formula 601 and the compound of Formula 602 may each independently selected from Compounds ET1 to ET15:

ET4
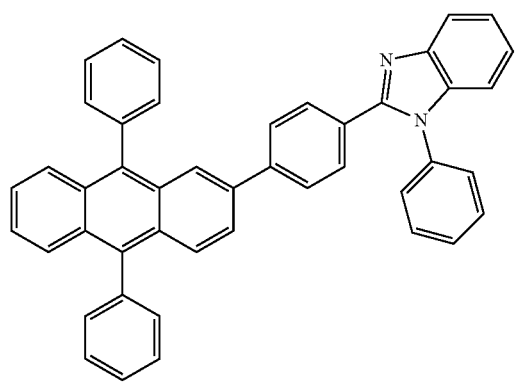
ET5
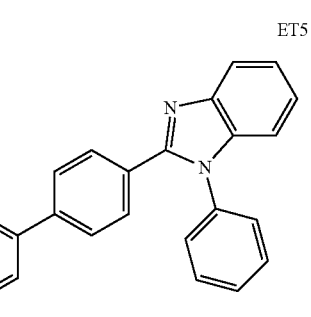
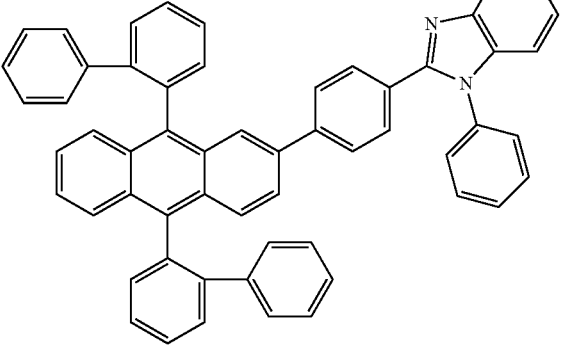
ET6
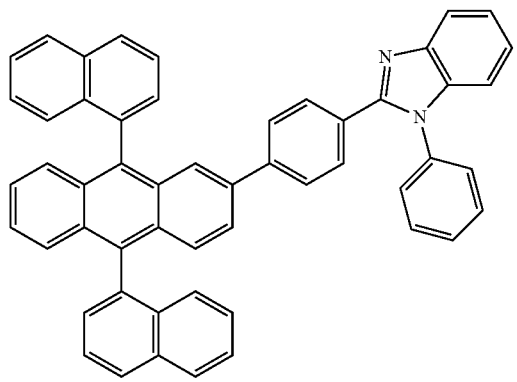
ET7
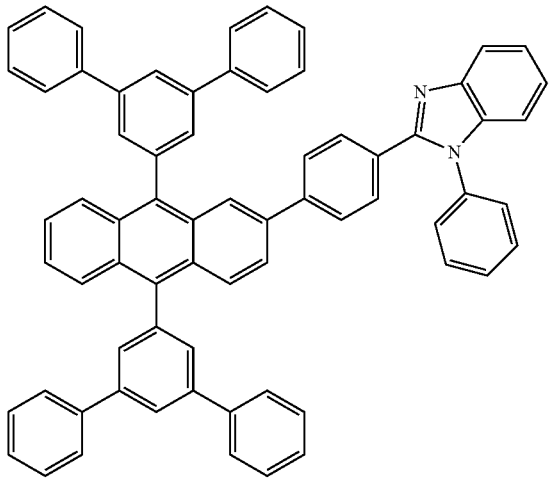
ET8
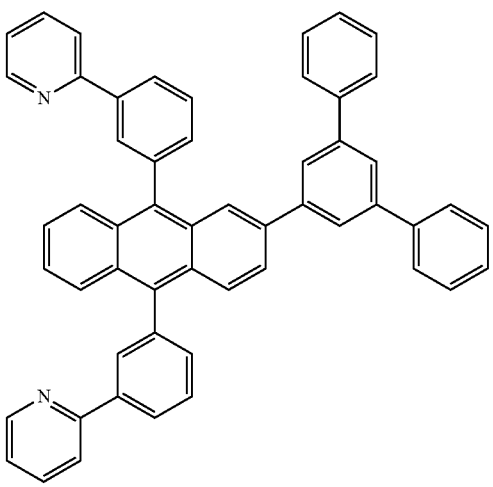
ET9
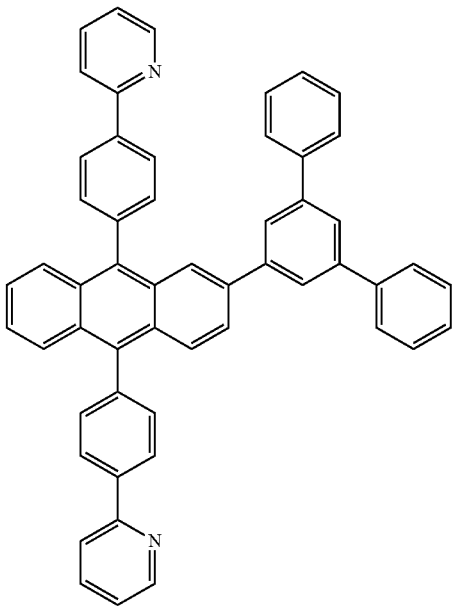

ET10
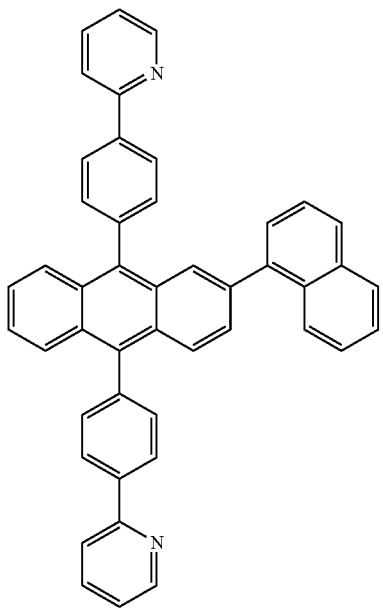
ET11
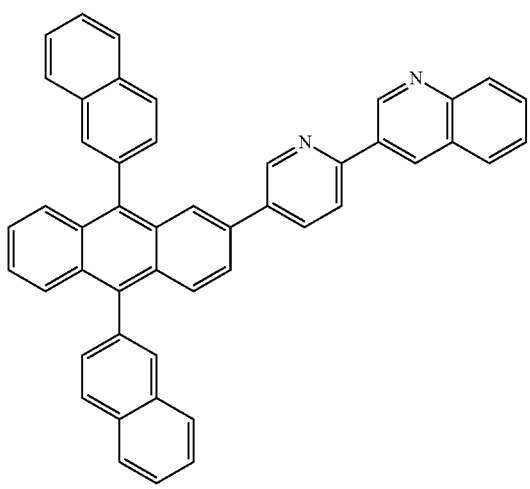
ET12
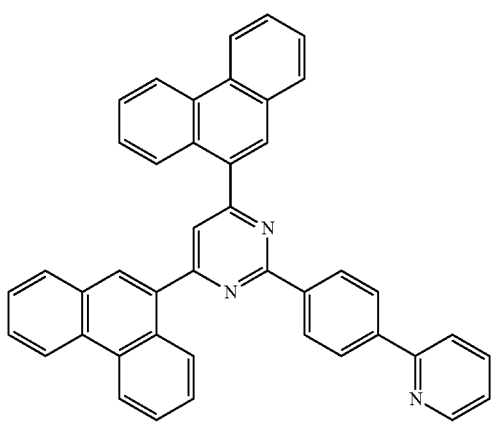
ET13
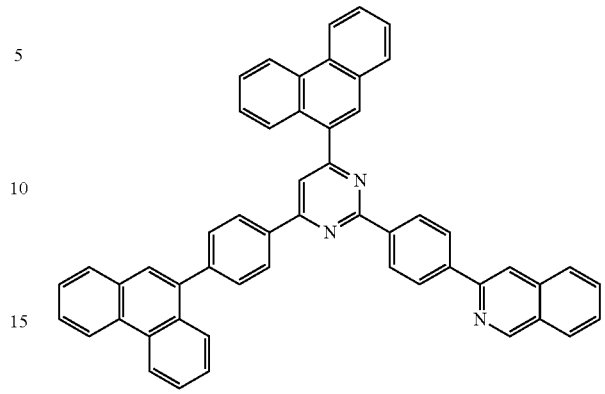
ET14
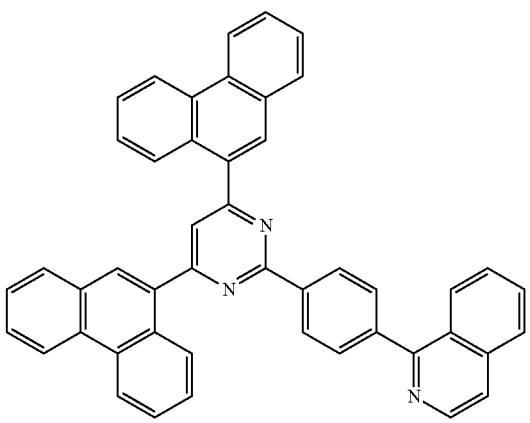
ET15
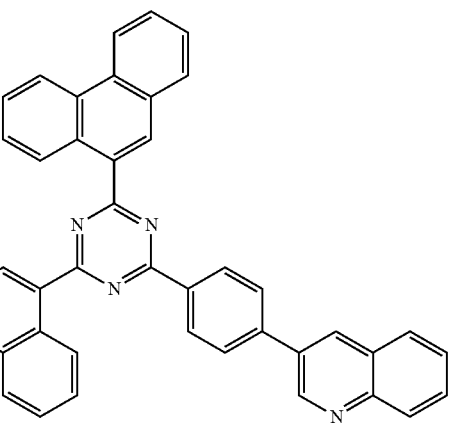
In some embodiments, the ETL may include at least one of BCP, Bphen, Alq$_3$, Balq, TAZ, and NTAZ.

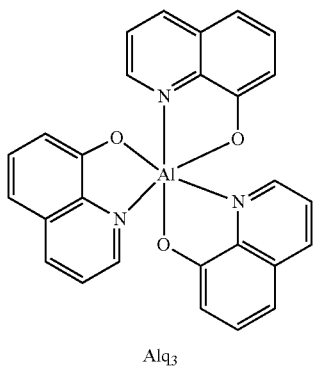

Alq₃

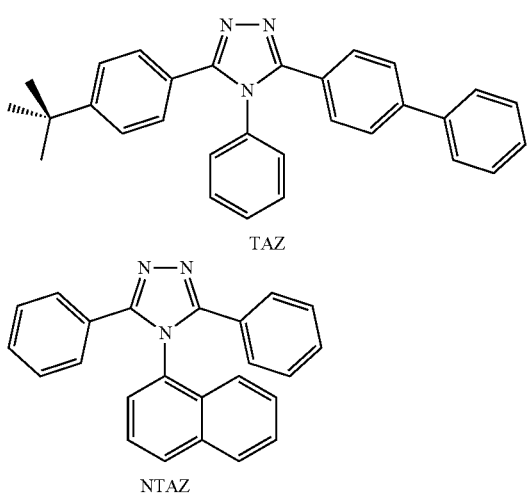

BAlq

TAZ

NTAZ

A thickness of the ETL may be from about 100 Å to about 1,000 Å, and in some embodiments, from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to the above-described materials.

The metal-containing material may include a lithium (Li) complex. Non-limiting examples of the Li complex are compound ET-D1 (lithium quinolate (LiQ)), and compound ET-D2

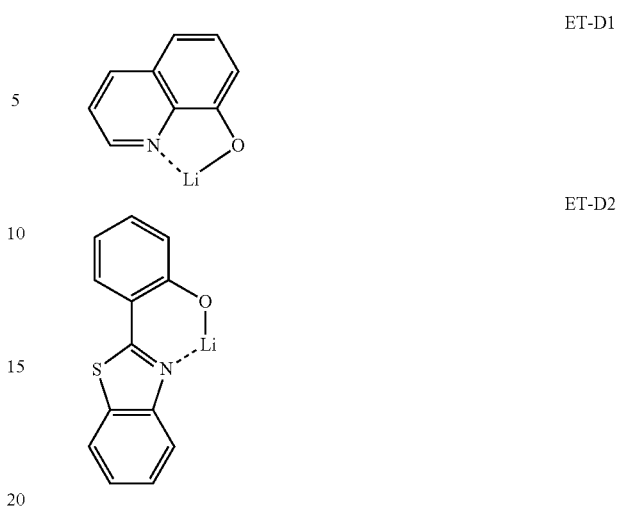

The electron transport region may include an EIL that may facilitate injection of electrons from the second electrode 190.

The EIL may be formed on the ETL by a suitable method, for example, by using vacuum deposition, spin coating, casting, Langmuir-Blodgett (LB) deposition, inkjet printing, laser printing, laser induced thermal imaging (LITI), or the like. When the EIL is formed using vacuum deposition or spin coating, the deposition and coating conditions for forming the EIL may be similar to the above-described deposition and coating conditions for forming the HIL.

The EIL may include at least one selected from LiF, NaCl, CsF, $Li_2O$, BaO, and LiQ.

A thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

The second electrode 190 may be disposed on the organic layer 150, as described above. The second electrode 190 may be a cathode as an electron injecting electrode. A material for forming the second electrode 190 may be a metal, an alloy, an electrically conductive compound, which have a low-work function, or a mixture thereof. Examples of materials for forming the second electrode 190 include lithium (Li), magnesium (Mg), aluminum (Al), aluminum-lithium (Al—Li), calcium (Ca), magnesium-indium (Mg—In), and magnesium-silver (Mg—Ag). In some embodiments, a material for forming the second electrode 190 may be ITO or IZO. The second electrode 190 may be a semi-transmissive electrode or a transmissive electrode.

Figure 2:
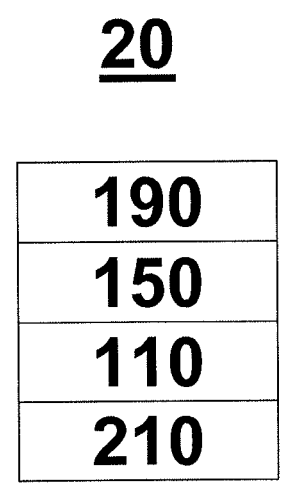
Figure 3:
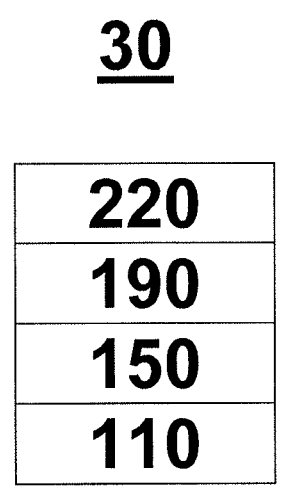
Figure 4:
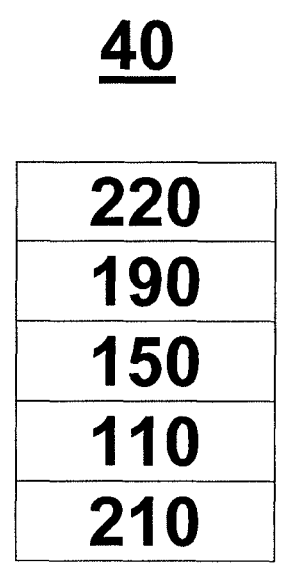

FIGS. 2 to 4 illustrate schematic sectional views of organic light-emitting devices 20, 30, and 40, respectively, according to embodiments of the present disclosure. The organic light-emitting device 20 of FIG. 2 may have a stack structure in which a first capping layer 210, a first electrode 110, an organic layer 150, and a second electrode 190 are sequentially stacked upon one another in the stated order. The organic light-emitting device 30 of FIG. 3 may have a stack structure in which a first electrode 110, an organic layer 150, a second electrode 190, and a second capping layer 220 are sequentially stacked upon one another in the stated order. The organic light-emitting device 40 of FIG. 4 may have a stack structure in which a first capping layer 210, a first electrode 110, an organic layer 150, a second electrode 190, and a second capping layer 220 are sequentially stacked upon one another in the stated order.

In FIGS. 2 to 4, the first electrode 110, the organic layer 150, and the second electrode 190 may be the same as those described above with reference to FIG. 1.

In the organic light-emitting devices 20 and 40, light generated in the emission layer of the organic layer 150 may be extracted from the organic light-emitting device through the first electrode 110, which may be a semi-transmissive or transmissive electrode, and then through the first capping layer 210. In the organic light-emitting devices 30 and 40, light generated in the emission layer of the organic layer 150 may be extracted from the organic light-emitting device through the second electrode 190, which may be a semi-transmissive or transmissive electrode, and then through the second capping layer 220.

The first capping layer 210 and the second capping layer 220 may improve external emission efficiency based on the principle of constructive interference.

The first capping layer 210 of FIG. 2 and the second capping layer 220 of FIG. 3 may include at least one amine-based compound of Formula 1.

In the organic light-emitting device 40 of FIG. 4, at least one of the first capping layer 210 and the second capping layer 220 may include at least one amine-based compound of Formula 1.

In some embodiments, in the organic light-emitting devices 20, 30, and 40 of FIGS. 2 to 4, the organic layer 150 may not include the amine-based compound of Formula 1.

Although the organic light-emitting devices of FIGS. 1 to 4 are described above, other configurations of organic light-emitting devices may include the amine based compound of Formula 1.

As used herein, the term "$C_1$-$C_{60}$ alkyl group" refers to a linear or branched aliphatic hydrocarbon monovalent group having 1 to 60 carbon atoms. Examples of the $C_1$-$C_{60}$ alkyl group include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" refers to a divalent group having the same structure as the $C_1$-$C_{60}$ alkyl.

As used herein, the term "$C_1$-$C_{60}$ alkoxy group" refers to a monovalent group represented by —$OA_{101}$ (where $A_{101}$ is a $C_1$-$C_{60}$ alkyl group, as described above. Examples of the $C_1$-$C_{60}$ alkoxy group include a methoxy group, an ethoxy group, and an isopropyloxy group.

As used herein, the term "$C_2$-$C_{60}$ alkenyl group" refers to a hydrocarbon group including at least one carbon double bond in the middle or terminal of the $C_2$-$C_{60}$ alkyl group. Examples of the $C_2$-$C_{60}$ alkenyl group include an ethenyl group, a propenyl group, and a butenyl group. The term "$C_2$-$C_{60}$ alkylene group" refers to a divalent group having the same structure as the $C_2$-$C_{60}$ alkenyl group.

As used herein, the term "$C_2$-$C_{60}$ alkynyl group" refers to a hydrocarbon group including at least one carbon triple bond in the middle or terminal of the $C_2$-$C_{60}$ alkyl group. Examples of the $C_2$-$C_{60}$ alkynyl group include an ethynyl group, and a propynyl group. The term "$C_2$-$C_{60}$ alkynylene group" used herein refers to a divalent group having the same structure as the $C_2$-$C_{60}$ alkynyl group.

As used herein, the term "$C_3$-$C_{10}$ cycloalkyl group" refers to a monovalent, monocyclic hydrocarbon group having 3 to 10 carbon atoms. Examples of the $C_3$-$C_{10}$ cycloalkyl group include a cyclopropyl group, a cyclobutyl group, a cyclopentyl group, a cyclohexyl group, and a cycloheptyl group.

The term "$C_3$-$C_{10}$ cycloalkylene group" refers to a divalent group having the same structure as the $C_3$-$C_{10}$ cycloalkyl group.

As used herein, the term "$C_1$-$C_{10}$ heterocycloalkyl group" refers to a monovalent monocyclic group having 1 to 10 carbon atoms in which at least one hetero atom selected from N, O, Si, P, and S is included as a ring-forming atom. Examples of the $C_1$-$C_{10}$ heterocycloalkyl group include a tetrahydrofuranyl group, and a tetrahydrothiophenyl group. The term "$C_1$-$C_{10}$ heterocycloalkylene group" refers to a divalent group having the same structure as the $C_1$-$C_{10}$ heterocycloalkyl group.

As used herein, the term "$C_3$-$C_{10}$ cycloalkenyl group" refers to a monovalent monocyclic group having 3 to 10 carbon atoms that includes at least one double bond in the ring but does not have aromaticity. Examples of the $C_3$-$C_{10}$ cycloalkenyl group include a cyclopentenyl group, a cyclohexenyl group, and a cycloheptenyl group. The term "$C_3$-$C_{10}$ cycloalkenylene group" refers to a divalent group having the same structure as the $C_3$-$C_{10}$ cycloalkenyl group.

As used herein, the term "$C_1$-$C_{10}$ heterocycloalkenyl group" used herein refers to a monovalent monocyclic group having 1 to 10 carbon atoms that includes at least one double bond in the ring and in which at least one hetero atom selected from N, O, Si, P, and S is included as a ring-forming atom. Examples of the $C_1$-$C_{10}$ heterocycloalkenyl group include a 2,3-hydrofuranyl group, and a 2,3-hydrothiophenyl group. The term "$C_1$-$C_{10}$ heterocycloalkenylene group" used herein refers to a divalent group having the same structure as the $C_1$-$C_{10}$ heterocycloalkenyl group.

As used herein, the term "$C_6$-$C_{60}$ aryl group" refers to a monovalent, aromatic carbocyclic aromatic group having 6 to 60 carbon atoms. The term "$C_6$-$C_{60}$ arylene group" refers to a divalent, aromatic carbocyclic group having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group, and the $C_6$-$C_{60}$ arylene group include at least two rings, the rings may be fused to each other.

As used herein, the term "$C_1$-$C_{60}$ heteroaryl group" refers to a monovalent, aromatic carbocyclic aromatic group in which at least one hetero atom selected from N, O, Si, P, and S is included as a ring-forming atom, and 1 to 60 carbon atoms. The term "$C_1$-$C_{60}$ heteroarylene group" refers to a divalent, aromatic carbocyclic group in which at least one hetero atom selected from N, O, Si, P, and S is included as a ring-forming atom, and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group include at least two rings, the rings may be fused to each other.

As used herein, the term "$C_6$-$C_{60}$ aryloxy group" indicates —$OA_{102}$ (where $A_{102}$ is a $C_6$-$C_{60}$ aryl group, as described above), and a $C_6$-$C_{60}$ arylthio group indicates —$SA_{103}$ (where $A_{103}$ is a $C_6$-$C_{60}$ aryl group, as described above).

As used herein, the term "monovalent non-aromatic condensed polycyclic group" (including, for example, 8 to 60 carbon atoms) refers to a monovalent group that includes at least two rings condensed to each other and includes only carbon atoms as ring-forming atoms and that represents non-aromaticity as a whole. An example of the monovalent non-aromatic condensed polycyclic group is a fluorenyl group. As used herein, the term "divalent non-aromatic condensed polycyclic group" refers to a divalent group with the same structure as the monovalent non-aromatic condensed polycyclic group.

As used herein, the term "monovalent non-aromatic condensed heteropolycyclic group" (including, for example, 1 to 60 carbon atoms) refers to a monovalent group that includes at least two rings condensed to each other and includes carbon and hetero atoms selected from N, O, Si, P and S as ring-forming atoms and that represents non-aromaticity as a whole. An example of the monovalent non-aromatic condensed heteropolycyclic group is a carbazolyl group. As used herein, the term "divalent non-aromatic condensed heteropolycyclic group" refers to a divalent group with the same structure as the monovalent non-aromatic condensed polycyclic group.

As used herein, at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group.

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{10}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$) and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$ and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

The acronym "Ph" used herein refers to phenyl, the acronym "Me" used herein refers to methyl, the acronym "Et" used herein refers to ethyl, and the acronym "ter-Bu" or "Bu'" used herein refers to tert-butyl.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples. In the following synthesis examples, the expression that "'B' instead of 'A' was used" indicates that the amounts of 'B' and 'A' were the same in equivalent amounts.

EXAMPLE

Synthesis Example 1: Synthesis of Compound 3

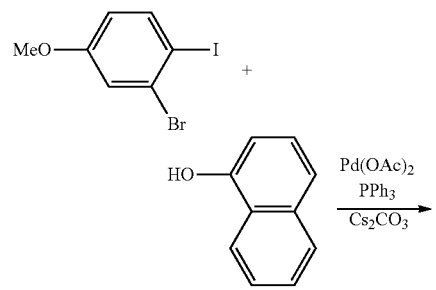

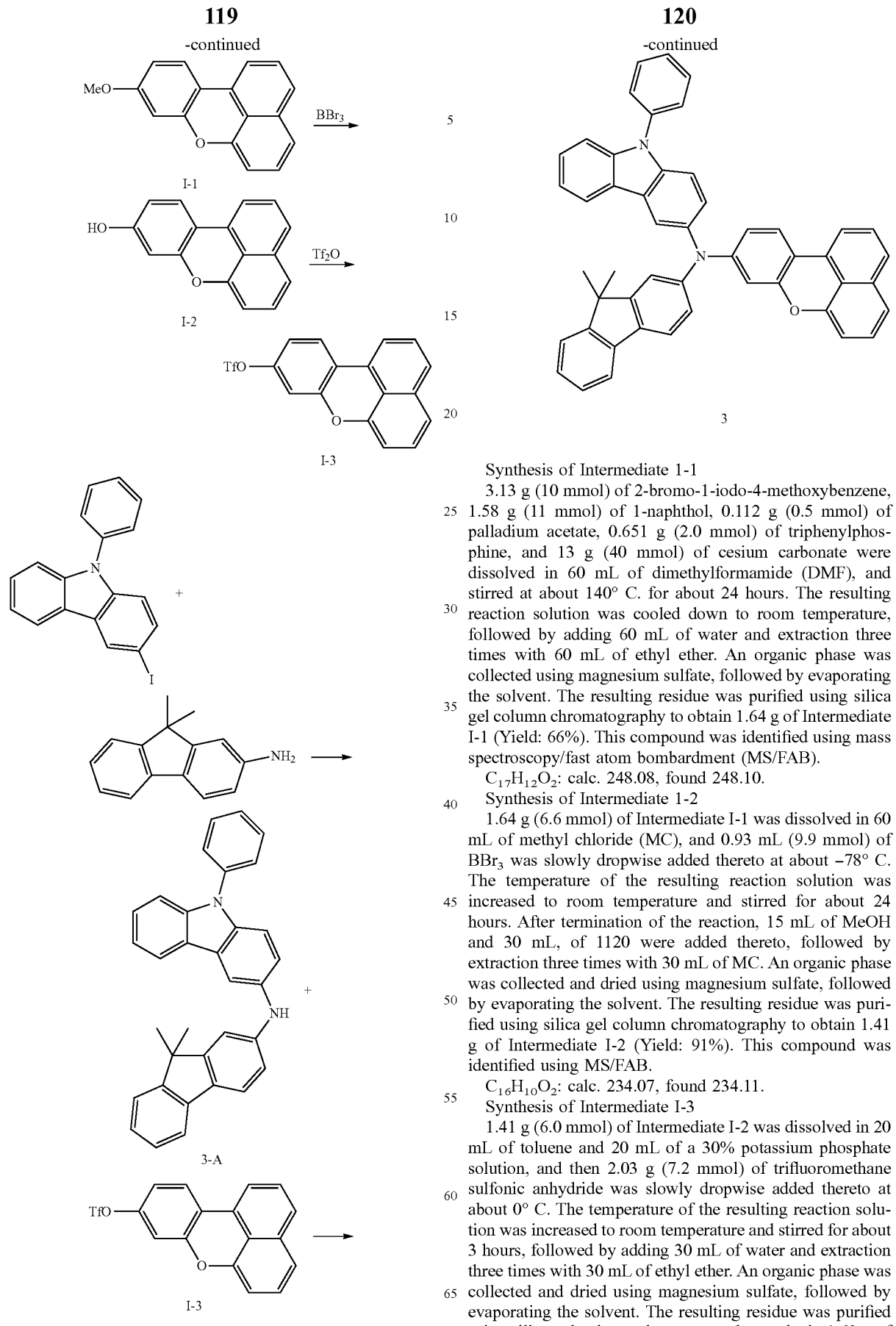

Synthesis of Intermediate 1-1

3.13 g (10 mmol) of 2-bromo-1-iodo-4-methoxybenzene, 1.58 g (11 mmol) of 1-naphthol, 0.112 g (0.5 mmol) of palladium acetate, 0.651 g (2.0 mmol) of triphenylphosphine, and 13 g (40 mmol) of cesium carbonate were dissolved in 60 mL of dimethylformamide (DMF), and stirred at about 140° C. for about 24 hours. The resulting reaction solution was cooled down to room temperature, followed by adding 60 mL of water and extraction three times with 60 mL of ethyl ether. An organic phase was collected using magnesium sulfate, followed by evaporating the solvent. The resulting residue was purified using silica gel column chromatography to obtain 1.64 g of Intermediate I-1 (Yield: 66%). This compound was identified using mass spectroscopy/fast atom bombardment (MS/FAB).

$C_{17}H_{12}O_2$: calc. 248.08, found 248.10.

Synthesis of Intermediate 1-2

1.64 g (6.6 mmol) of Intermediate I-1 was dissolved in 60 mL of methyl chloride (MC), and 0.93 mL (9.9 mmol) of BBr$_3$ was slowly dropwise added thereto at about −78° C. The temperature of the resulting reaction solution was increased to room temperature and stirred for about 24 hours. After termination of the reaction, 15 mL of MeOH and 30 mL, of 1120 were added thereto, followed by extraction three times with 30 mL of MC. An organic phase was collected and dried using magnesium sulfate, followed by evaporating the solvent. The resulting residue was purified using silica gel column chromatography to obtain 1.41 g of Intermediate I-2 (Yield: 91%). This compound was identified using MS/FAB.

$C_{16}H_{10}O_2$: calc. 234.07, found 234.11.

Synthesis of Intermediate I-3

1.41 g (6.0 mmol) of Intermediate I-2 was dissolved in 20 mL of toluene and 20 mL of a 30% potassium phosphate solution, and then 2.03 g (7.2 mmol) of trifluoromethane sulfonic anhydride was slowly dropwise added thereto at about 0° C. The temperature of the resulting reaction solution was increased to room temperature and stirred for about 3 hours, followed by adding 30 mL of water and extraction three times with 30 mL of ethyl ether. An organic phase was collected and dried using magnesium sulfate, followed by evaporating the solvent. The resulting residue was purified using silica gel column chromatography to obtain 1.63 g of Intermediate I-3 (Yield: 81%). This compound was identified using MS/FAB.

$C_{17}H_9F_3O_4S$: calc. 336.02, found 336.0.

Synthesis of Intermediate 3-A 7.38 g (20.0 mmol) of 3-iodo-9-phenyl-9H-carbazole, 6.27 g (30.0 mmol) of 9,9-dimethyl-9H-fluorene-2-amine, 0.37 g (0.4 mmol) of $Pd_2(dba)_3$, 0.08 g (0.4 mmol) of $PtBu_3$, and 2.88 g (30.0 mmol) of KOtBu were dissolved in 60 mL of toluene and then stirred at about 85° C. for about 4 hours. The resulting reaction solution was cooled down to room temperature, followed by adding 50 mL of water and extraction three times with 50 mL of diethyl ether. An organic phase was collected and dried using magnesium sulfate, followed by evaporating the solvent. The resulting residue was purified using silica gel column chromatography to obtain 7.92 g of Intermediate 3-A (Yield: 88%). This compound was identified using MS/FAB.

$C_{33}H_{26}N_2$: calc. 450.20, found 450.22.

Synthesis of Compound 3

6.75 g (15.0 mmol) of Intermediate 3-A, 5.04 g (15.0 mmol) of Intermediate I-3, 0.18 g (0.2 mmol) of $Pd_2(dba)_3$, 0.04 g (0.4 mmol) of $PtBu_3$, and 1.44 g (15.0 mmol) of KOtBu were dissolved in 80 mL of toluene, and then stirred at about 85° C. for about 4 hours. The resulting reaction solution was cooled down to room temperature, followed by adding 50 mL of water and extraction three times with 50 mL of diethyl ether. An organic phase was collected and dried using magnesium sulfate, followed by evaporating the solvent. The resulting residue was purified using silica gel column chromatography to obtain 8.19 g of Compound 3 (Yield: 82%). This compound was identified using MS/FAB and $^1$H nuclear magnetic resonance spectroscopy (NMR).

$C_{49}H_{34}N_2O$: calc. 666.82, found 666.85.

Synthesis Example 2: Synthesis of Compound 21

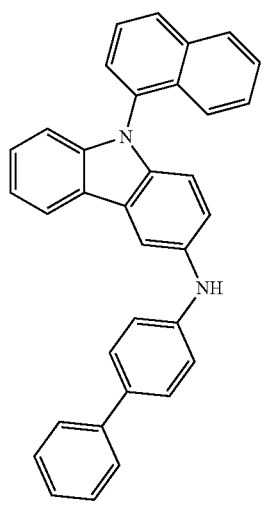

21-A

Compound 21 was synthesized in the same manner as in Synthesis Example 1, except that Intermediate 21-A, instead of Intermediate 3-A used in the synthesis of Compound 3 in Synthesis Example 1, was used. This compound was identified using MS/FAB and $^1$H NMR.

$C_{50}H_{32}N_2O$: calc. 676.81, found 676.86.

Synthesis Example 3: Synthesis of Compound 29

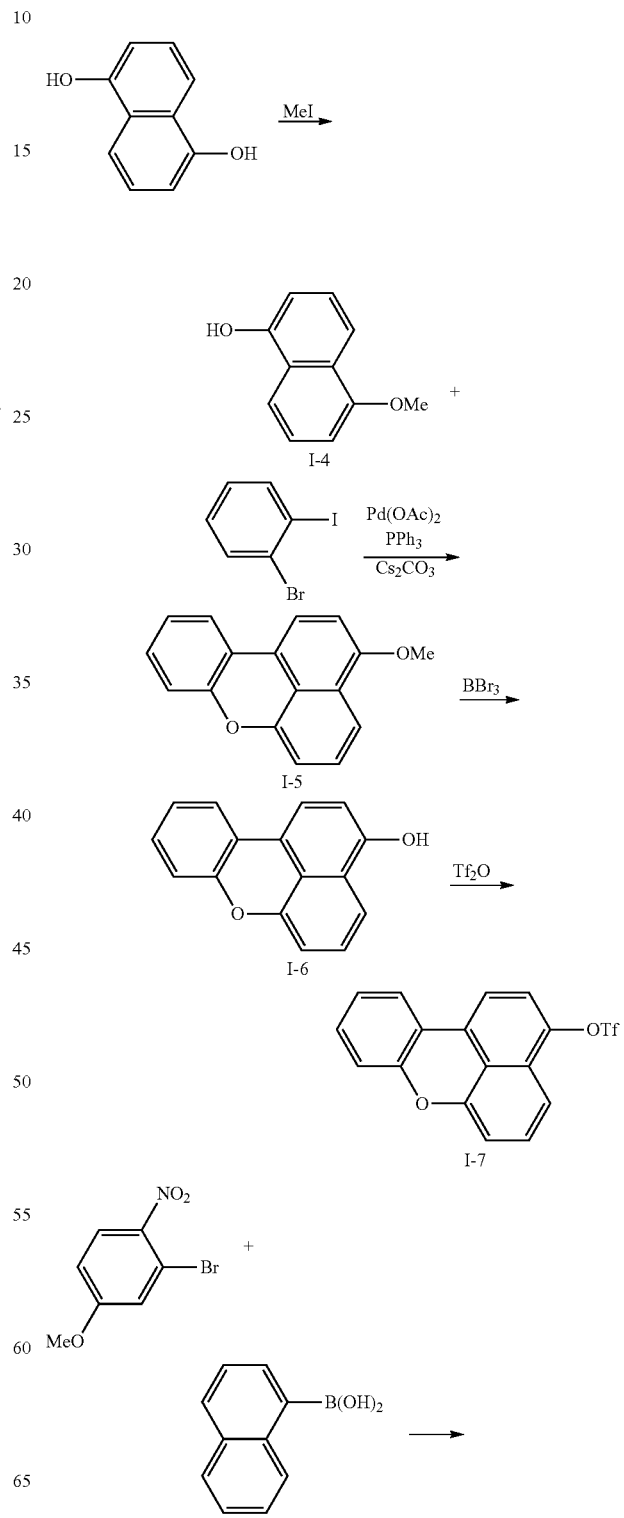

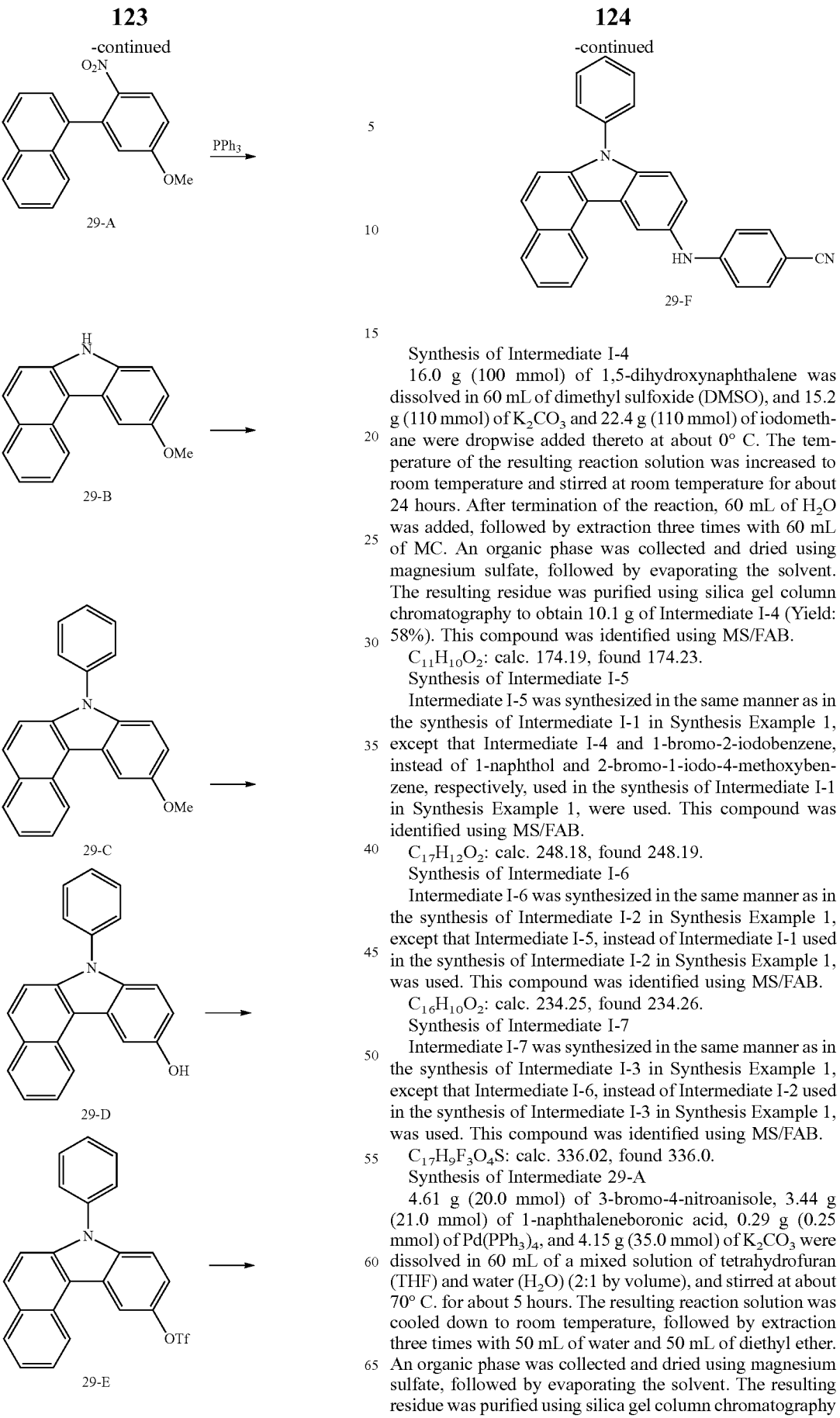

Synthesis of Intermediate I-4

16.0 g (100 mmol) of 1,5-dihydroxynaphthalene was dissolved in 60 mL of dimethyl sulfoxide (DMSO), and 15.2 g (110 mmol) of $K_2CO_3$ and 22.4 g (110 mmol) of iodomethane were dropwise added thereto at about 0° C. The temperature of the resulting reaction solution was increased to room temperature and stirred at room temperature for about 24 hours. After termination of the reaction, 60 mL of $H_2O$ was added, followed by extraction three times with 60 mL of MC. An organic phase was collected and dried using magnesium sulfate, followed by evaporating the solvent. The resulting residue was purified using silica gel column chromatography to obtain 10.1 g of Intermediate I-4 (Yield: 58%). This compound was identified using MS/FAB.

$C_{11}H_{10}O_2$: calc. 174.19, found 174.23.

Synthesis of Intermediate I-5

Intermediate I-5 was synthesized in the same manner as in the synthesis of Intermediate I-1 in Synthesis Example 1, except that Intermediate I-4 and 1-bromo-2-iodobenzene, instead of 1-naphthol and 2-bromo-1-iodo-4-methoxybenzene, respectively, used in the synthesis of Intermediate I-1 in Synthesis Example 1, were used. This compound was identified using MS/FAB.

$C_{17}H_{12}O_2$: calc. 248.18, found 248.19.

Synthesis of Intermediate I-6

Intermediate I-6 was synthesized in the same manner as in the synthesis of Intermediate I-2 in Synthesis Example 1, except that Intermediate I-5, instead of Intermediate I-1 used in the synthesis of Intermediate I-2 in Synthesis Example 1, was used. This compound was identified using MS/FAB.

$C_{16}H_{10}O_2$: calc. 234.25, found 234.26.

Synthesis of Intermediate I-7

Intermediate I-7 was synthesized in the same manner as in the synthesis of Intermediate I-3 in Synthesis Example 1, except that Intermediate I-6, instead of Intermediate I-2 used in the synthesis of Intermediate I-3 in Synthesis Example 1, was used. This compound was identified using MS/FAB.

$C_{17}H_9F_3O_4S$: calc. 336.02, found 336.0.

Synthesis of Intermediate 29-A 4.61 g (20.0 mmol) of 3-bromo-4-nitroanisole, 3.44 g (21.0 mmol) of 1-naphthaleneboronic acid, 0.29 g (0.25 mmol) of $Pd(PPh_3)_4$, and 4.15 g (35.0 mmol) of $K_2CO_3$ were dissolved in 60 mL of a mixed solution of tetrahydrofuran (THF) and water ($H_2O$) (2:1 by volume), and stirred at about 70° C. for about 5 hours. The resulting reaction solution was cooled down to room temperature, followed by extraction three times with 50 mL of water and 50 mL of diethyl ether. An organic phase was collected and dried using magnesium sulfate, followed by evaporating the solvent. The resulting residue was purified using silica gel column chromatography to obtain 4.91 g of Intermediate 29-A (Yield: 88%). This compound was identified using MS/FAB.

$C_{17}H_{13}NO_3$: calc. 279.29, found 279.30.

Synthesis of Intermediate 29-B 200 mL of 1,2-dichlorobenzene was dissolved in 4.91 g (17.5 mmol) of Intermediate 29-A, and 6.89 g (26.3 mmol) of triphenylphosphine was added thereto and stirred at about 150° C. for about 12 hours. The resulting reaction solution was cooled down to room temperature and followed by evaporating the solvent. The resulting residue was purified using silica gel column chromatography to obtain 3.50 g of Intermediate 29-B (Yield: 81%). This compound was identified using MS/FAB.

$C_{17}H_{13}NO$: calc. 247.29, found 247.31.

Synthesis of Intermediate 29-C 3.50 g (14.2 mmol) of Intermediate 29-B, 5.77 g (28.3 mmol) of iodobenzene, 270 mg (0.142 mmol) of CuI, 5.89 g (42.6 mmol) of $K_2CO_3$, and 75 mg (0.28 mmol) of 18-Crown-6 ether were dissolved in 100 mL of 1,2-dichlorobenzene and stirred at about 150° C. for about 12 hours. The resulting reaction solution was cooled down to room temperature and followed by evaporating the solvent. The resulting residue was purified using silica gel column chromatography to obtain 3.62 g of Intermediate 29-C(Yield: 79%). This compound was identified using MS/FAB.

$C_{23}H_{17}NO$: calc. 323.39, found 323.40.

Synthesis of Intermediate 29-D

Intermediate 29-D was synthesized in the same manner as in the synthesis of Intermediate I-2 in Synthesis Example 1, except that Intermediate 29-C, instead of Intermediate I-1 used in the synthesis of Intermediate I-2 in Synthesis Example 1, was used. This compound was identified using MS/FAB.

$C_{22}H_{15}NO$: calc. 309.36, found 309.38.

Synthesis of Intermediate 29-E

Intermediate 29-E was synthesized in the same manner as in the synthesis of Intermediate I-3 in Synthesis Example 1, except that Intermediate 29-D, instead of Intermediate I-2 used in the synthesis of Intermediate I-3 in Synthesis Example 1, was used. This compound was identified using MS/FAB.

$C_{23}H_{14}F_3NO_3S$: calc. 441.42, found 441.44.

Synthesis of Intermediate 29-F

Intermediate 29-F was synthesized in the same manner as in the synthesis of Compound 3 in Synthesis Example 1, except that 4-aminobenzonitrile and Intermediate 29-E, respectively, instead of Intermediate 3-A and Intermediate I-3 used in the synthesis of Compound 3 in Synthesis Example 1, were used. This compound was identified using MS/FAB.

$C_{29}H_{19}N_3$: calc. 409.49, found 409.51.

Synthesis of Compound 29

Compound 29 was synthesized in the same manner as in the synthesis of Compound 3 in Synthesis Example 1, except that Intermediate 29-F and Intermediate I-7, respectively, instead of Intermediate 3-A and Intermediate I-3 used in the synthesis of Compound 3 in Synthesis Example 1, were used. This compound was identified using MS/FAB and $^1$H NMR.

$C_{45}H_{27}N_3O$: calc. 625.73, found 625.76.

Synthesis Example 4: Synthesis of Compound 40

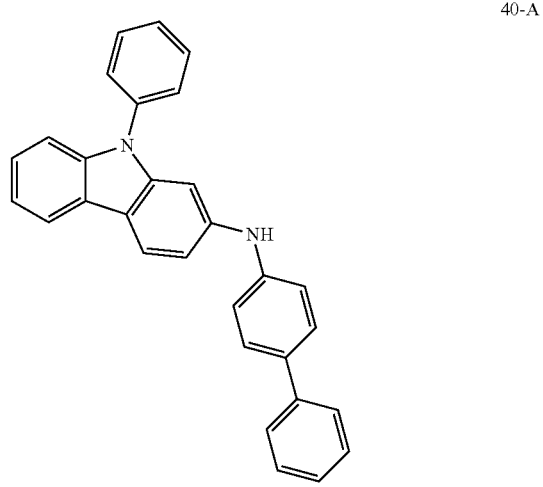 [SMILES: c1ccc(-c2ccc(Nc3ccc4c5ccccc5n(-c5ccccc5)c4c3)cc2)cc1]

40-A

Compound 40 was synthesized in the same manner as in the synthesis of Compound 3 in Synthesis Example 1, except that Intermediate 40-A, instead of Intermediate 3-A used in the synthesis of Compound 3 in Synthesis Example 1, was used. This compound was identified using MS/FAB and $^1$H NMR.

$C_{46}H_{30}N_2O$: calc. 626.23, found 626.26.

Synthesis Example 5: Synthesis of Compound 49

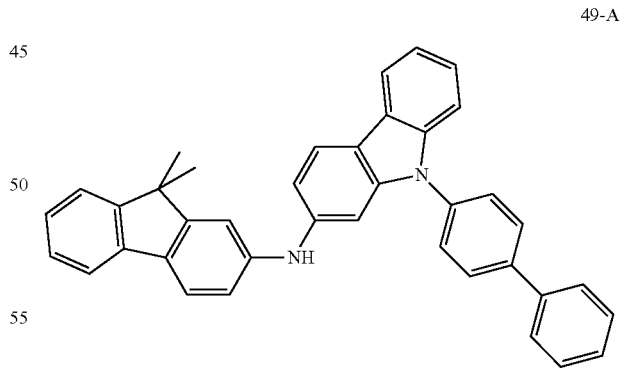

49-A

Compound 49 was synthesized in the same manner as in the synthesis of Compound 3 in Synthesis Example 1, except that Intermediate I-7 and Intermediate 49-A, respectively, instead of Intermediate I-3 and Intermediate 3-A used in the synthesis of Compound 3 in Synthesis Example 1, were used. This compound was identified using MS/FAB and $^1$H NMR.

$C_{55}H_{38}N_2O$: calc. 742.92, found 742.94.

Synthesis Example 6: Synthesis of Compound 56

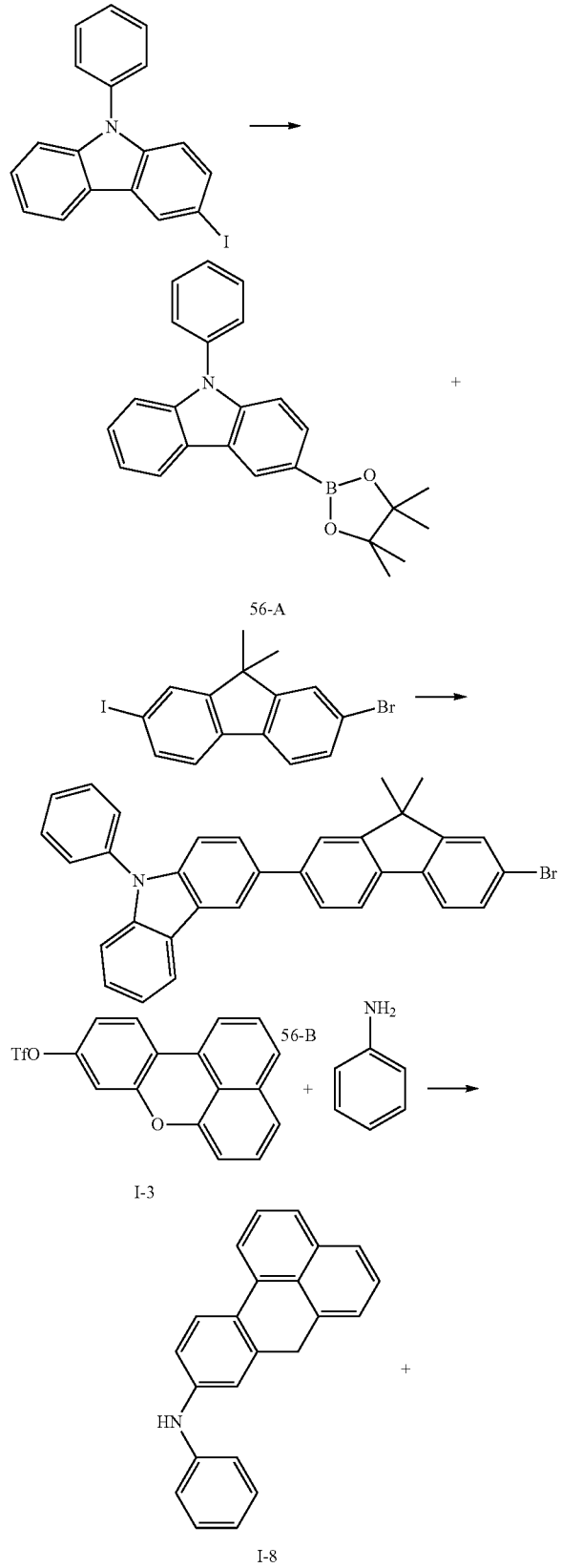

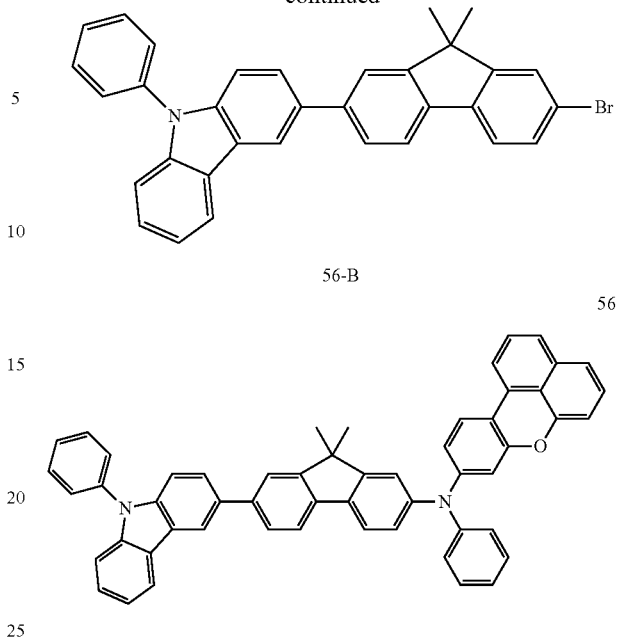

56-B

56

Synthesis of Intermediate 56-A 3.69 g (10.0 mmol) of 3-iodo-9-phenyl-9H-carbazole, 2.54 g (10.0 mmol) of bis(pinacolato)diborone, 0.36 g (0.5 mmol) of $PdCl_2(dppf)_2$, and 2.94 g (30.0 mmol) of KOAc were dissolved in 40 mL of DMSO, and stirred at about 80° C. for about 6 hours. The resulting reaction solution was cooled down to room temperature, followed by adding 50 mL of water and extraction three times with 50 mL of diethyl ether. An organic phase was collected and dried using magnesium sulfate, followed by evaporating the solvent. The resulting residue was purified using silica gel column chromatography to obtain 3.37 g of Intermediate 56-A (Yield: 80%). This compound was identified using MS/FAB.

$C_{24}H_{24}BNO_2$: calc. 369.27, found 369.29.

Synthesis of Intermediate 56-B 2.11 g (5.0 mmol) of Intermediate 56-A, 0.91 g (5.0 mmol) of 2-bromo-7-iodo-9,9-dimethyl-9H-fluorene, 0.29 g (0.25 mmol) of $Pd(PPh_3)_4$, and 2.07 g (15.0 mmol) of $K_2CO_3$ were dissolved in 60 mL of a mixed solution of THF and $H_2O$ (2:1 by volume) and stirred at about 70° C. for about 5 hours. The resulting reaction solution was cooled down to room temperature, followed by adding 50 mL of water and extraction three times with 50 mL of diethyl ether. An organic phase was collected and dried using magnesium sulfate, followed by evaporating the solvent. The resulting residue was purified using silica gel column chromatography to obtain 1.71 g of Intermediate 56-B (Yield: 86%). This compound was identified using MS/FAB $C_{33}H_{24}BrN$: calc. 514.46, found 514.48.

Synthesis of Intermediate I-8

Intermediate I-8 was synthesized in the same manner as in the synthesis of Compound 3 in Synthesis Example 1, except that aniline, instead of Intermediate 3-A used in the synthesis of Compound 3 in Synthesis Example 1, was used. This compound was identified using MS/FAB.

$C_{22}H_{15}NO$: calc. 309.36, found 309.38.

Synthesis of Compound 56

Compound 56 was synthesized in the same manner as in the synthesis of Compound 3 in Synthesis Example 1, except that Intermediate 56-B and Intermediate I-8, respectively, instead of Intermediate I-3 and Intermediate 3-A used in the synthesis of Compound 3 in Synthesis Example 1, were used. This compound was identified using MS/FAB and $^1$H-NMR.

$C_{55}H_{38}N_2O$: calc. 742.29, found 742.31.

Synthesis Example 7: Synthesis of Compound 57

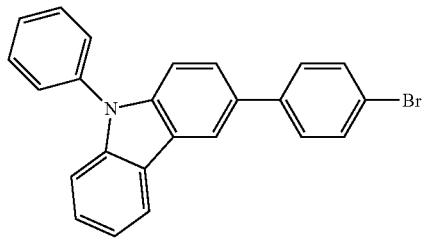

57-A

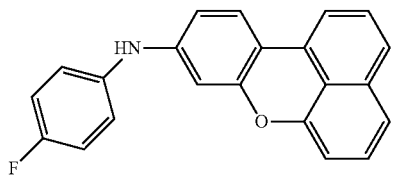

I-9

Compound 57 was synthesized in the same manner as in the synthesis of Compound 3 in Synthesis Example 1, except that Intermediate 57-A and Intermediate I-9, respectively, instead of Intermediate I-3 and Intermediate 3-A used in the synthesis of Compound 3 in Synthesis Example 1, were used. This compound was identified using MS/FAB and $^1$H NMR.

$C_{46}H_{29}FN_2O$: calc. 644.74, found 644.76.

Synthesis Example 8: Synthesis of Compound 59

I-10

Compound 59 was synthesized in the same manner as in the synthesis of Compound 3 in Synthesis Example 1, except that Intermediate 57-A and Intermediate I-10, respectively, instead of Intermediate I-3 and Intermediate 3-A used in the synthesis of Compound 3 in Synthesis Example 1, were used. This compound was identified using MS/FAB and $^1$H NMR.

$C_{52}H_{34}N_2O$: calc. 702.85, found 702.87.

Synthesis Example 9: Synthesis of Compound 62

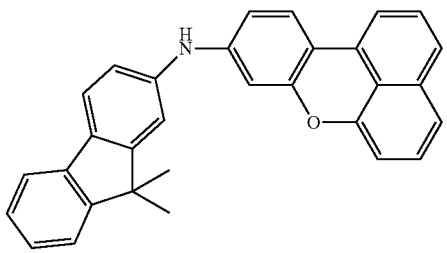

I-11

Compound 62 was synthesized in the same manner as in the synthesis of Compound 3 in Synthesis Example 1, except that Intermediate 57-A and Intermediate I-11, respectively, instead of Intermediate I-3 and Intermediate 3-A used in the synthesis of Compound 3 in Synthesis Example 1, were used. This compound was identified using MS/FAB and $^1$H NMR.

$C_{55}H_{38}N_2O$: calc. 742.92, found 742.93.

Synthesis Example 10: Synthesis of Compound 63

I-12

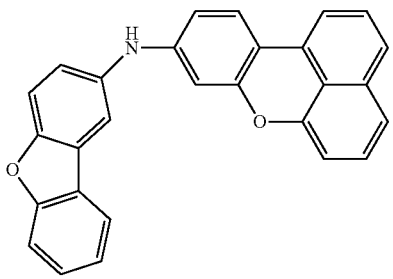

Compound 63 was synthesized in the same manner as in the synthesis of Compound 3 in Synthesis Example 1, except that Intermediate 57-A and Intermediate I-12, respectively, instead of Intermediate I-3 and Intermediate 3-A used in the synthesis of Compound 3 in Synthesis Example 1, were used. This compound was identified using MS/FAB and $^1$H NMR.

$C_{52}H_{32}N_2O_2$: calc. 716.84, found 716.86.

Synthesis Example 11: Synthesis of Compound 70

70-A

Compound 70 was synthesized in the same manner as in the synthesis of Compound 3 in Synthesis Example 1, except that Intermediate 70-A and Intermediate I-11, respectively, instead of Intermediate I-3 and Intermediate 3-A used in the synthesis of Compound 3 in Synthesis Example 1, were used. This compound was identified using MS/FAB and $^1$H NMR.

$C_{56}H_{37}N_3O$: calc. 767.93, found 767.94.

Synthesis Example 12: Synthesis of Compound 74

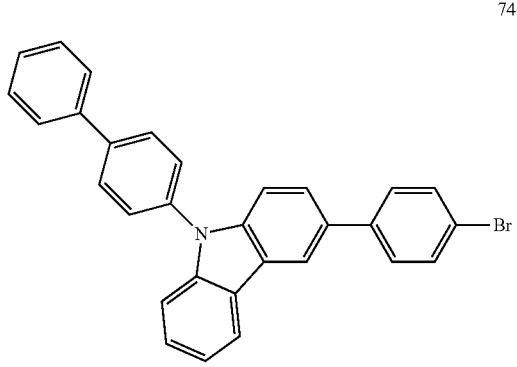

I-13

Compound 74 was synthesized in the same manner as in the synthesis of Compound 3 in Synthesis Example 1, except that Intermediate 74-A and Intermediate I-13, respectively, instead of Intermediate I-3 and Intermediate 3-A used in the synthesis of Compound 3 in Synthesis Example 1, were used. This compound was identified using MS/FAB and $^1$H NMR.

$C_{61}H_{42}N_2O$: calc. 819.02, found 819.06.

Synthesis Example 13: Synthesis of Compound 78

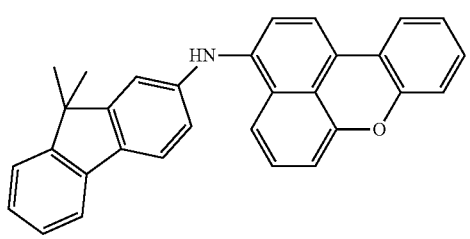

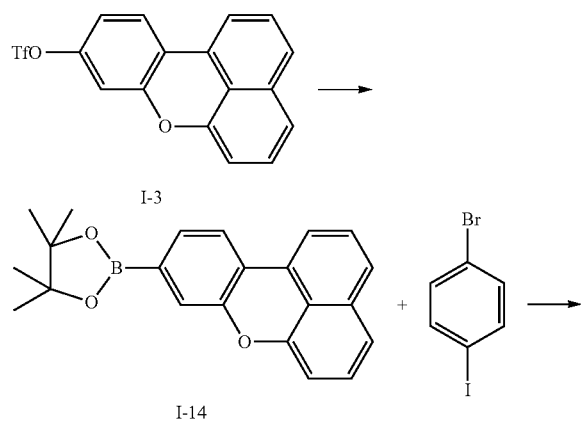

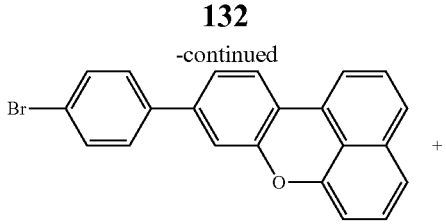

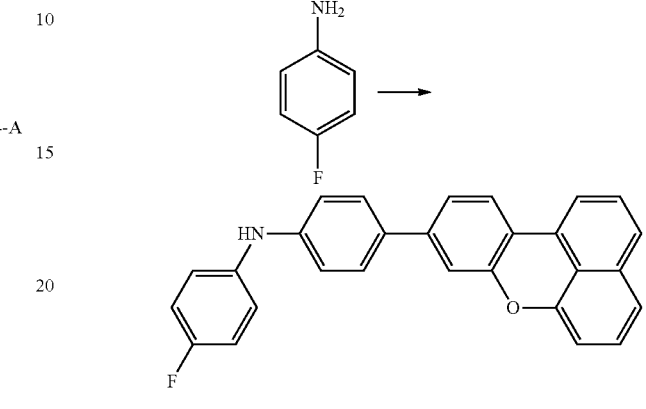

Synthesis of Intermediate I-14

Intermediate I-14 was synthesized in the same manner as in the synthesis of Intermediate 56-A in Synthesis Example 6, except that Intermediate I-13, instead of 3-iodo-9-phenyl-9H-carbazole used in the synthesis of Intermediate 56-A in Synthesis Example 6, was used. This compound was identified using MS/FAB.

$C_{22}H_{21}BO_3$: calc. 344.21, found 344.23.

Synthesis of Intermediate I-15

Intermediate I-15 was synthesized in the same manner as in the synthesis of Intermediate 56-B in Synthesis Example 6, except that Intermediate I-14, instead of 2-bromo-7-iodo-9,9-dimethyl-9H-fluorene used in the synthesis of Intermediate 56-B in Synthesis Example 6, was used. This compound was identified using MS/FAB.

$C_{22}H_{13}BrO$: calc. 373.24, found 373.26.

Synthesis of Intermediate I-16

Intermediate I-16 was synthesized in the same manner as in the synthesis of Compound 3 in Synthesis Example 1, except that 4-fluoroaniline and Intermediate I-15, respectively, instead of Intermediate 3-A and Intermediate I-3 used in the synthesis of Compound 3 in Synthesis Example 1, were used. This compound was identified using MS/FAB.

$C_{28}H_{18}FNO$: calc. 403.45, found 403.46.

Synthesis of Compound 78

Compound 78 was synthesized in the same manner as in the synthesis of Compound 3 in Synthesis Example 1, except that 3-iodo-9-phenyl-9H-carbazole and Intermediate I-16, respectively, instead of Intermediate I-3 and Intermediate 3-A used in the synthesis of Compound 3 in Synthesis Example 1, were used. This compound was identified using MS/FAB and $^1$H NMR.

$C_{46}H_{29}FN_2O$: calc. 644.74, found 644.76.

Synthesis Example 14: Synthesis of Compound 85

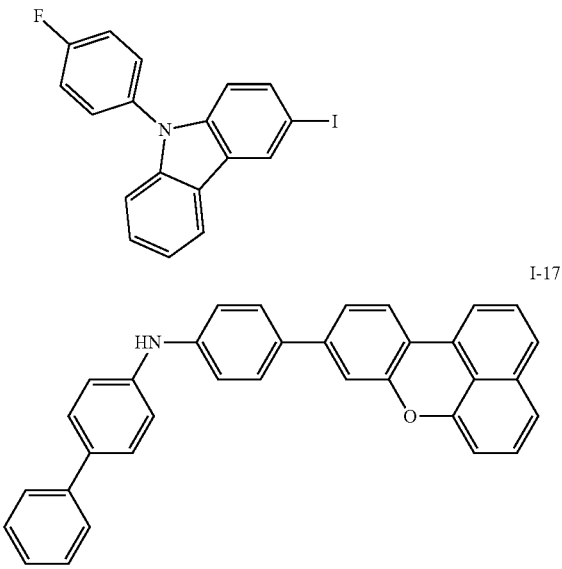

I-17

Compound 85 was synthesized in the same manner as in the synthesis of Compound 3 in Synthesis Example 1, except that 9-(4-fluorophenyl)-3-iodo-9H-carbazole and Intermediate I-17, respectively, instead of Intermediate I-3 and Intermediate 3-A used in the synthesis of Compound 3 in Synthesis Example 1, were used. This compound was identified using MS/FAB and $^1$H NMR.

$C_{52}H_{33}FN_2O$: calc. 720.84, found 720.86.

Synthesis Example 15: Synthesis of Compound 89

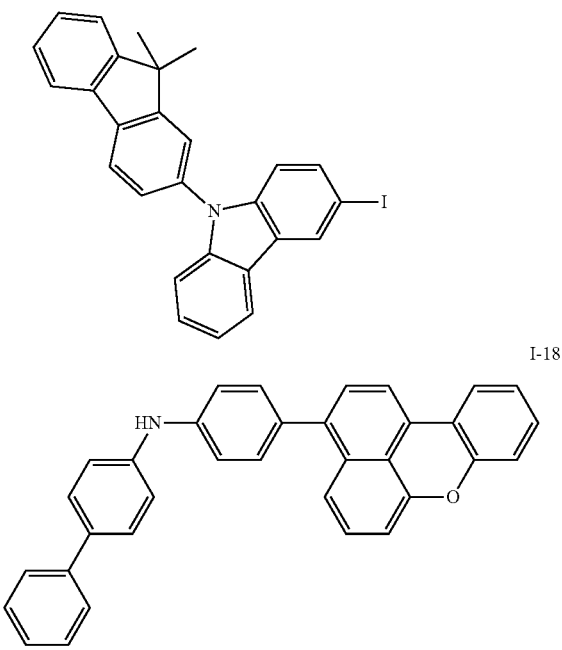

I-18

Compound 89 was synthesized in the same manner as in the synthesis of Compound 3 in Synthesis Example 1, except that 9-(9,9-dimethyl-9H-2-fluorene-2-yl)-3-iodo-9H-carbazole and Intermediate I-18, respectively, instead of Intermediate I-3 and Intermediate 3-A used in the synthesis of Compound 3 in Synthesis Example 1, were used. This compound was identified using MS/FAB and $^1$H NMR.

$C_{61}H_{42}N_2O$: calc. 819.02, found 819.03.

Synthesis Example 16: Synthesis of Compound 90

Compound 90 was synthesized in the same manner as in the synthesis of Compound 3 in Synthesis Example 1, except that Intermediate 57-A and Intermediate I-17, respectively, instead of Intermediate I-3 and Intermediate 3-A used in the synthesis of Compound 3 in Synthesis Example 1, were used. This compound was identified using MS/FAB and $^1$H NMR.

$C_{58}H_{38}N_2O$: calc. 778.95, found 778.97.

Synthesis Example 17: Synthesis of Compound 98

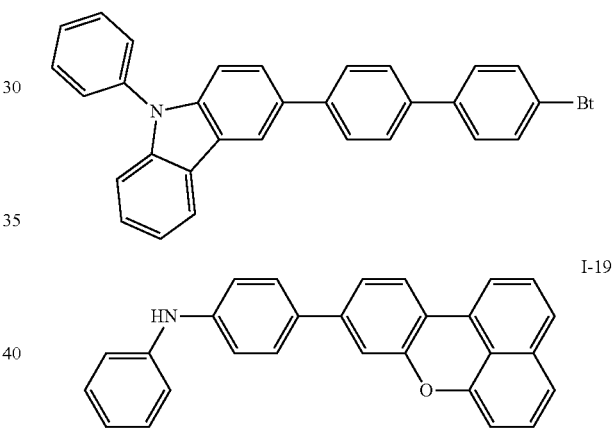

98-A

I-19

Compound 90 was synthesized in the same manner as in the synthesis of Compound 3 in Synthesis Example 1, except that Intermediate 98-A and Intermediate I-19, respectively, instead of Intermediate I-3 and Intermediate 3-A used in the synthesis of Compound 3 in Synthesis Example 1, were used. This compound was identified using MS/FAB and $^1$H NMR.

$C_{58}H_{38}N_2O$: calc. 778.95, found 778.96.

Synthesis Example 18: Synthesis of Compound 102

Compound 102 was synthesized in the same manner as in the synthesis of Compound 3 in Synthesis Example 1, except that 2-iodo-9-phenyl-9H-carbazole and Intermediate I-17, respectively, instead of Intermediate I-3 and Intermediate 3-A used in the synthesis of Compound 3 in Synthesis Example 1, were used. This compound was identified using MS/FAB and $^1$H NMR.

$C_{52}H_{34}N_2O$: calc. 702.85, found 702.87.

Synthesis Example 19: Synthesis of Compound 106

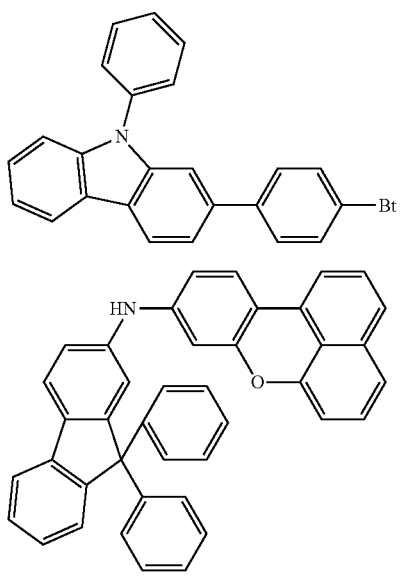

106-A

I-20

Compound 106 was synthesized in the same manner as in the synthesis of Compound 3 in Synthesis Example 1, except that Intermediate 106-A and Intermediate I-20, respectively, instead of Intermediate I-3 and Intermediate 3-A used in the synthesis of Compound 3 in Synthesis Example 1, were used. This compound was identified using MS/FAB and $^1$H NMR.

$C_{65}H_{42}N_2O$: calc. 867.06, found 867.09.

Synthesis Example 20: Synthesis of Compound 110

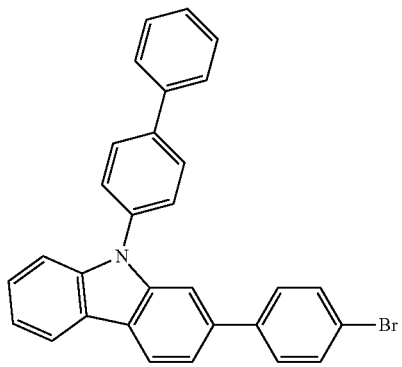

110-A

Compound 110 was synthesized in the same manner as in the synthesis of Compound 3 in Synthesis Example 1, except that Intermediate 110-A and Intermediate I-18, respectively, instead of Intermediate I-3 and Intermediate 3-A used in the synthesis of Compound 3 in Synthesis Example 1, were used. This compound was identified using MS/FAB and $^1$H NMR.

$C_{64}H_{42}N_2O$: calc. 855.05, found 855.07.

Synthesis Example 21: Synthesis of Compound 6

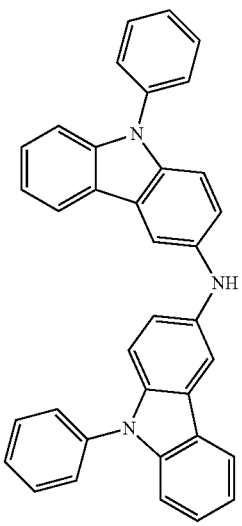

6-A

Compound 6 was synthesized in the same manner as in the synthesis of Compound 3 in Synthesis Example 1, except that Intermediate 6-A, instead of Intermediate 3-A used in the synthesis of Compound 3 in Synthesis Example 1, was used. This compound was identified using MS/FAB and $^1$H NMR.

Synthesis Example 22: Synthesis of Compound 7

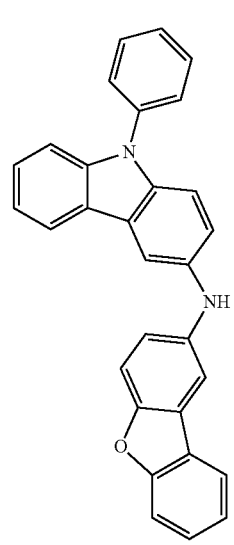

7-A

Compound 7 was synthesized in the same manner as in the synthesis of Compound 3 in Synthesis Example 1, except that Intermediate 7-A, instead of Intermediate 3-A used in the synthesis of Compound 3 in Synthesis Example 1, was used. This compound was identified using MS/FAB and $^1$H NMR.

Synthesis Example 23: Synthesis of Compound 12

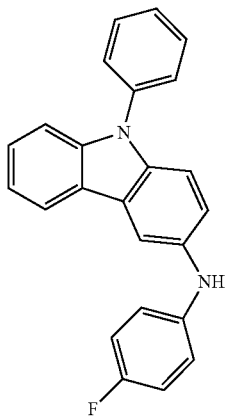

12-A

Compound 12 was synthesized in the same manner as in the synthesis of Compound 3 in Synthesis Example 1, except that Intermediate 12-A and Intermediate I-7, respectively, instead of Intermediate 3-A and Intermediate I-3 used in the synthesis of Compound 3 in Synthesis Example 1, were used. This compound was identified using MS/FAB and $^1$H NMR.

Synthesis Example 24: Synthesis of Compound 24

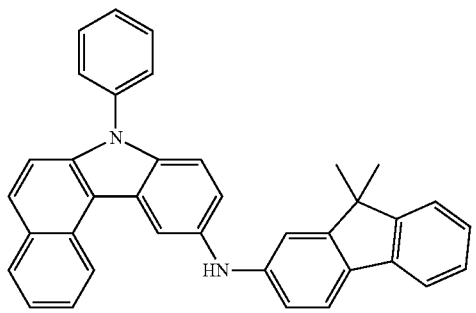

24-F

Synthesis of Intermediate 24-F

Intermediate 24-F was synthesized in the same manner as in the synthesis of Compound 3 in Synthesis Example 1, except that 9,9-dimethyl-9H-fluorene-2-amine and Intermediate 29-E, respectively, instead of Intermediate 3-A and Intermediate I-3 used in the synthesis of Compound 3 in Synthesis Example 1, were used.

Synthesis of Compound 24

Compound 24 was synthesized in the same manner as in the synthesis of Compound 3 in Synthesis Example 1, except that Intermediate 24-F, instead of Intermediate 3-A used in the synthesis of Compound 3 in Synthesis Example 1, was used. This compound was identified using MS/FAB and $^1$H NMR.

Synthesis Example 25: Synthesis of Compound 33

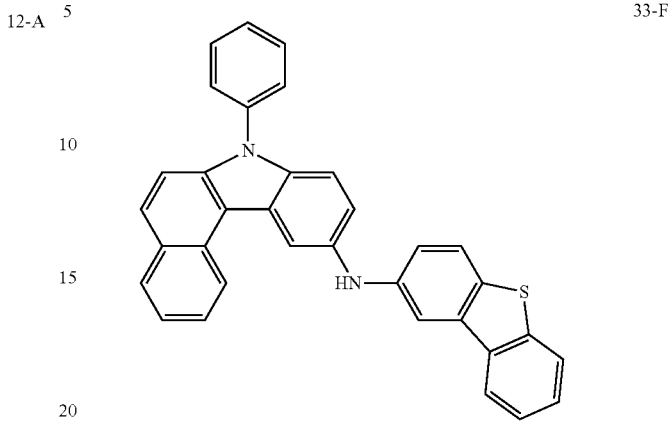

33-F

Synthesis of Intermediate 23-F

Intermediate 33-F was synthesized in the same manner as in the synthesis of Compound 3 in Synthesis Example 1, except that 2-aminodibenzothiophene and Intermediate 29-E, respectively, instead of Intermediate 3-A and Intermediate I-3 used in the synthesis of Compound 3 in Synthesis Example 1, were used.

Synthesis of Compound 33

Compound 33 was synthesized in the same manner as in the synthesis of Compound 3 in Synthesis Example 1, except that Intermediate 33-F, instead of Intermediate 3-A used in the synthesis of Compound 3 in Synthesis Example 1, was used. This compound was identified using MS/FAB and $^1$H NMR.

Synthesis Example 26: Synthesis of Compound 43

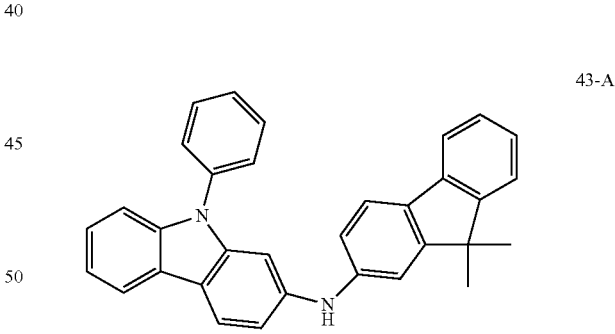

43-A

Compound 43 was synthesized in the same manner as in the synthesis of Compound 3 in Synthesis Example 1, except that Intermediate 43-A, instead of Intermediate 3-A used in the synthesis of Compound 3 in Synthesis Example 1, was used. This compound was identified using MS/FAB and $^1$H NMR.

Synthesis Example 27: Synthesis of Compound 52

Compound 52 was synthesized in the same manner as in the synthesis of Compound 3 in Synthesis Example 1, except that Intermediate 57-A and Intermediate I-8, respectively, instead of Intermediate I-3 and Intermediate 3-A used in the synthesis of Compound 3 in Synthesis Example 1, were used. This compound was identified using MS/FAB and ¹H NMR.

Synthesis Example 28: Synthesis of Compound 81

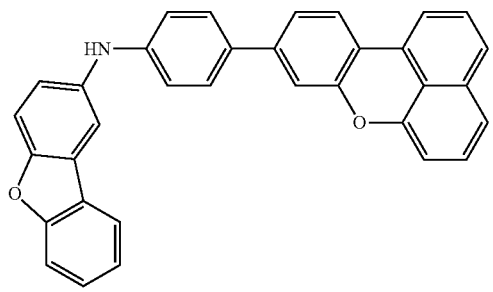

I-21

Synthesis of Intermediate I-21

Intermediate I-21 was synthesized in the same manner as in the synthesis of Compound 3 in Synthesis Example 1, except that 2-aminodibenzofuran and Intermediate I-15, respectively, instead of Intermediate 3-A and Intermediate I-3 used in the synthesis of Compound 3 in Synthesis Example 1, were used.

Synthesis of Compound 81

Compound 81 was synthesized in the same manner as in the synthesis of Compound 3 in Synthesis Example 1, except that 3-iodo-9-phenyl-9H-carbazole and Intermediate I-21, respectively, instead of Intermediate I-3 and Intermediate 3-A used in the synthesis of Compound 3 in Synthesis Example 1, were used. This compound was identified using MS/FAB and ¹H NMR.

¹H NMR and MS/FAB data of the compounds synthesized in the above synthesis examples are shown in Table 1.

Synthetic pathways and source materials for other compounds not in Table 1 would be apparent to one of ordinary skill in the art based on the synthetic pathways and source materials in Synthesis Examples 1 to 28.

TABLE 1

| Compound | ¹H NMR (CDCl₃, 400 MHz) | MS/FAB found | MS/FAB calc. | Yield (%) |
|---|---|---|---|---|
| 3 | δ = 8.25 – 8.22 (m, 2H), 7.83 – 7.80 (m, 1H), 7.76 – 7.70 (m, 2H), 7.61 – 7.55 (m, 3H), 7.53 – 7.47 (m, 6H), 7.40 – 7.20 (m, 7H), 7.13 – 7.05 (m, 3H), 6.91 (dd, 1H), 6.71 (d, 1H), 6.58 – 6.52 (m, 2H), 1.52 (s, 6H) | 666.85 | 666.82 | 82 |
| 6 | δ = 8.50 – 8.48 (m, 3H), 7.55 (d, 1H), 7.53 – 7.34 (m, 25H), 6.81 (m, 1H), 6.70 – 6.65 (m, 3H) | 715.87 | 715.85 | 76 |
| 7 | δ = 8.35 – 8.30 (m, 2H), 7.78 – 7.28 (m, 22H), 7.15 (m, 1H), 6.83 (m, 1H), 6.63 – 6.60 (m, 2H) | 640.76 | 640.74 | 79 |
| 12 | δ = 8.41 – 8.39 (m, 1H), 8.12 – 8.07 (m, 1H), 7.79 – 7.75 (m, 1H), 7.65 – 7.60 (m, 1H), 7.50 – 7.23 (m, 15H), 6.89 – 6.84 (m, 4H), 6.50 – 6.45 (m, 2H) | 568.66 | 568.65 | 85 |
| 21 | δ = 8.43 – 8.41 (m, 2H), 8.12 – 8.07 (m, 1H), 7.78 – 7.76 (m, 1H), 7.60 – 7.14 (m, 22H), 7.08 – 7.06 (m, 1H), 6.85 – 6.80 (m, 3H), 6.65 – 6.62 (m, 2H) | 676.86 | 676.81 | 88 |
| 24 | δ = 8.25 – 8.20 (m, 2H), 8.05 (d, 1H), 7.92 – 7.88 (m, 2H), 7.77 – 7.70 (m, 3H), 7.60 – 7.30 (m, 14H), 7.20 – 7.18 (m, 1H), 7.13 – 7.10 (m, 2H), 7.07 (dd, 1H), 6.58 – 6.55 (m, 2H), 1.59 (s, 6H) | 716.89 | 716.88 | 81 |
| 29 | δ = 8.43 (d, 1H), 8.25 (d, 1H), 8.06 (d, 1H), 7.88 (d, 1H), 7.80 – 7.73 (m, 2H), 7.64 – 7.61 (m, 1H), 7.55 – 7.48 (m, 6H), 7.45 – 7.28 (m, 9H), 7.11 – 7.09 (m, 1H), 6.92 – 6.88 (m, 2H), 6.76 – 6.72 (m, 2H) | 625.76 | 625.73 | 74 |
| 33 | δ = 8.43 (d, 1H), 8.23 (d, 1H), 8.06 (d, 1H), 7.90 – 7.70 (m, 6H), 7.63 – 7.48 (m, 9H), 7.45 – 777.30 (m, 8H), 7.13 – 7.10 (m, 1H), 6.90 – 6.85 (m, 2H), 6.76 (dd, 1H) | 706.88 | 706.86 | 80 |
| 40 | δ = 8.25 – 8.20 (m, 1H), 8.17 – 8.10 (m, 1H), 7.74 (d, 1H), 7.67 (d, 1H), 7.60 – 7.43 (m, 14H), 7.38 – 7.28 (m, 5H), 7.25 – 7.20 (m, 2H), 7.04 (dd, 1H), 6.98 – 6.97 (m, 1H), 6.92 – 6.88 (m, 2H), 6.68 – 6.63 (m, 2H) | 626.26 | 626.75 | 77 |
| 43 | δ = 8.25 – 8.20 (m, 1H), 8.17 – 8.10 (m, 1H), 7.78 – 7.70 (m, 3H), 7.60 – 7.55 (m, 3H), 7.53 – 7.46 (m, 6H), 7.38 – 7.28 (m, 5H), 7.25 – 7.20 (m, 2H), 7.12 – 7.10 (m, 2H), 7.08 – 6.97 (m, 2H), 6.77 (d, 1H), 6.65 – 6.60 (m, 2H), 1.59 (s, 6H) | 666.84 | 666.83 | 76 |
| 49 | δ = 8.43 (dd, 1H), 8.17 – 8.14 (m, 1H), 7.80 – 7.70 (m, 3H), 7.63 – 7.58 (m, 3H), 7.50 – 7.29 (m, 16H), 7.26 – 7.24 (m, 1H), 7.13 – 7.10 (m, 3H), 6.78 – 6.74 (m, 2H), 6.62 (d, 1H), 6.58 (d, 1H), 1.52 (s, 6H) | 742.94 | 742.92 | 72 |
| 52 | δ = 8.25 – 8.20 (m, 2H), 8.06 – 8.04 (m, 1H), 7.77 – 7.75 (m, 1H), 7.69 – 7.45 (m, 12H), 7.38 – 7.25 (m, 3H), 7.22 – 7.19 (m, 2H), 7.06 – 7.02 (m, 2H), 6.74 – 6.70 (m, 3H), 6.63 – 6.60 (m, 1H), 6.56 (d, 1H), 6.36 – 6.32 (m, 2H) | 626.77 | 626.75 | 81 |
| 56 | δ = 8.25 – 8.20 (m, 2H), 8.06 – 8.04 (m, 1H), 7.90 – 7.88 (m, 1H), 7.80 – 7.78 (m, 1H), 7.71 – 7.68 (m, 2H), 7.60 – 7.54 (m, 4H), 7.52 – 7.42 (m, 6H), 7.38 – 7.25 (m, 3H), 7.22 – 7.18 (m, 2H), 7.11 – 7.05 (m, 3H), 6.65 – 6.62 (m, 3H), 6.57 – 6.52 (m, 2H), 6.38 – 6.35 (m, 2H), 1.53 (s, 6H) | 742.31 | 742.92 | 73 |
| 57 | δ = 8.25 – 8.20 (m, 2H), 8.06 – 8.04 (m, 1H), 7.75 – 7.73 (m, 1H), 7.68 – 7.45 (m, 12H), 7.39 – 7.26 (m, 3H), 7.22 – 7.18 (m, 2H), 6.96 – 6.92 (m, 2H), 6.78 – 6.73 (m, 3H), 6.69 – 6.65 (m, 2H), 6.53 (d, 1H) | 644.76 | 644.74 | 77 |
| 59 | δ = 8.25 – 8.20 (m, 2H), 8.06 – 8.04 (m, 1H), 7.75 – 7.73 (m, 1H), 7.68 – 7.55 (m, 9H), 7.52 – 7.44 (m, 8H), 7.40 – | 702.87 | 702.26 | 74 |

TABLE 1-continued

| Compound | 1H NMR (CDCl3, 400 MHz) | MS/FAB found | MS/FAB calc. | Yield (%) |
|---|---|---|---|---|
| | 7.25 (m, 5H), 7.21 – 7.19 (m, 2H), 6.78 – 6.69 (m, 5H), 6.54 (d, 1H) | | | |
| 62 | δ = 8.25 – 8.20 (m, 2H), 8.06 – 8.04 (m, 1H), 7.78 – 7.73 (m, 2H), 7.70 – 7.65 (m, 2H), 7.60 – 7.55 (m, 5H), 7.52 – 7.45 (m, 6H), 7.38 – 7.26 (m, 4H), 7.23 – 7.19 (m, 2H), 7.13 – 7.10 (m, 2H), 6.89 (d, 1H), 6.71 – 6.68 (m, 3H), 6.55 – 6.52 (m, 2H), 1.53 (s, 6H), | 742.93 | 742.92 | 82 |
| 63 | δ = 8.25 – 8.20 (m, 2H), 8.06 – 8.04 (m, 1H), 7.85 – 7.83 (m, 1H), 7.75 – 7.72 (m, 1H), 7.69 – 7.66 (m, 2H), 7.60 – 7.45 (m, 12H), 7.42 – 7.28 (m, 6H), 7.23 – 7.18 (m, 2H), 7.05 (dd, 1H), 6.84 – 6.78 (m, 3H), 6.59 (dd, 1H) | 716.86 | 716.84 | 86 |
| 70 | δ = 8.25 – 8.20 (m, 2H), 8.06 – 8.04 (m, 1H), 7.85 – 7.82 (m, 2H), 7.78 – 7.73 (m, 2H), 7.68 – 7.62 (m, 2H), 7.60 – 7.55 (m, 7H), 7.52 – 7.45 (m, 2H), 7.38 – 7.28 (m, 3H), 7.22 – 7.18 (m, 2H), 7.15 – 7.10 (m, 2H), 6.84 (dd, 1H), 6.70 – 6.66 (m, 3H), 6.56 – 6.52 (m, 2H), 1.53 (s, 6H), | 767.94 | 767.93 | 89 |
| 74 | δ = 8.46 – 8.42 (m, 1H), 8.26 – 8.22 (m, 1H), 8.06 – 8.04 (m, 1H), 7.80 – 7.74 (m, 3H), 7.68 – 7.52 (m, 6H), 7.50 – 7.25 (m, 15H), 7.21 – 7.19 (m, 1H), 7.13 – 7.10 (m, 3H), 6.72 (d, 1H), 6.66 (dd, 1H), 6.52 – 6.49 (m, 2H), 6.45 – 6.44 (m, 1H), 1.52 (s, 6H), | 819.06 | 819.02 | 85 |
| 78 | δ = 8.22 – 8.19 (m, 1H), 8.16 – 8.13 (m, 1H), 7.90 – 7.88 (m, 1H), 7.60 – 7.54 (m, 3H), 7.52 – 7.48 (m, 6H), 7.44 – 7.35 (m, 6H), 7.32 – 7.22 (m, 3H), 7.08 – 7.05 (m, 1H), 6.98 – 6.90 (m, 2H), 6.65 – 6.58 (m, 5H) | 644.76 | 644.74 | 84 |
| 81 | δ = 8.22 – 8.20 (m, 1H), 8.16 – 8.10 (m, 1H), 7.88 (d, 1H), 7.84 – 7.80 (m, 1H), 7.60 – 7.22 (m, 23H), 7.08 – 7.06 (m, 1H), 6.96 (dd, 1H), 6.70 – 6.65 (m, 2H), 6.60 (dd, 1H) | 716.86 | 716.84 | 82 |
| 85 | δ = 8.22 – 8.20 (m, 1H), 8.16 – 8.10 (m, 1H), 7.89 (d, 1H), 7.61 – 7.56 (m, 5H), 7.52 – 7.30 (m, 15H), 7.28 – 7.24 (m, 2H), 7.10 – 7.06 (m, 3H), 6.67 – 6.54 (m, 5H) | 720.86 | 720.84 | 82 |
| 89 | δ = 8.42 – 8.40 (m, 1H), 8.26 – 8.22 (m, 1H), 7.92 (d, 1H), 7.86 – 7.84 (m, 1H), 7.63 – 7.55 (m, 3H), 7.52 – 7.06 (m, 24H), 6.68 – 6.65 (m, 2H), 6.60 – 6.56 (m, 3H), 1.52 (s, 6H), | 819.03 | 819.02 | 76 |
| 90 | δ = 8.25 – 8.22 (m, 1H), 8.15 – 8.13 (m, 1H), 8.07 – 8.05 (m, 1H), 7.89 (d, 1H), 7.76 (d, 1H), 7.65 (dd, 1H), 7.60 – 7.25 (m, 24H), 7.22 – 7.20 (m, 1H), 7.07 – 7.04 (m, 1H), 6.85 – 6.80 (m, 2H), 6.65 – 6.55 (m, 4H), | 778.97 | 778.95 | 74 |
| 98 | δ = 8.46 – 8.44 (m, 1H), 8.23 (t, 1H), 8.10 – 8.08 (m, 1H), 7.94 – 7.85 (m, 3H), 7.76 – 7.27 (m, 20H), 7.21 – 7.19 (m, 1H), 7.09 – 7.02 (m, 3H), 7.22 – 7.20 (m, 1H), 7.07 – 7.04 (m, 1H), 6.96 – 6.92 (m, 1H), 6.85 – 6.81 (m, 2H), 6.68 – 6.62 (m, 1H), 6.23 – 6.20 (m, 2H), | 778.96 | 778.95 | 73 |
| 102 | δ = 8.18 – 8.12 (m, 2H), 7.90 – 7.85 (m, 1H), 7.75 – 7.72 (m, 1H), 7.60 – 7.27 (m, 22H), 7.25 – 7.23 (m, 1H), 7.07 – 7.04 (m, 1H), 7.02 – 7.00 (m, 1H), 6.59 (dd, 1H), 6.80 – 6.75 (m, 4H) | 702.87 | 702.85 | 71 |
| 106 | δ = 8.25 – 8.20 (m, 1H), 8.14 – 8.12 (m, 1H), 7.86 – 7.79 (m, 3H), 7.68 (d, 1H), 7.60 – 7.54 (m, 3H), 7.52 – 7.10 (m, 26H), 6.86 – 6.79 (m, 4H), 6.70 – 6.68 (m, 1H), 6.57 – 6.52 (m, 2H) | 867.09 | 867.06 | 72 |
| 110 | δ = 8.43 – 8.40 (m, 1H), 8.27 – 8.24 (m, 1H), 8.15 – 8.13 (m, 1H), 7.93 – 7.91 (m, 1H), 7.85 – 7.80 (m, 2H), 7.63 – 7.55 (m, 5H), 7.55 – 7.28 (m, 23H), 7.20 – 7.18 (m, 1H), 7.08 – 7.05 (m, 1H), 6.97 – 6.93 (m, 2H), 6.85 – 6.82 (m, 2H), 6.75 – 6.72 (m, 2H) | 855.07 | 855.05 | 70 |

Example 1

A 15 Ω/cm² ITO glass substrate (having a thickness of 1,200 Å, available from Corning) was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate with an ITO anode was mounted into a vacuum deposition device.

2-TNATA was vacuum-deposited on the ITO anode of the glass substrate to form an HIL having a thickness of 600 Å, and Compound 3 was deposited on the HIL to form a HTL having a thickness of about 300 Å, thus forming a hole transport region.

9,10-di-naphthalene-2-yl-anthracene (ADN) as a host and N,N,N',N'-tetraphenyl-pyrene-1,6-diamine (TPD) (as Compound FD1) as a dopant were co-deposited on the hole transport region in a weight ratio of about 98:2 to form an EML having a thickness of about 300 Å.

Alq₃ was then deposited on the EML to form an ETL having a thickness of about 300 Å, and then LiF was deposited on the ETL to form an EIL having a thickness of about 10 Å, thus forming an electron transport region.

Subsequently, Al was vacuum-deposited on the electron transport region to form a cathode having a thickness of about 3,000 Å, thereby completing the manufacture of an organic light-emitting device.

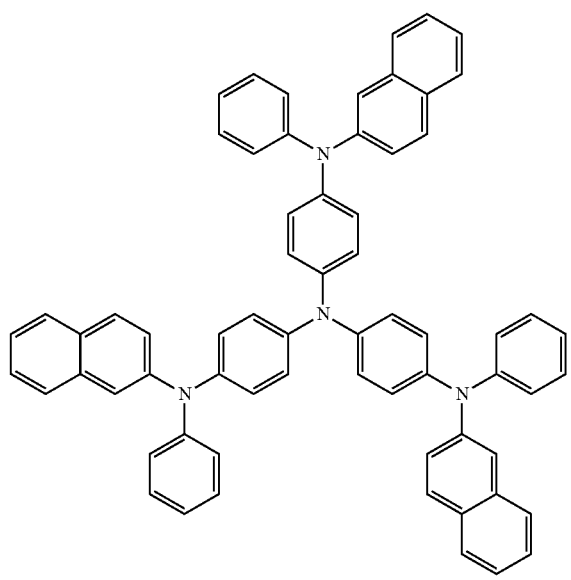

2-TNATA

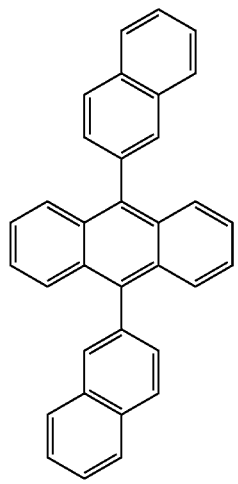

ADN

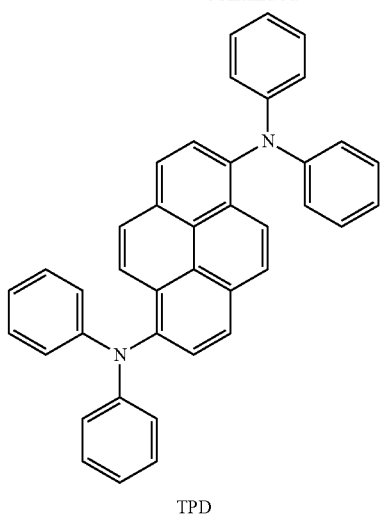

TPD

Example 2 to 20, and Comparative Examples 1 to 3

Organic light-emitting devices were manufactured in the same manner as in Example 1, except that the compounds in Table 2, instead of Compound 3 used in Example 1, were used, respectively.

Evaluation Example 1

Driving voltages, current densities, luminance, efficiency, and half-lifetimes of the organic light-emitting devices of Examples 1 to 20 and Comparative Examples 1 to 3 were evaluated using a Keithley Source-Measure Unit (SMU 236) and a PR650 Spectroscan available from Photo Research, Inc. The results are shown in Table 2. A half-lifetime was measured as the time taken until a measured initial luminance (assumed as 100%) is reduced to 50%.

TABLE 2

| Example | HTL material | Driving voltage (V) | Current density (mA/cm$^2$) | Luminance (cd/m$^2$) | Efficiency (cd/A) | Emission color | Half-lifetime (hr) @50 mA/cm$^2$ |
|---|---|---|---|---|---|---|---|
| Example 1 | Compound 3 | 5.68 | 50 | 3080 | 6.16 | blue | 305 |
| Example 2 | Compound 21 | 5.65 | 50 | 3085 | 6.17 | blue | 308 |
| Example 3 | Compound 29 | 5.70 | 50 | 3082 | 6.16 | blue | 312 |
| Example 4 | Compound 40 | 5.65 | 50 | 3095 | 6.19 | blue | 300 |
| Example 5 | Compound 49 | 5.64 | 50 | 3110 | 6.42 | blue | 315 |
| Example 6 | Compound 56 | 5.42 | 50 | 3190 | 6.22 | blue | 325 |
| Example 7 | Compound 57 | 5.43 | 50 | 3220 | 6.44 | blue | 329 |
| Example 8 | Compound 59 | 5.40 | 50 | 3250 | 6.50 | blue | 340 |
| Example 9 | Compound 62 | 5.42 | 50 | 3330 | 6.66 | blue | 355 |
| Example 10 | Compound 63 | 5.50 | 50 | 3280 | 6.56 | blue | 335 |

TABLE 2-continued

| Example | HTL material | Driving voltage (V) | Current density (mA/cm$^2$) | Luminance (cd/m$^2$) | Efficiency (cd/A) | Emission color | Half-lifetime (hr) @50 mA/cm$^2$ |
|---|---|---|---|---|---|---|---|
| Example 11 | Compound 70 | 5.50 | 50 | 3220 | 6.44 | blue | 370 |
| Example 12 | Compound 74 | 5.45 | 50 | 3215 | 6.43 | blue | 340 |
| Example 13 | Compound 78 | 5.51 | 50 | 3220 | 6.44 | blue | 325 |
| Example 14 | Compound 85 | 5.53 | 50 | 3218 | 6.43 | blue | 330 |
| Example 15 | Compound 89 | 5.53 | 50 | 3220 | 6.44 | blue | 335 |
| Example 16 | Compound 90 | 5.51 | 50 | 3215 | 6.43 | blue | 350 |
| Example 17 | Compound 98 | 5.60 | 50 | 3200 | 6.40 | blue | 338 |
| Example 18 | Compound 102 | 5.55 | 50 | 3290 | 6.58 | blue | 330 |
| Example 19 | Compound 106 | 5.60 | 50 | 3210 | 6.42 | blue | 325 |
| Example 20 | Compound 110 | 5.57 | 50 | 3200 | 6.40 | blue | 340 |
| Comparative Example 1 | NPB | 7.01 | 50 | 2645 | 5.29 | blue | 258 |
| Comparative Example 2 | Compound A | 6.56 | 50 | 2720 | 5.44 | blue | 240 |
| Comparative Example 3 | Compound B | 6.46 | 50 | 2845 | 5.69 | blue | 234 |

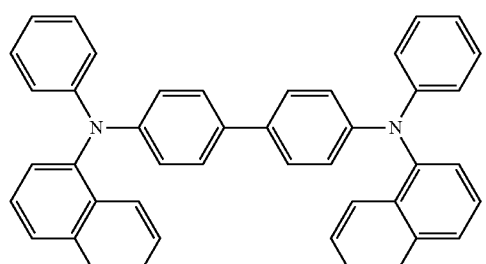

NPB

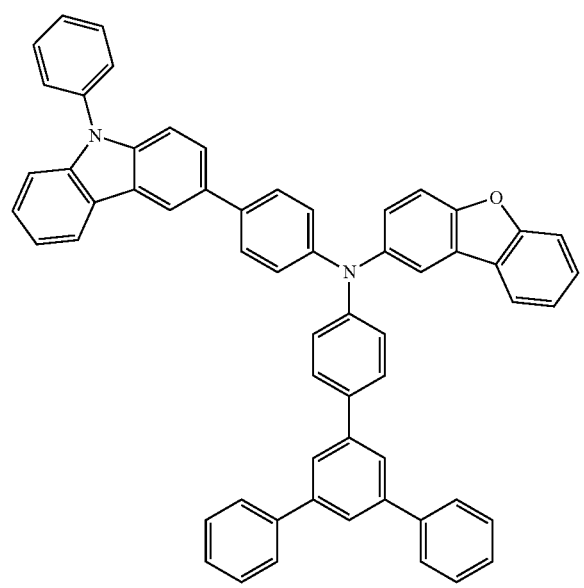

<Compound A>

<Compound B>

As described above, according to the one or more embodiments of the present disclosure, an organic light-emitting device including an amine-based compound of Formula 1 may have a low driving voltage, an improved efficiency, improved luminance and long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope thereof as set forth in the following claims.

What is claimed is:

1. An amine-based compound represented by Formula 1:

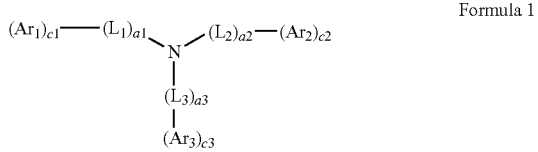

Formula 1 wherein, in Formula 1, $L_1$ to $L_3$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a3 are each independently an integer selected from 0 to 3, wherein at least two $L_1$s are the same or different when a1 is 2 or greater, at least two $L_2$s are the same or different when a2 is 2 or greater, and at least two $L_3$s are the same or different when a3 is 2 or greater;

$Ar_1$ is a group represented by Formula 2;

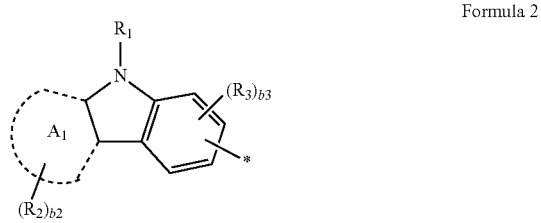

Formula 2

$Ar_2$ is a group represented by Formula 3A or a group represented by Formula 3B;

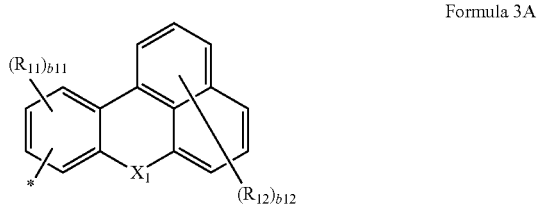

Formula 3A

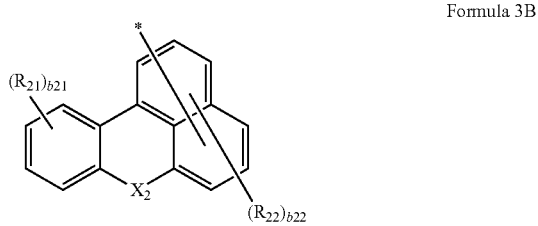

Formula 3B $Ar_3$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and c1 to c3 are each independently an integer selected from 1 to 3, wherein at least two $Ar_1$s are the same or different when c1 is 2 or greater, at least two $Ar_2$s are the same or different when c2 is 2 or greater, and at least two $Ar_3$s are the same or different when c3 is 2 or greater, and in Formulae 2, 3A, and 3B, $A_1$ is a ring selected from benzene, naphthalene, fluorene, phenanthrene and pyrene;

$R_1$ is selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$X_1$ and $X_2$ are each independently O or S;

$R_2$, $R_3$, $R_{11}$, $R_{12}$, $R_{21}$, and $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

b2 and b21 are each independently an integer selected from 1 to 4, wherein at least two $R_2$s are the same or different when b2 is 2 or greater, and at least two $R_{21}$s are the same or different when b21 is 2 or greater;

b3 and b11 are each independently an integer selected from 1 to 3, wherein at least two $R_3$s are the same or different when b3 is 2 or greater, and at least two $R_{11}$s are the same or different when b11 is 2 or greater;

b12 is an integer selected from 1 to 6, wherein at least two $R_{12}$s are the same or different when b12 is 2 or greater;

b22 is an integer selected from 1 to 5, wherein at least two $R_{22}$s are the same or different when b22 is 2 or greater;

* indicates a binding site with an adjacent atom;

at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$); and $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The amine-based compound as claimed in claim 1, wherein $L_1$ to $L_3$ are each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

3. The amine-based compound as claimed in claim 1, wherein $L_1$ to $L_3$ are each independently a group represented by one of Formulae 4-1 to 4-33:

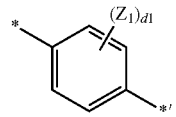

Formula 4-1

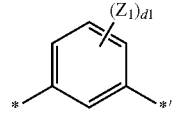

Formula 4-2

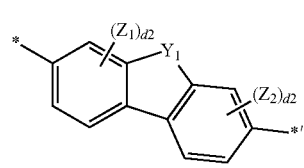

Formula 4-3

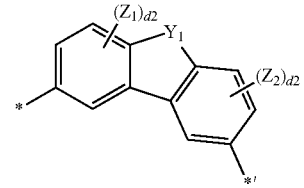

Formula 4-4

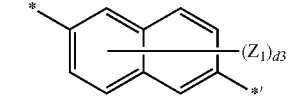

Formula 4-5

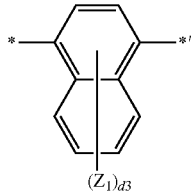

Formula 4-6

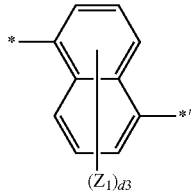

Formula 4-7

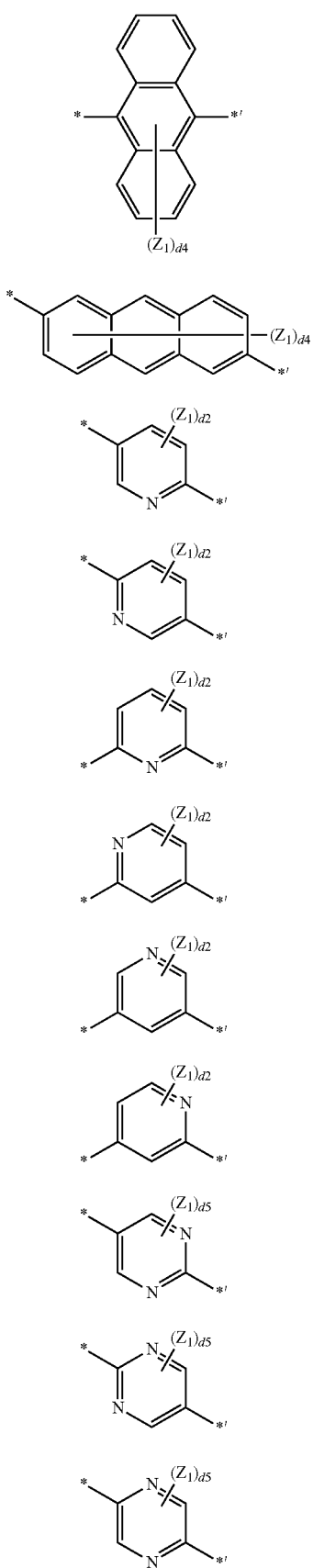
Formula 4-8
Formula 4-9
Formula 4-10
Formula 4-11
Formula 4-12
Formula 4-13
Formula 4-14
Formula 4-15
Formula 4-16
Formula 4-17
Formula 4-18
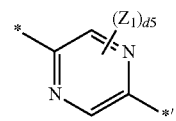
Formula 4-19
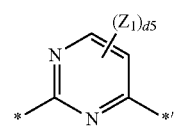
Formula 4-20
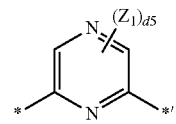
Formula 4-21
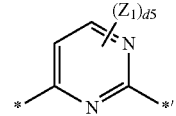
Formula 4-22
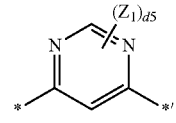
Formula 4-23
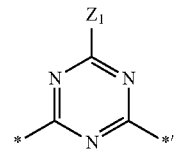
Formula 4-24
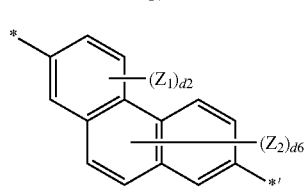
Formula 4-25
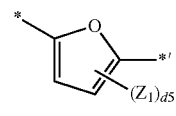
Formula 4-26
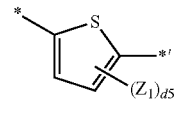
Formula 4-27
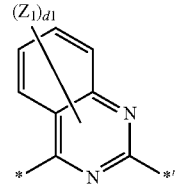
Formula 4-28
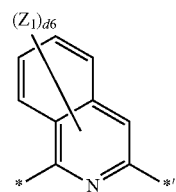
Formula 4-29

-continued

Formula 4-30

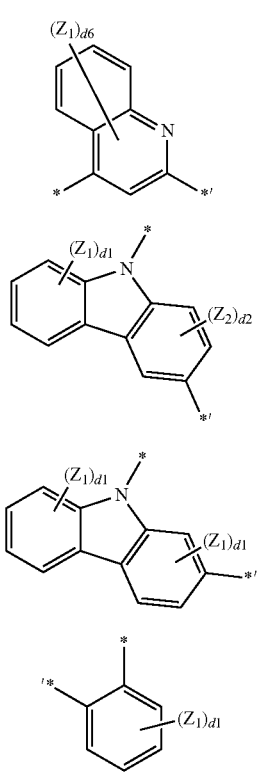

Formula 4-31

Formula 4-32

Formula 4-33 wherein, in Formulae 4-1 to 4-33,
$Y_1$ is O, S, $C(Z_3)(Z_4)$, $N(Z_5)$, or $Si(Z_6)(Z_7)$;
$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;
d1 is an integer selected from 1 to 4;
d2 is an integer selected from 1 to 3;
d3 is an integer selected from 1 to 6;
d4 is an integer selected from 1 to 8;
d5 is 1 or 2;
d6 is an integer selected from 1 to 5; and
* and *' are each a binding site with an adjacent atom.

4. The amine-based compound as claimed in claim 1, wherein $L_1$ to $L_3$ are each independently a group represented by one of Formulae 5-1 to 5-27:

Formula 5-1

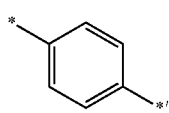

-continued

Formula 5-2

Formula 5-3

Formula 5-4

Formula 5-5

Formula 5-6

Formula 5-7

Formula 5-8

Formula 5-9

Formula 5-10

Formula 5-11

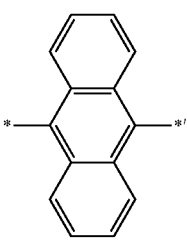

Formula 5-12

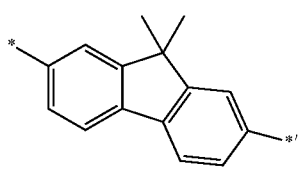

Formula 5-13

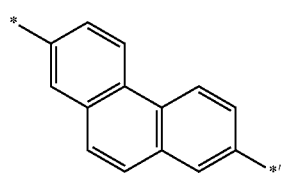

Formula 5-14

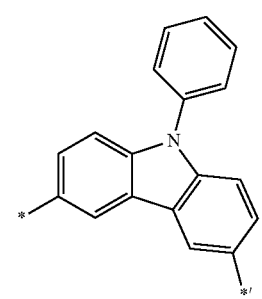

Formula 5-15

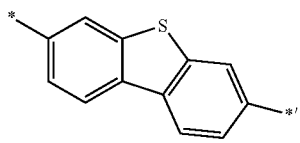

Formula 5-16

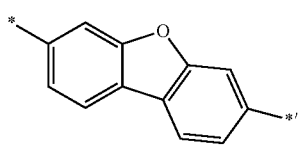

Formula 5-17

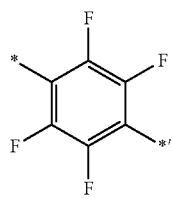

Formula 5-18

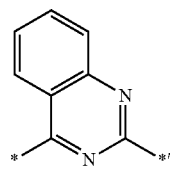

Formula 5-19

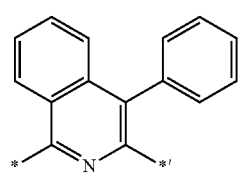

Formula 5-20

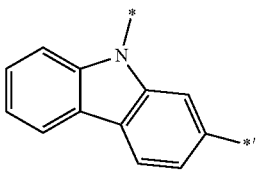

Formula 5-21

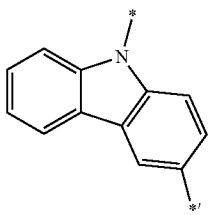

Formula 5-22

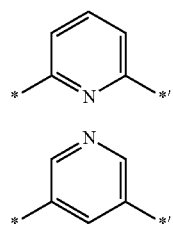

Formula 5-23

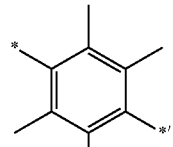

Formula 5-24

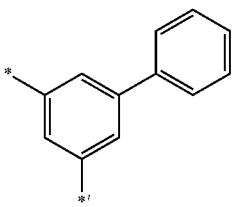

Formula 5-25

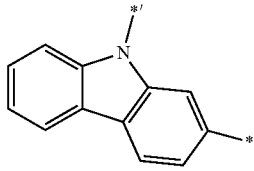

Formula 5-26

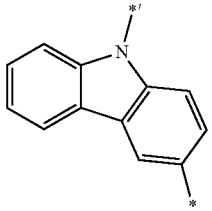

Formula 5-27 wherein, in Formulae 5-1 to 5-27, * and *' are each a binding site with an adjacent atom.

5. The amine-based compound as claimed in claim 1, wherein a1, a2, and a3 are each independently 0, 1, or 2.

6. The amine-based compound as claimed in claim 1, wherein $A_1$ is a ring selected from benzene or naphthalene.

7. The amine-based compound as claimed in claim 1, wherein $R_1$ and $Ar_3$ are each independently selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$), wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

8. The amine-based compound as claimed in claim 1, wherein $R_1$ and $Ar_3$ are each independently selected from:
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group, and
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, a dibenzocarbazolyl group, and —Si($Q_{33}$)($Q_{34}$)($Q_{35}$), wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

9. The amine-based compound as claimed in claim 1, wherein $R_1$ and $Ar_3$ are each independently selected from groups represented by Formulae 6-1 to 6-17:

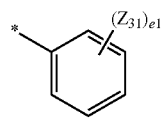

Formula 6-1

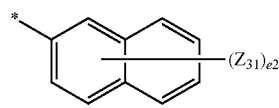

Formula 6-2

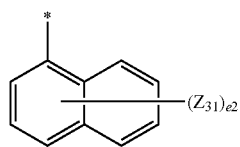

Formula 6-3

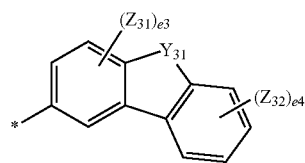

Formula 6-4

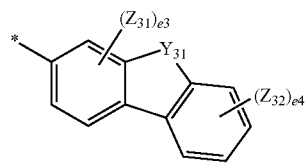

Formula 6-5

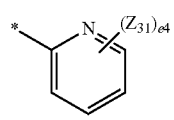

Formula 6-6

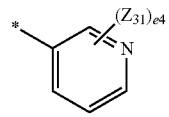

Formula 6-7

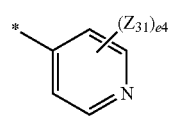

Formula 6-8

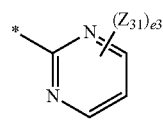

Formula 6-9

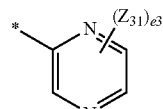

Formula 6-10

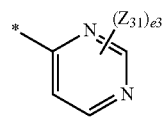

Formula 6-11

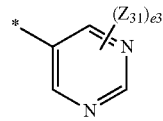

Formula 6-12

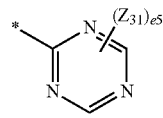

Formula 6-13

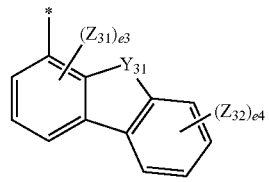

Formula 6-14

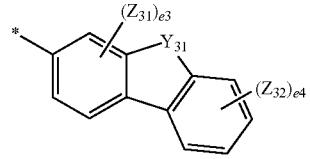

Formula 6-15

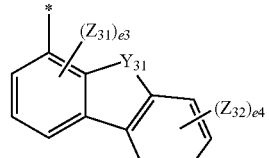

Formula 6-16

Formula 6-17

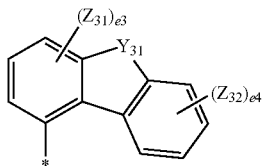

wherein, in Formulae 6-1 to 6-17, $Y_{31}$ is O, S, $C(Z_{33})(Z_{34})$, or $N(Z_{35})$;

$Z_{31}$ to $Z_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, a dibenzocarbazolyl group, and —$Si(Q_{33})(Q_{34})(Q_{35})$, wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

e1 is an integer of 1 to 5;

e2 is an integer of 1 to 7;

e3 is an integer of 1 to 3;

e4 is an integer of 1 to 4;

e5 is an integer of 1 or 2; and

* is a binding site with an adjacent atom.

10. The amine-based compound as claimed in claim 1, wherein $X_1$ and $X_2$ are O.

11. The amine-based compound as claimed in claim 1, wherein $R_2$, $R_3$, $R_{11}$, $R_{12}$, $R_{21}$, and $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —$Si(Q_3)(Q_4)(Q_5)$, wherein $Q_3$ to $Q_5$ are each independently selected from a $C_1$-$C_{20}$ alkyl group, a $C_1$-$C_{20}$ alkoxy group, a phenyl group, and a naphthyl group.

12. The amine-based compound as claimed in claim 1, wherein $R_2$, $R_3$, $R_{11}$, $R_{12}$, $R_{21}$, and $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

13. The amine-based compound as claimed in claim 1, wherein $Ar_1$ is a group represented by one of Formulae 2-1 to 2-6:

Formula 2-1

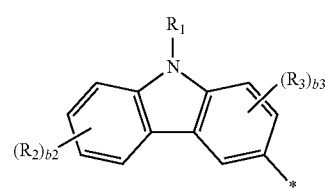

Formula 2-2

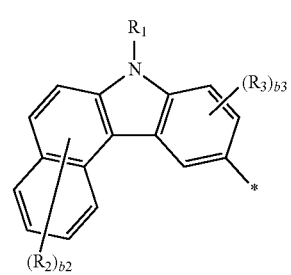

Formula 2-3

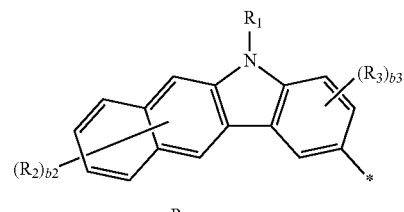

Formula 2-4

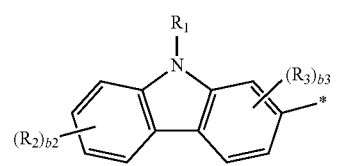

Formula 2-5

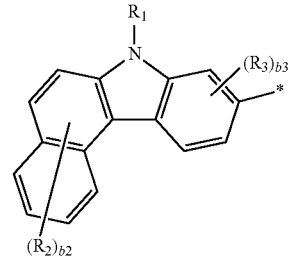

Formula 2-6

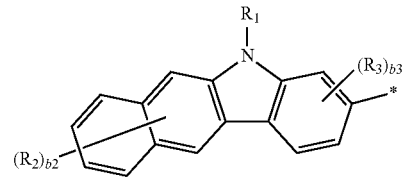

wherein, in Formulae 2-1 to 2-6,
$R_1$ is selected from:
- a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and
- a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and —Si($Q_{33}$)($Q_{34}$)($Q_{35}$), wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_2$ and $R_3$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof a sulfonic acid group or a salt thereof, a phosphoric acid group or a salt thereof, a $C_1$-$C_{20}$ alkyl group, and a $C_1$-$C_{20}$ alkoxy group;

b2 and b3 are each independently 1 or 2; and
* is a binding site with an adjacent atom.

14. The amine-based compound as claimed in claim 1, wherein $Ar_2$ is a group represented by one of Formulae 3A-1, 3B-1, 3A-2, and 3B-2:

Formula 3A-1

Formula 3B-1

Formula 3A-2

Formula 3B-2 wherein, in Formulae 3A-1, 3B-1, 3A-2, and 3B-2,
$R_{11}$, $R_{12}$, $R_{21}$, and $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

b21 and b22 are each independently 1 or 2; and
* is a binding site with an adjacent atom.

15. The amine-based compound as claimed in claim 1, wherein:
$L_1$ to $L_3$ are each independently a group represented by one of Formulae 5-1 to 5-27;
a1 to a3 are each independently 0, 1, or 2;
$Ar_1$ is a group represented by one of Formulae 2-1 to 2-6;
$Ar_2$ is a group represented by one of Formulae 3A-1, 3B-1, 3A-2, and 3B-2; and
$Ar_3$ is selected from:
- a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group, and
- a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, and a dibenzocarbazolyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group a dibenzofuranyl group, a dibenzothiophenyl group, a benzocarbazolyl group, a dibenzocarbazolyl group, and —Si($Q_{33}$)($Q_{34}$)($Q_{35}$), wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group:

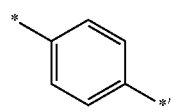

Formula 5-1

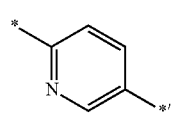

Formula 5-2

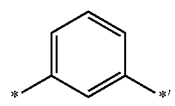

Formula 5-3

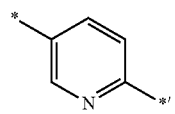

Formula 5-4

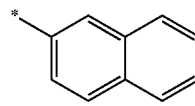

Formula 5-5

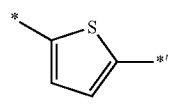

Formula 5-6

Formula 5-7

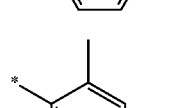

Formula 5-8

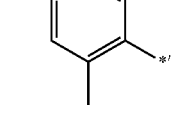

Formula 5-9

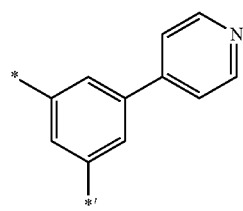

-continued

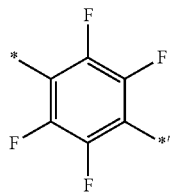

Formula 5-10

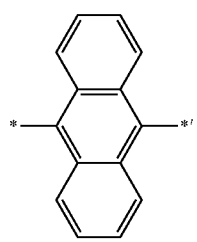

Formula 5-11

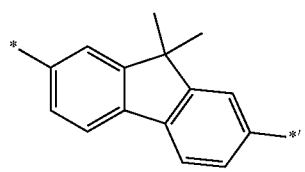

Formula 5-12

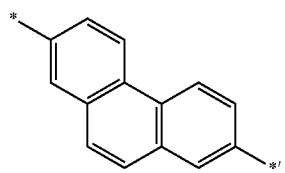

Formula 5-13

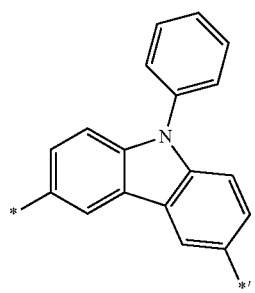

Formula 5-14

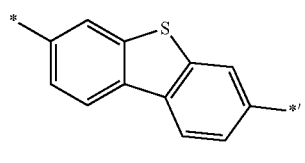

Formula 5-15

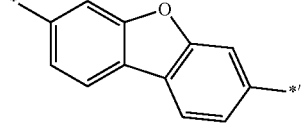

Formula 5-16

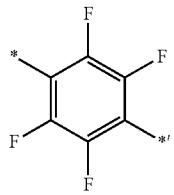

Formula 5-17

169
-continued
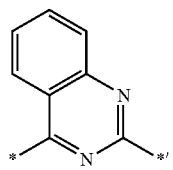
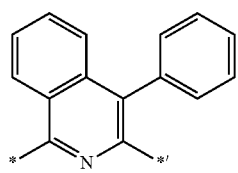
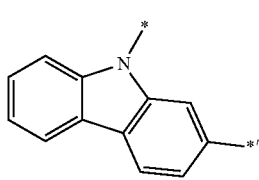
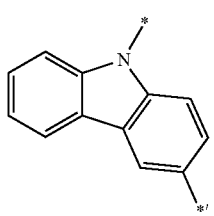
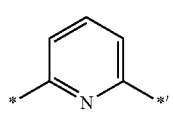
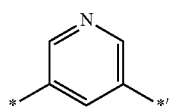
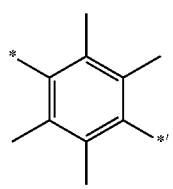
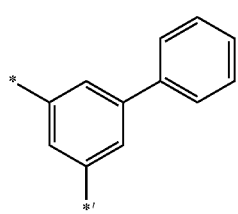
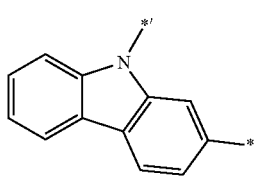
170
-continued
Formula 5-18
Formula 5-19
Formula 5-20
Formula 5-21
Formula 5-22
Formula 5-23
Formula 5-24
Formula 5-25
Formula 5-26
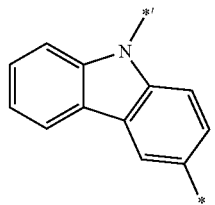
Formula 5-27
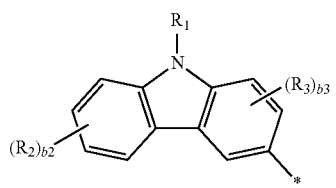
Formula 2-1
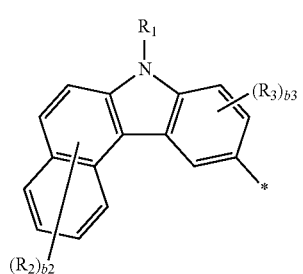
Formula 2-2
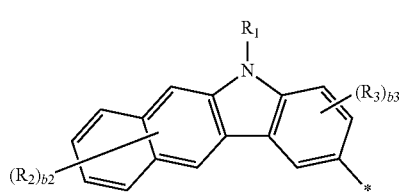
Formula 2-3
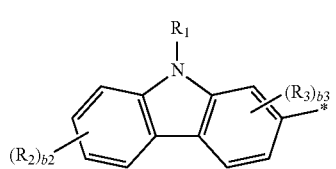
Formula 2-4
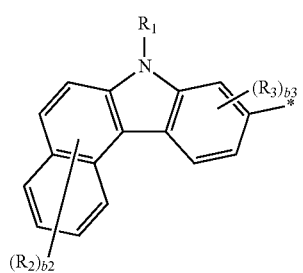
Formula 2-5
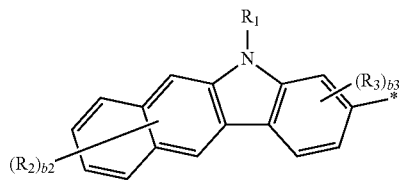
Formula 2-6

Formula 3A-1

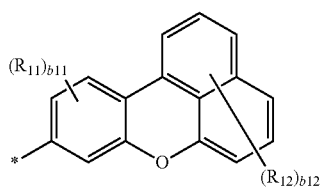

Formula 3B-1

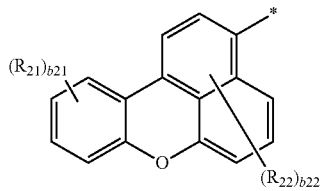

Formula 3A-2

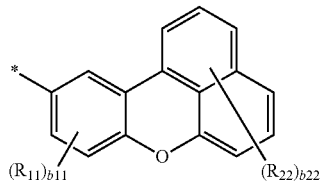

Formula 3B-2

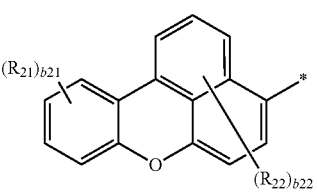

wherein, in Formulae 2-1 to 2-6, 3A-1, 3B-1, 3A-2, and 3B-2, $R_2$, $R_3$, $R_{11}$, $R_{12}$, $R_{21}$, and $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

b2, b3, b21, and b22 are each independently 1 or 2; and

* is a binding site with an adjacent atom.

16. The amine-based compound as claimed in claim 1, wherein the amine-based compound is one of Compounds 1 to 110:

1

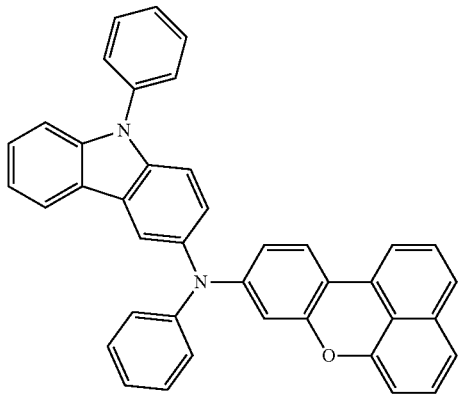

2

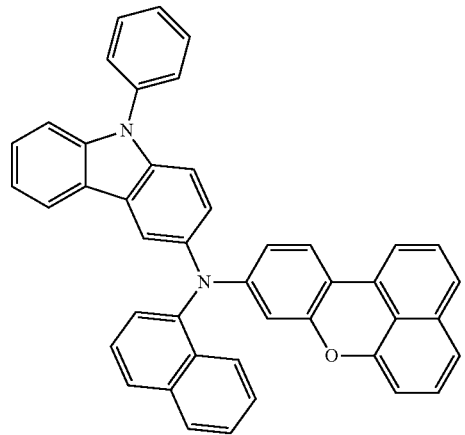

3

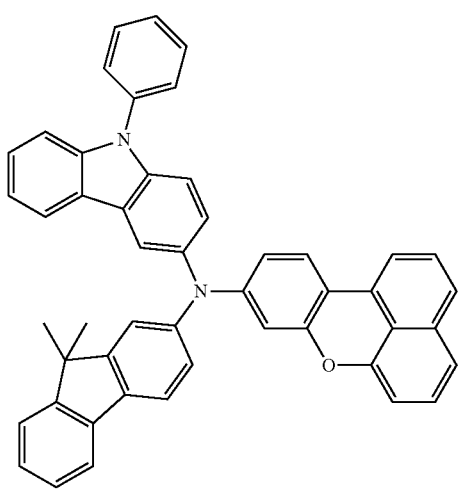

4

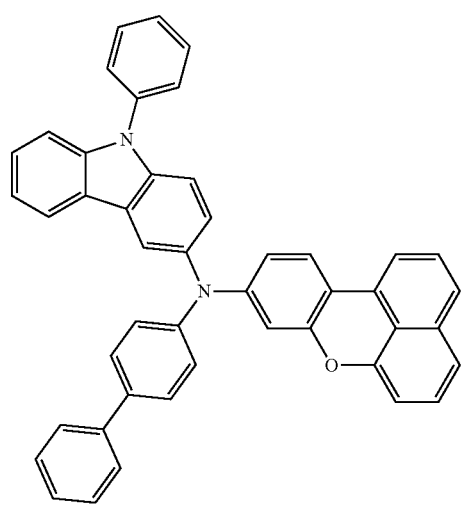

-continued
5
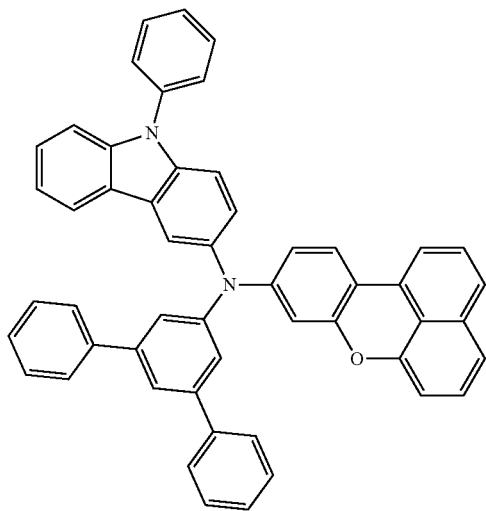
6
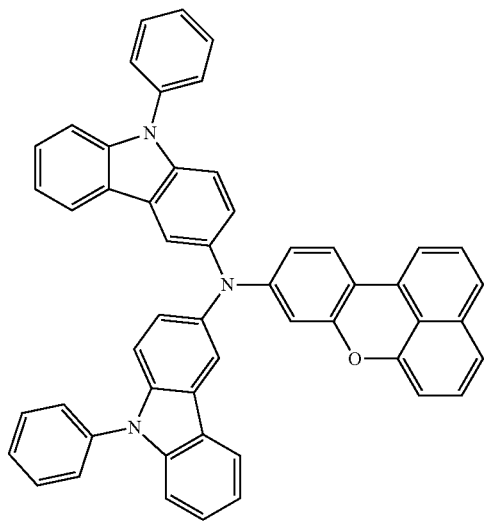
7
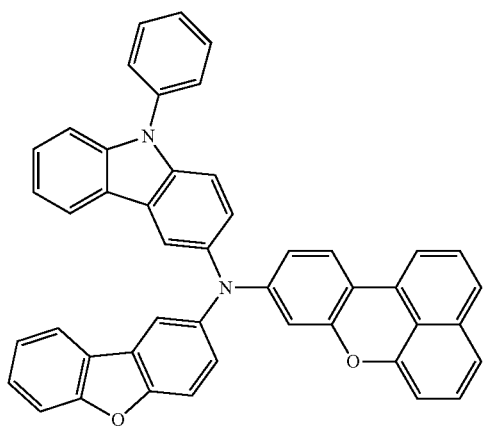
8
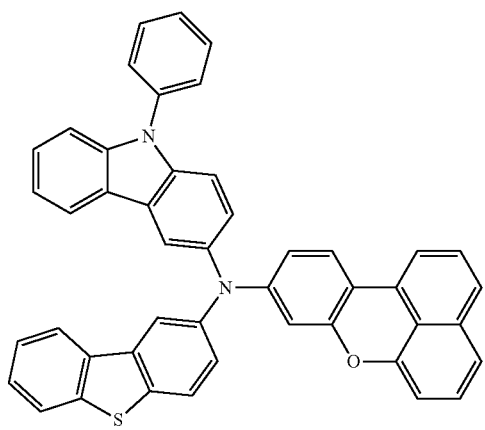
9
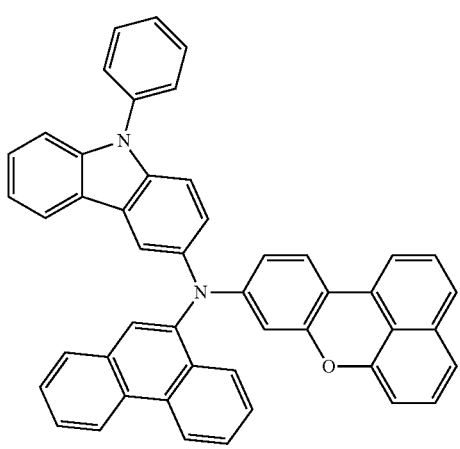
10
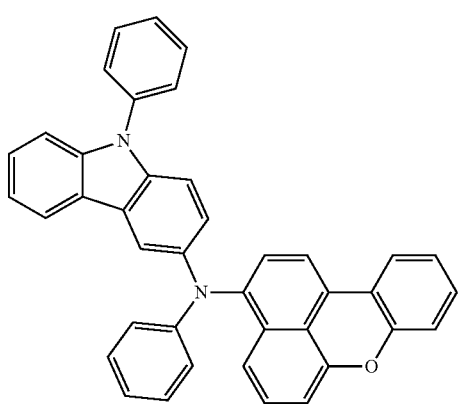

-continued
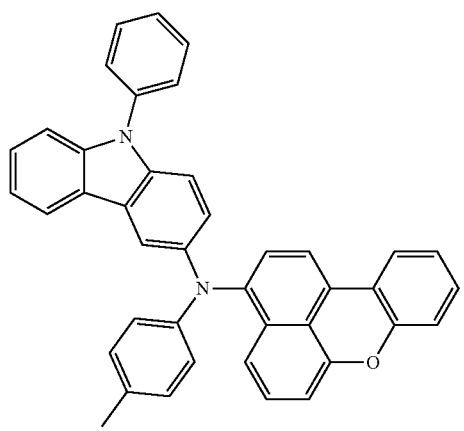
11
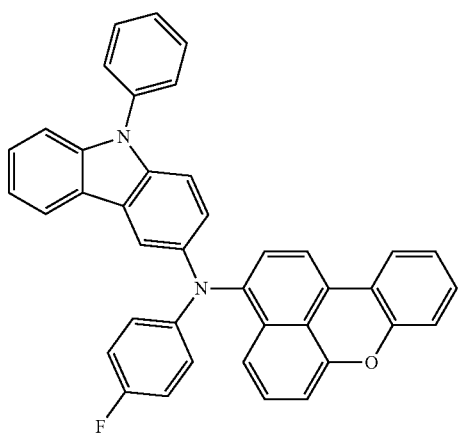
12
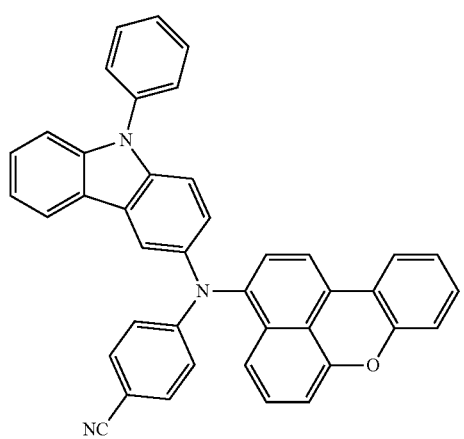
13
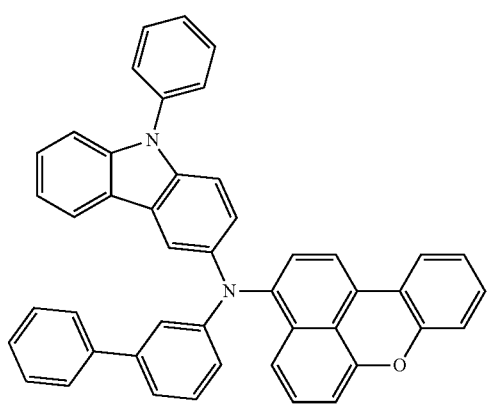
14
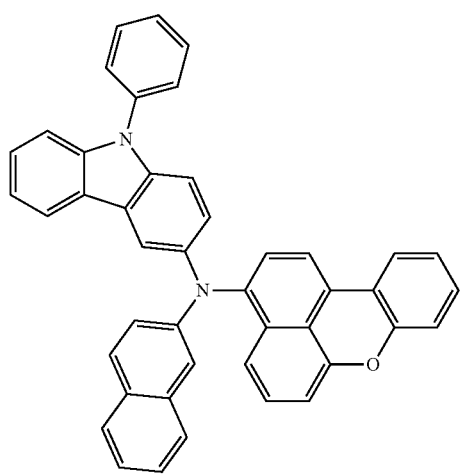
15
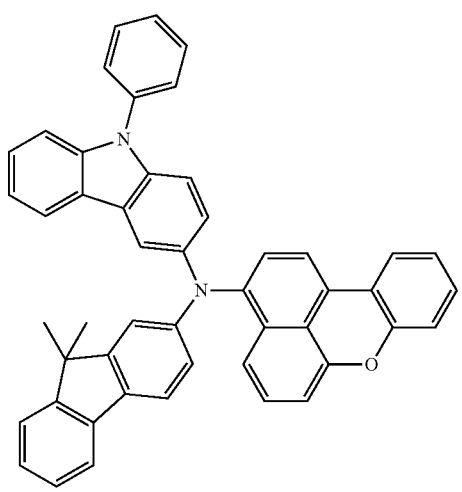
16

-continued
17
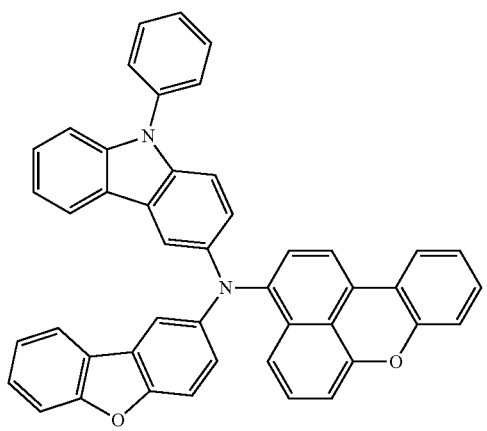
18
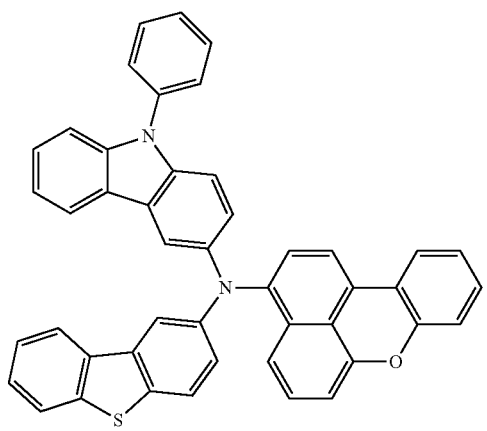
19
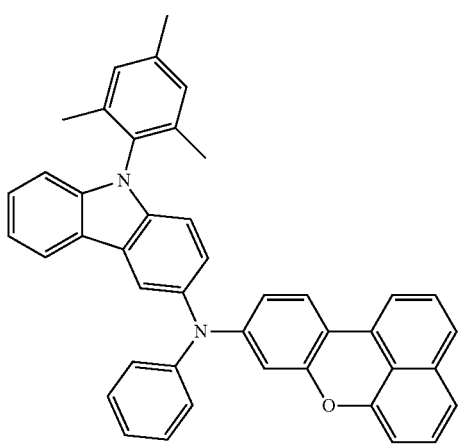
20
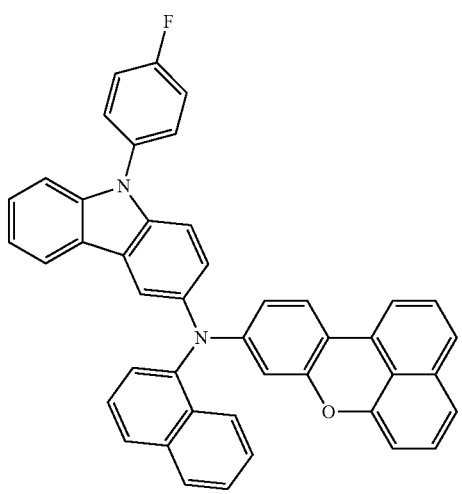
21
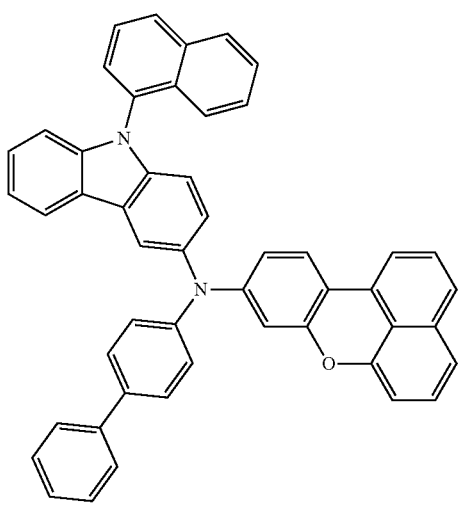
22
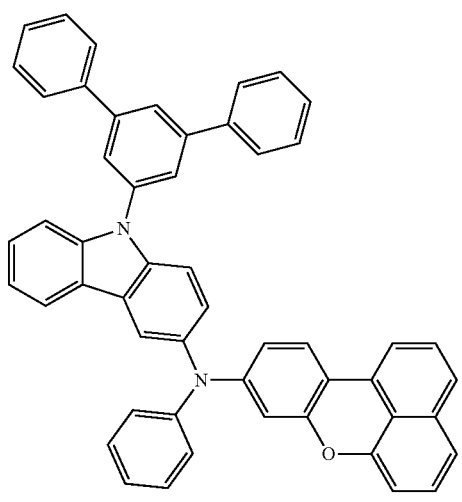

-continued
23
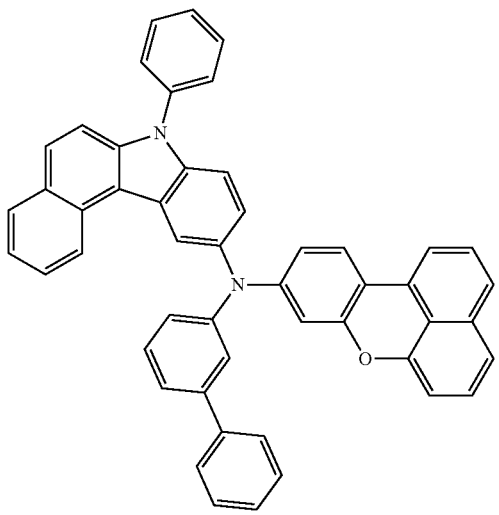
24
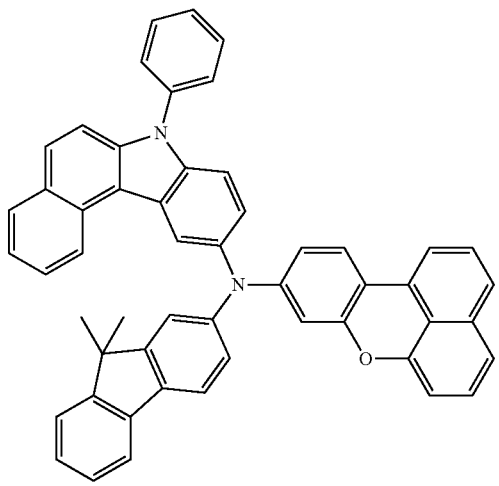
25
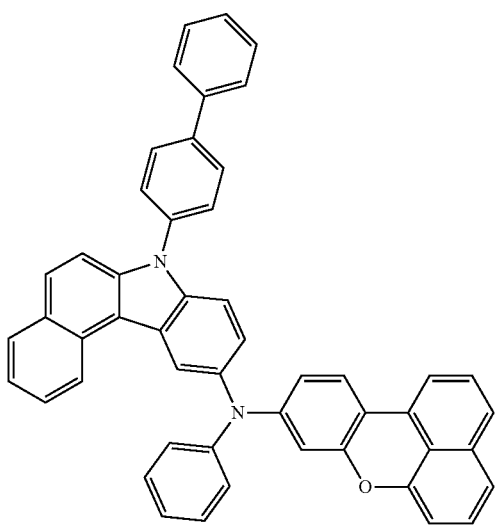
26
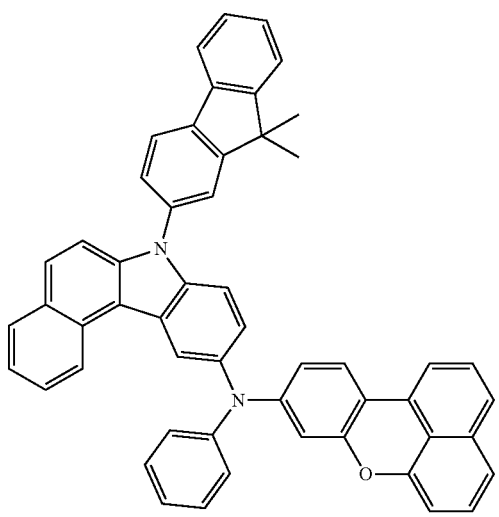
27
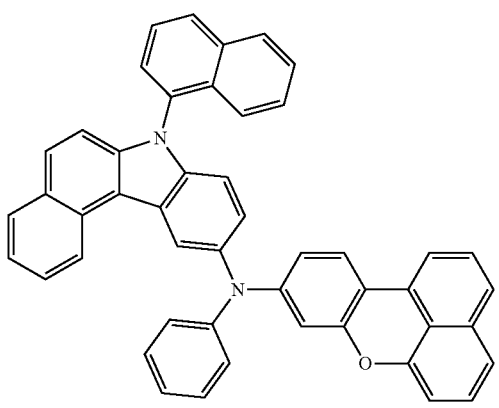
28
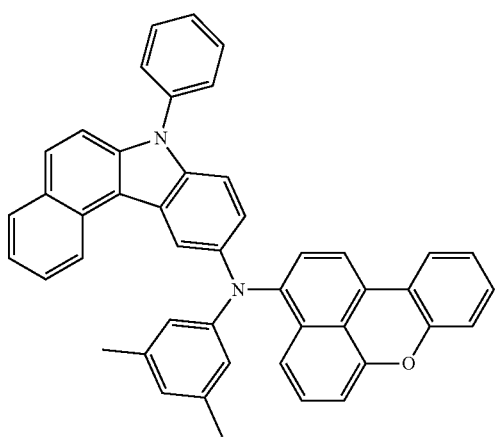

-continued
29
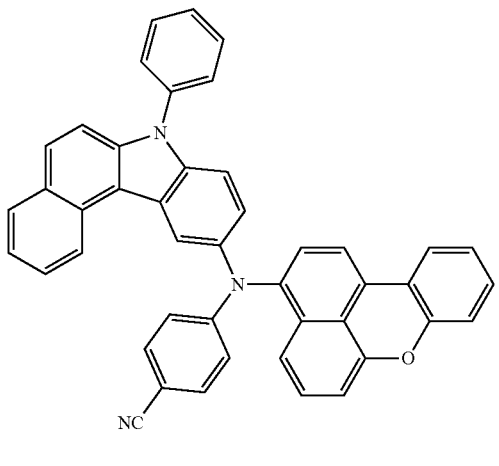
30
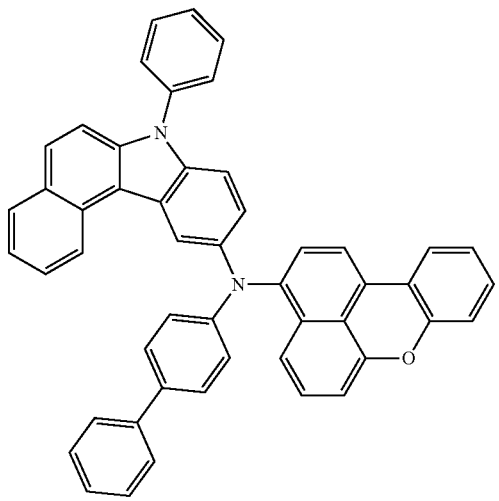
31
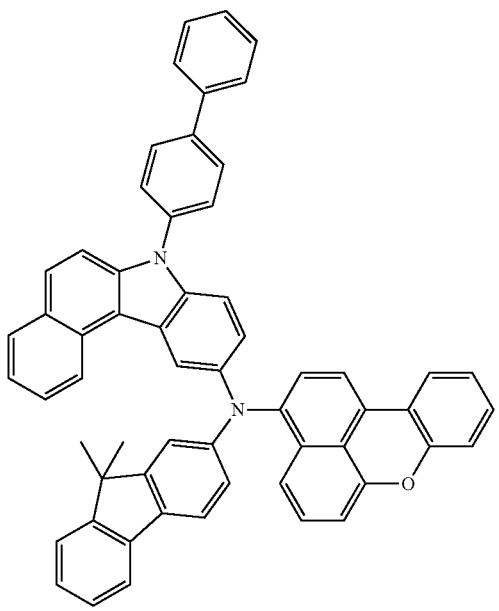
32
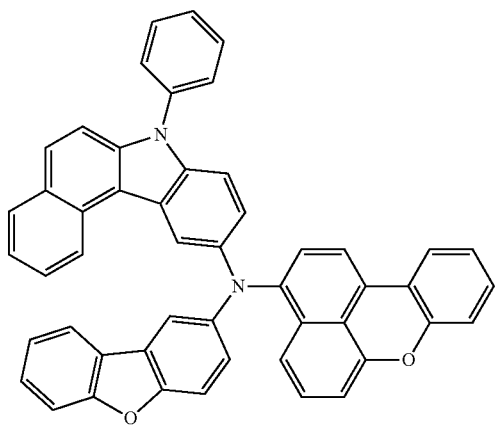
33
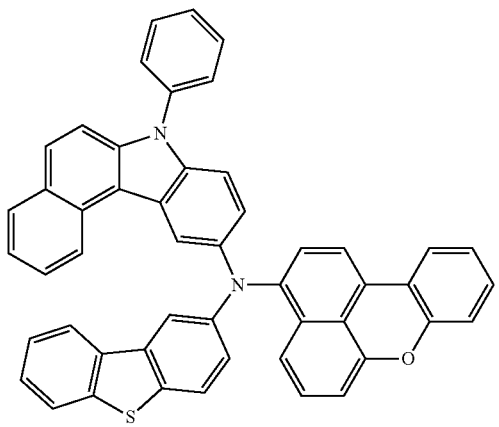
34
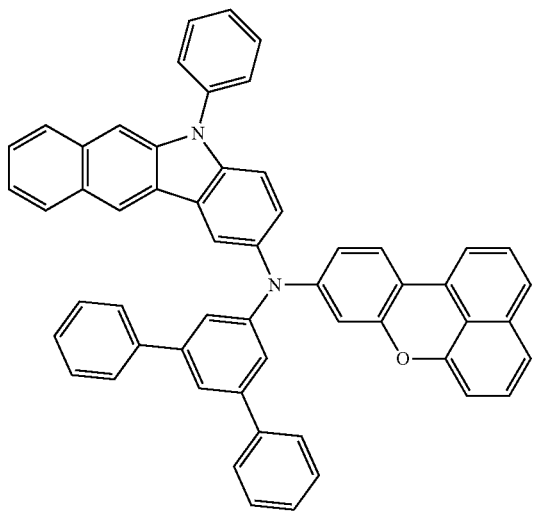

35
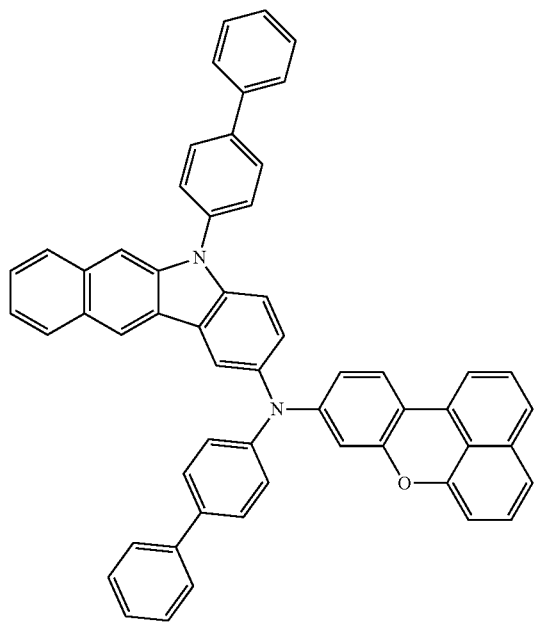
36
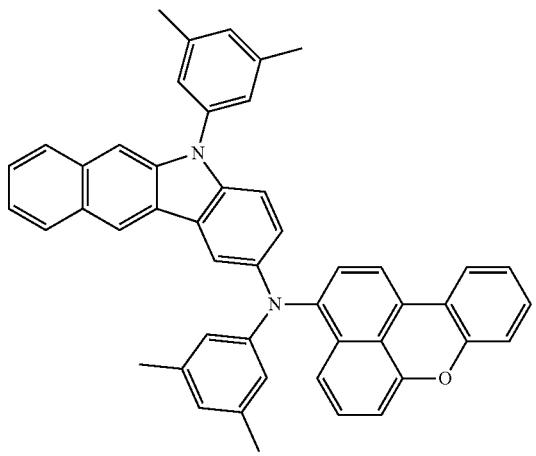
37
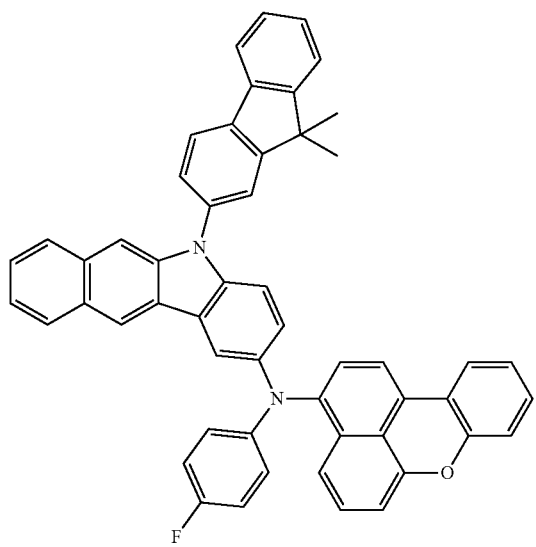
38
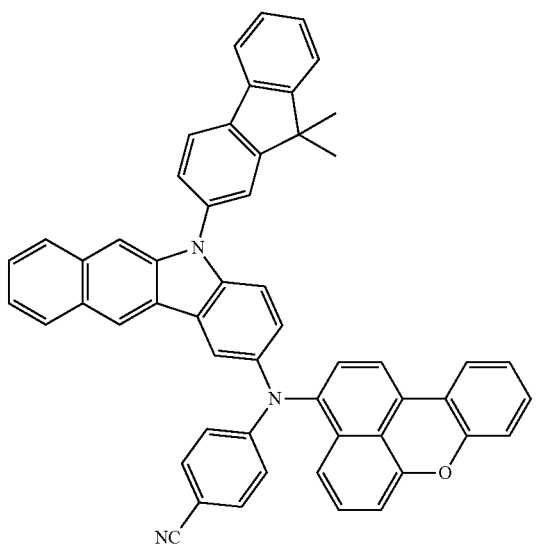
39
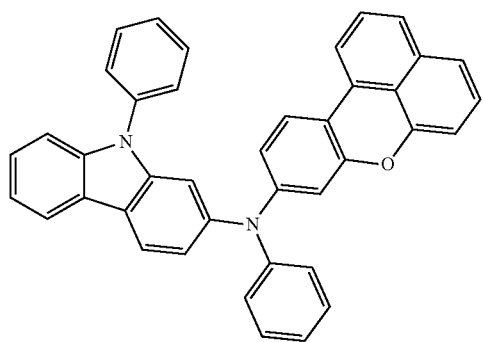
40
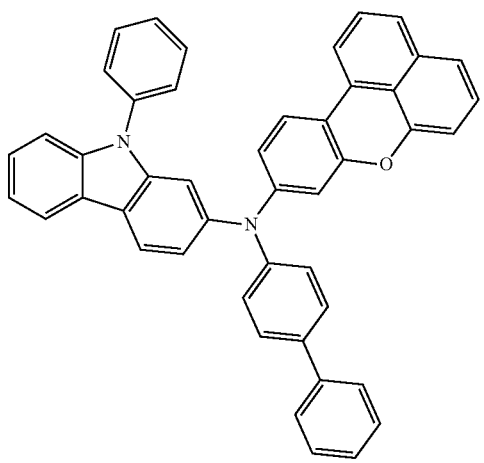

-continued
41
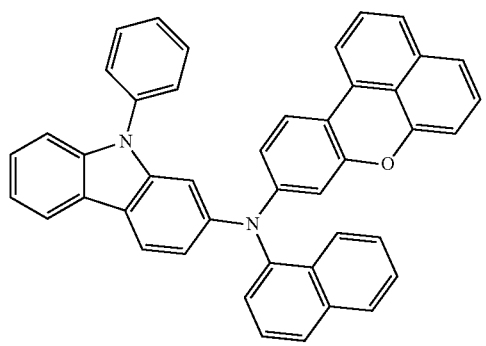
42
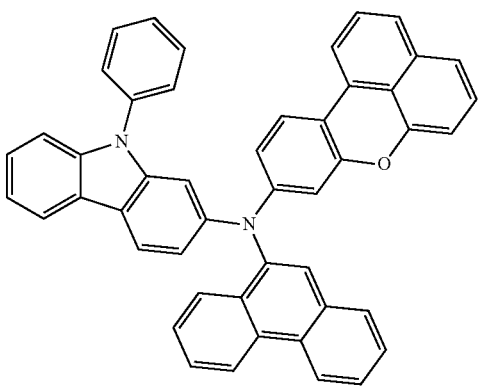
43
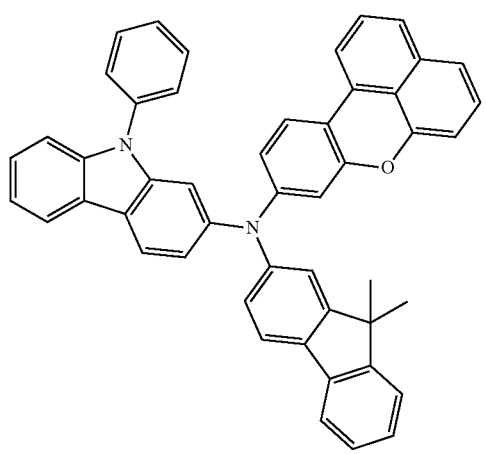
44
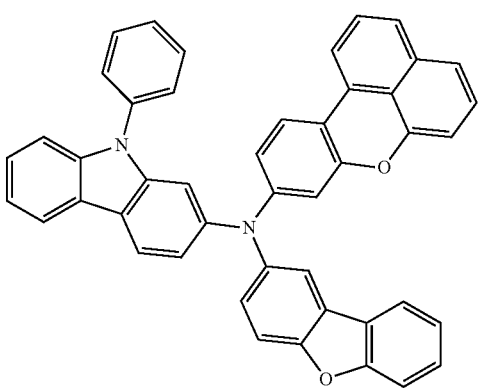
45
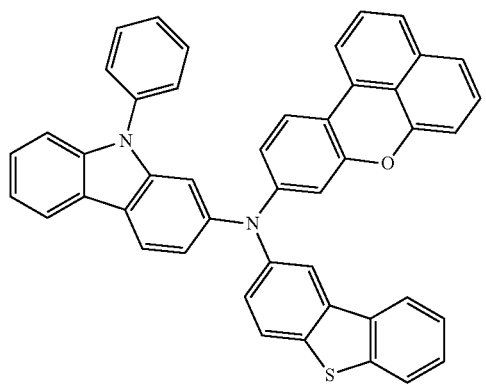
46
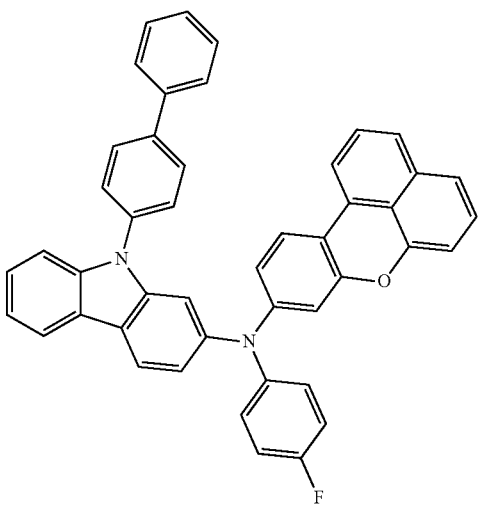

-continued
47
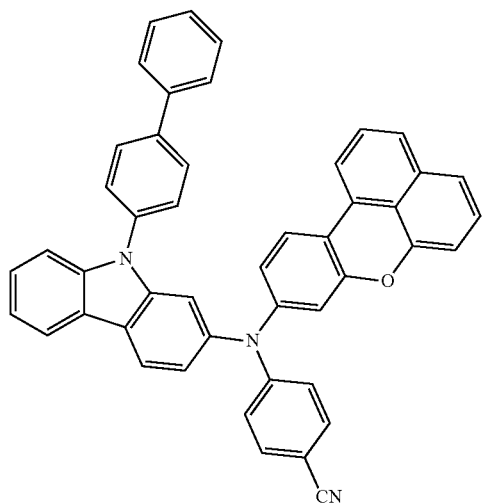
48
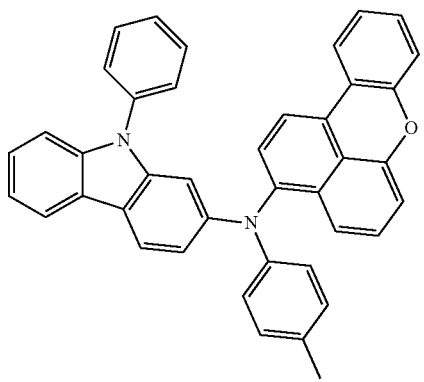
49
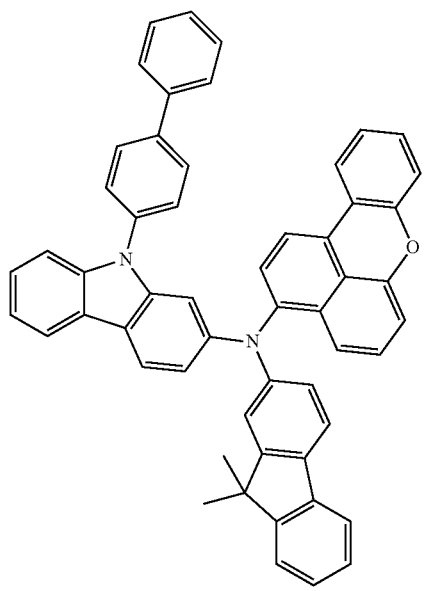
50
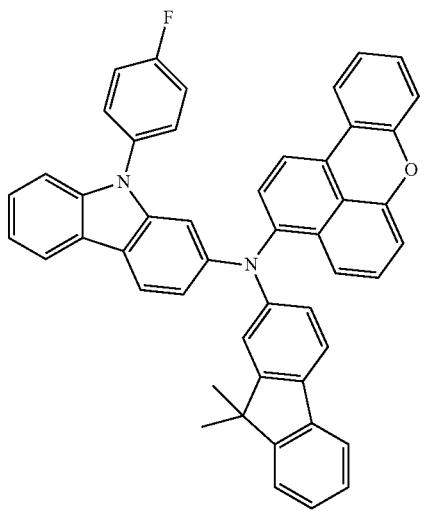
51
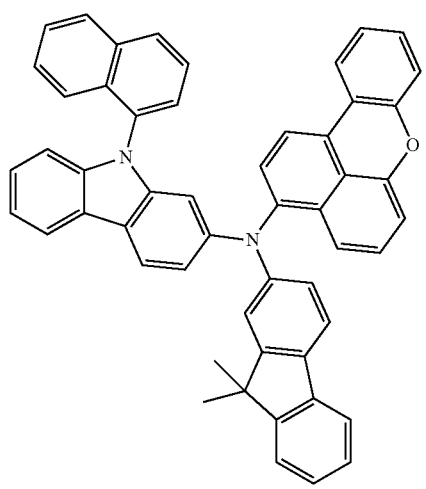
52
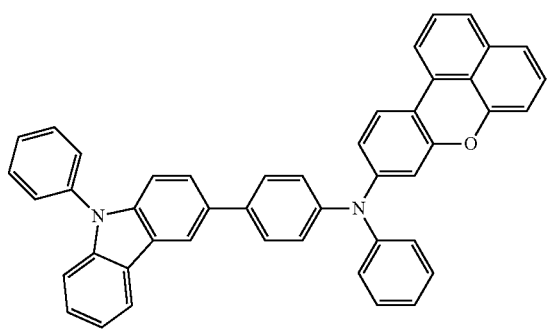

-continued
53
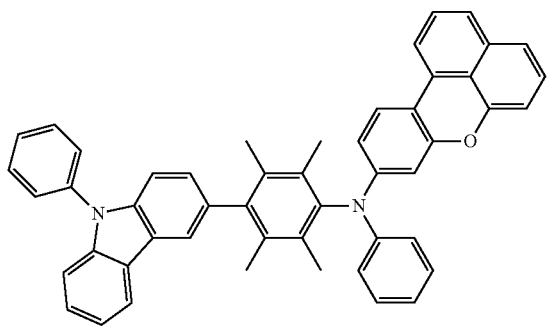
54
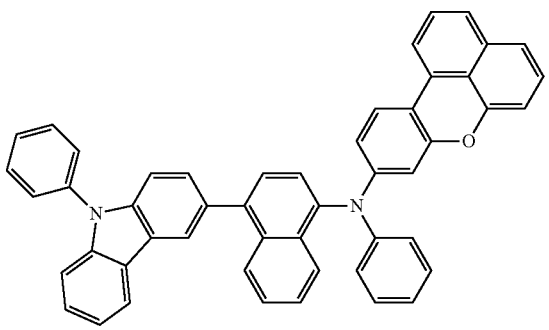
55
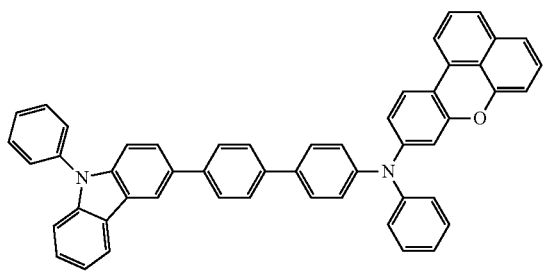
56
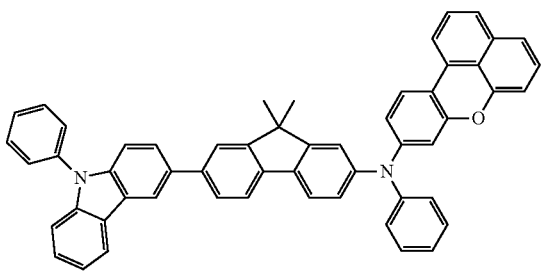
57
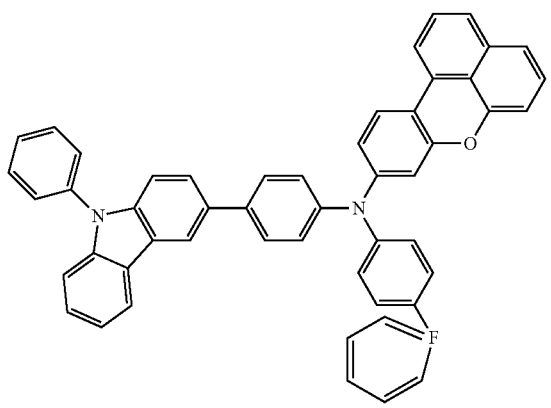
58
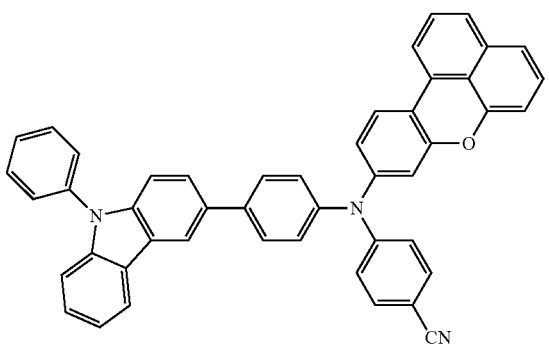
59
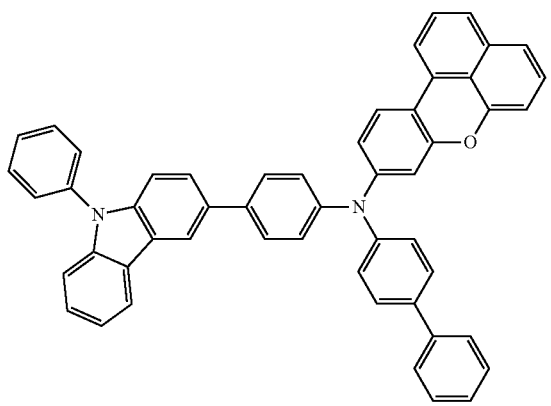
60
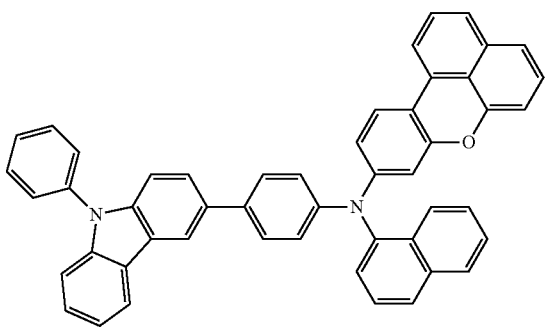

-continued
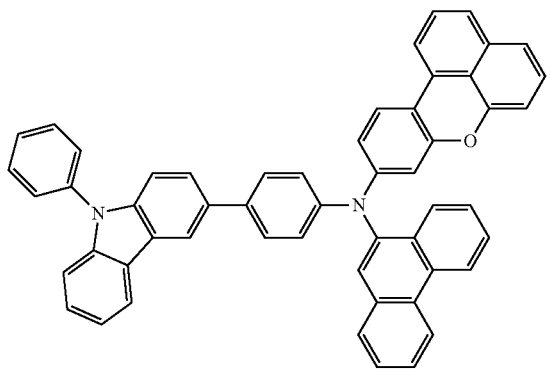
61
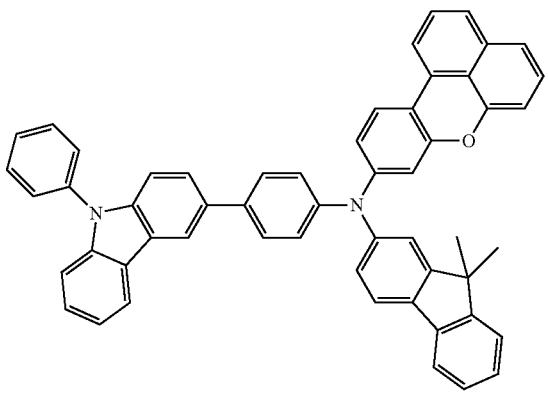
62
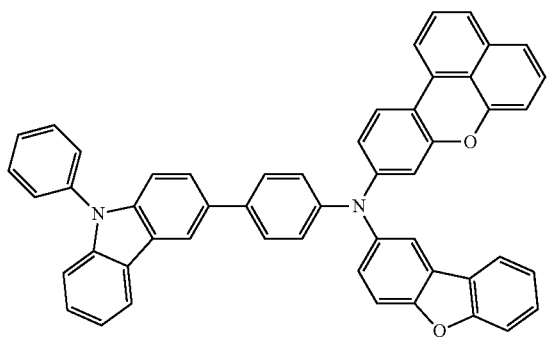
63
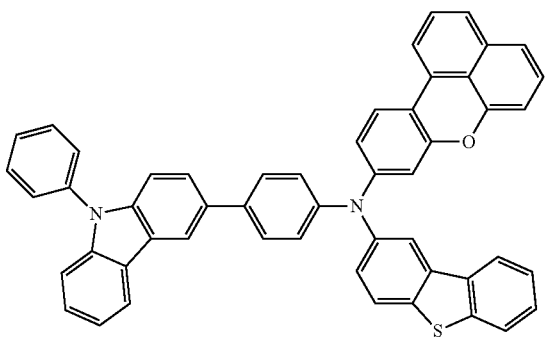
64
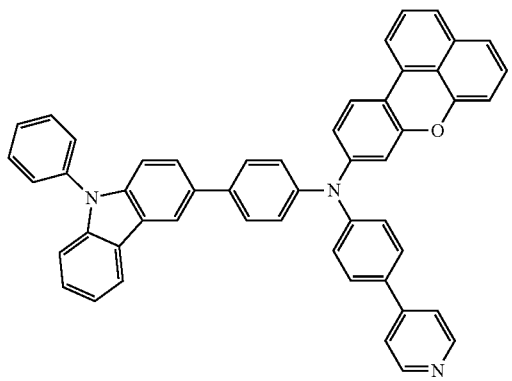
65
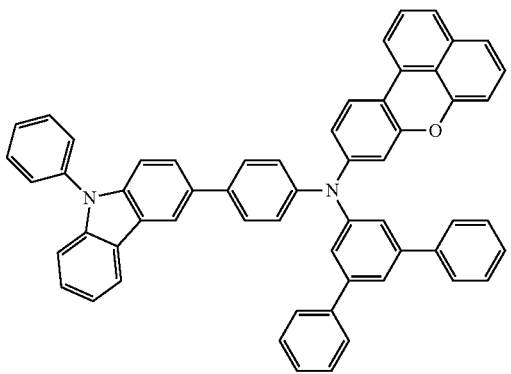
66
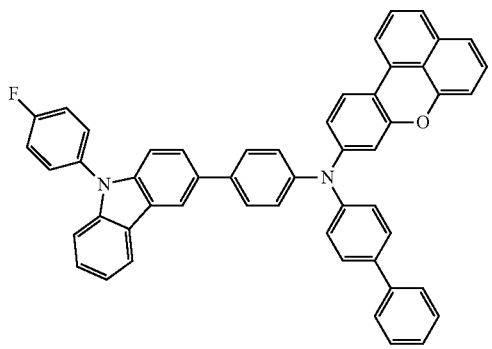
67
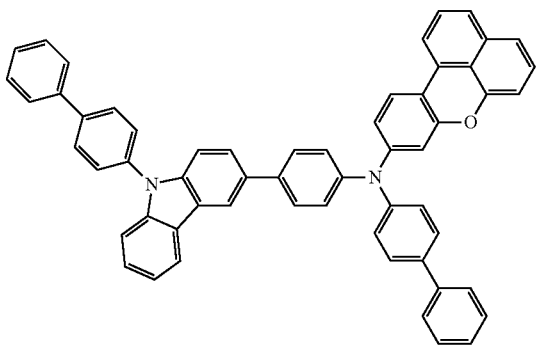
68

-continued
69
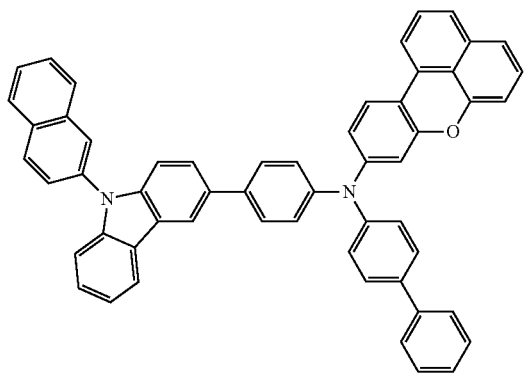
70
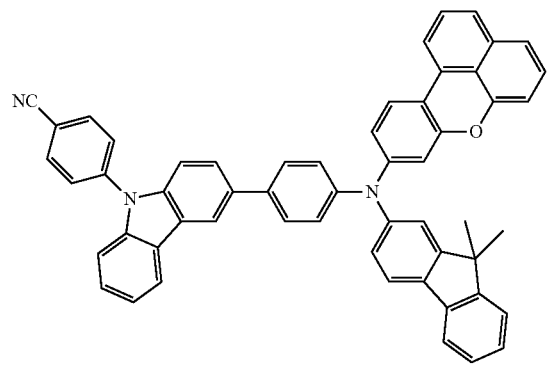
71
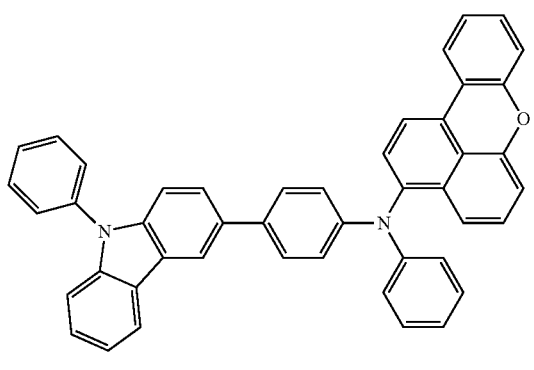
72
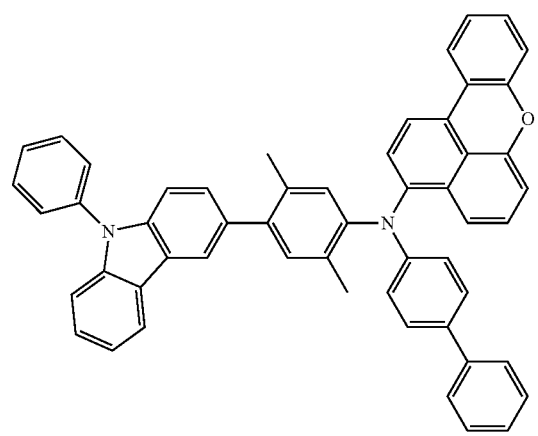
73
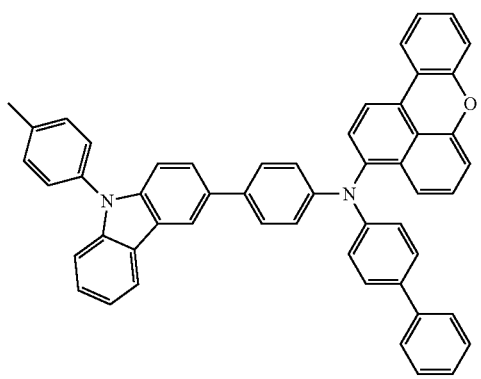
74
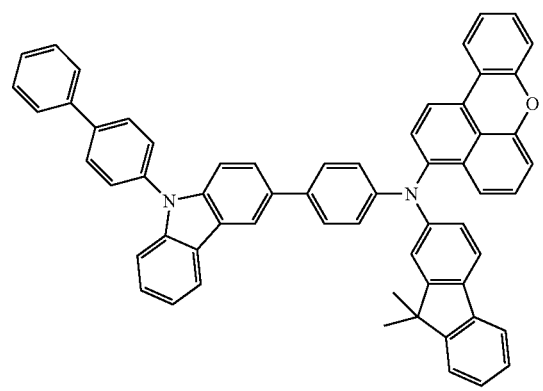

-continued
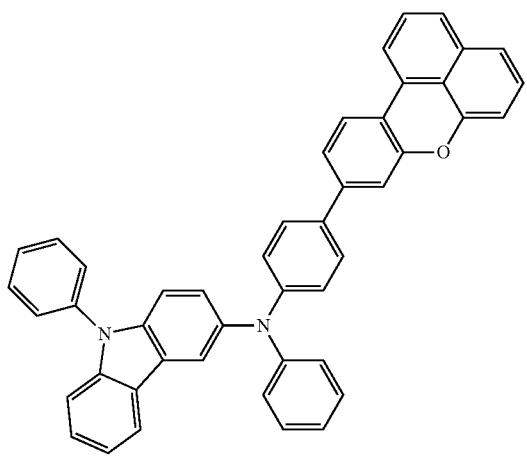
75
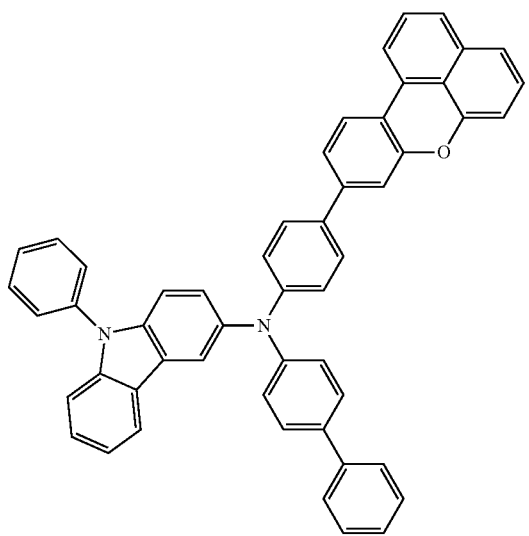
76
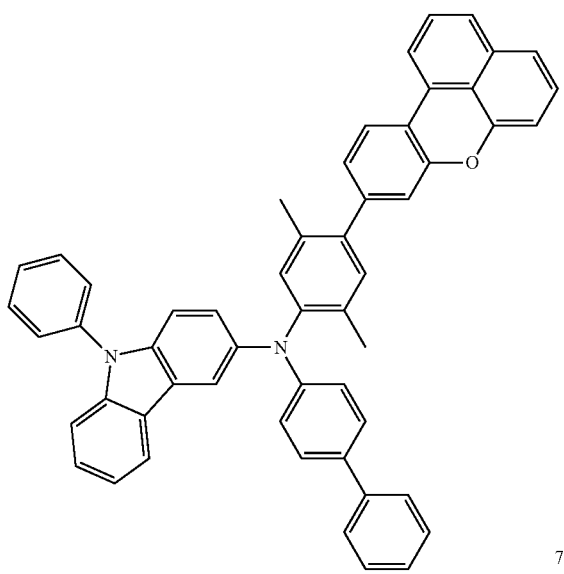
77
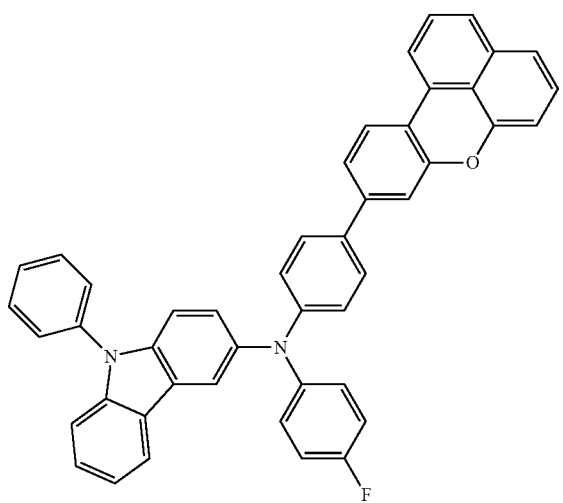
78
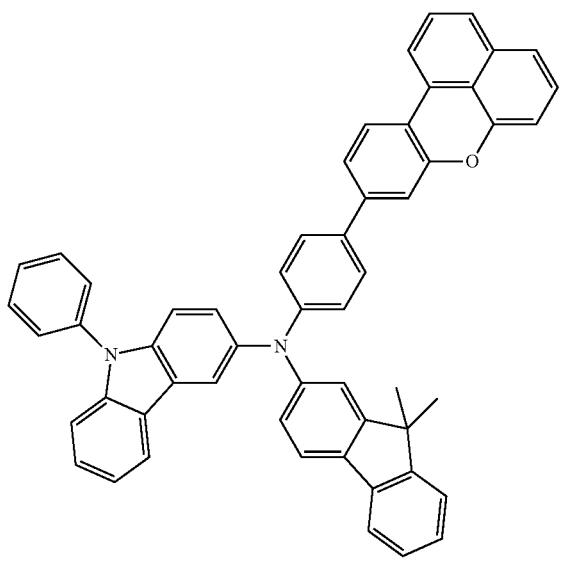
79
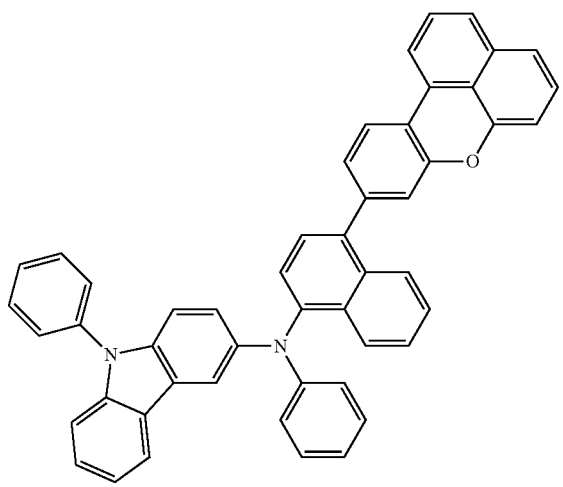
80

-continued
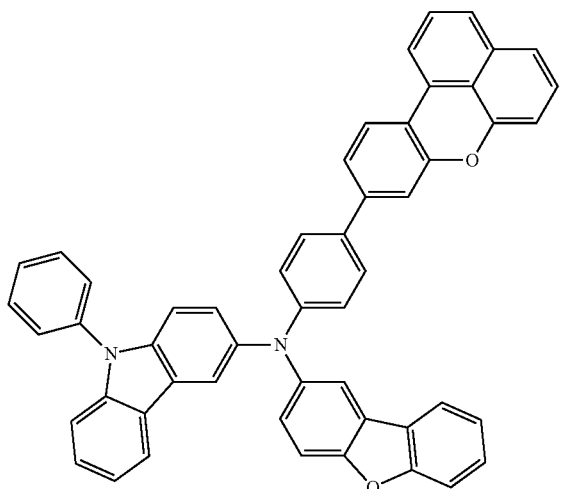
81
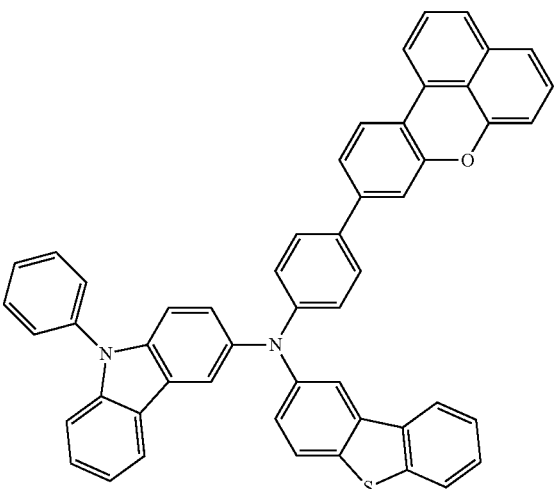
82
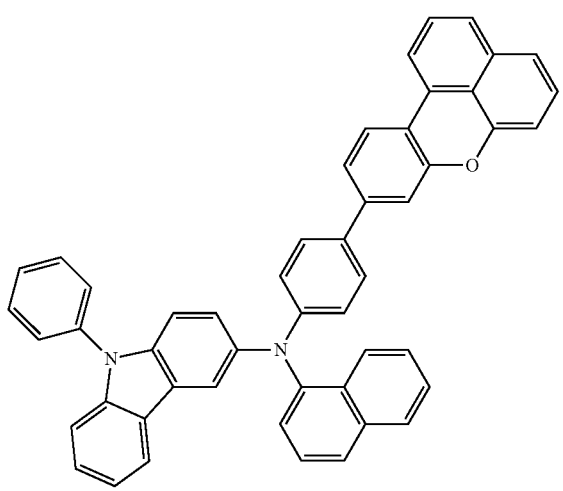
83
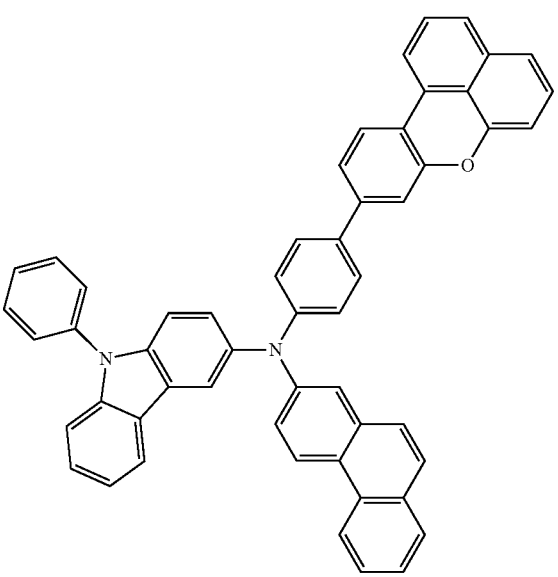
84
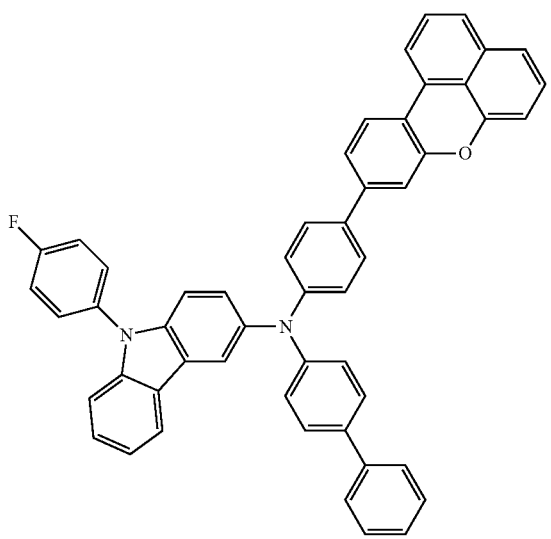
85
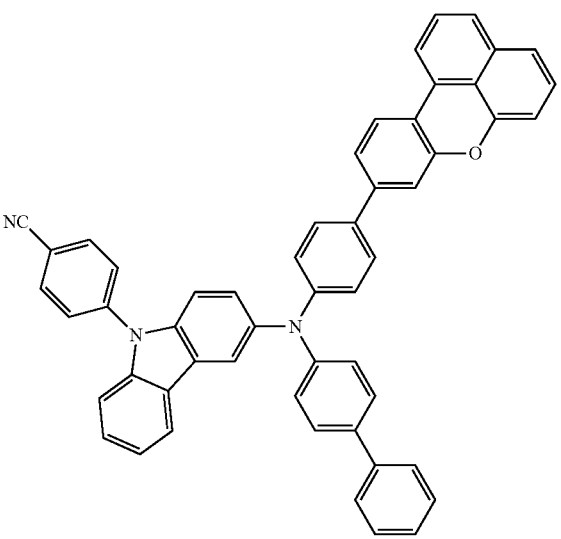
86

-continued
87
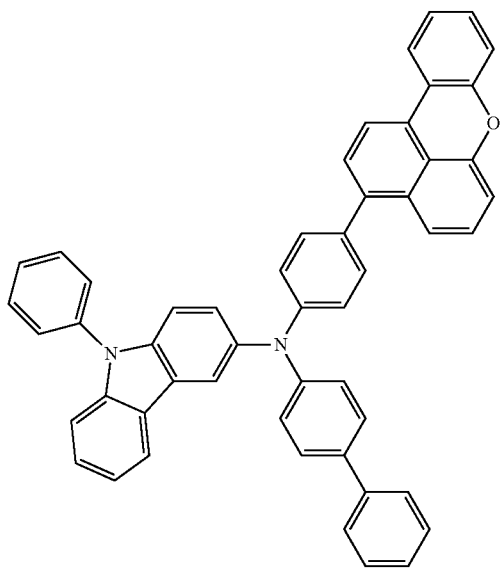
88
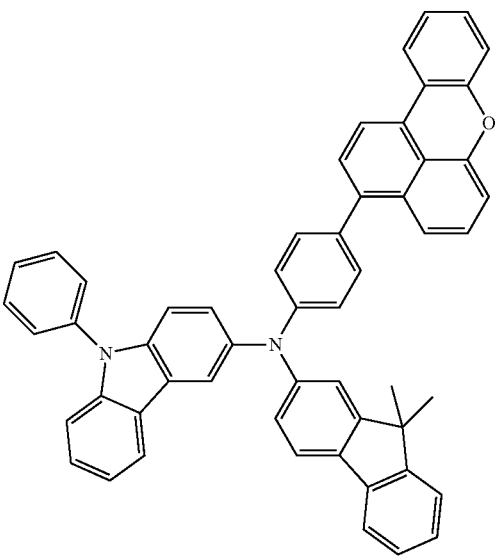
89
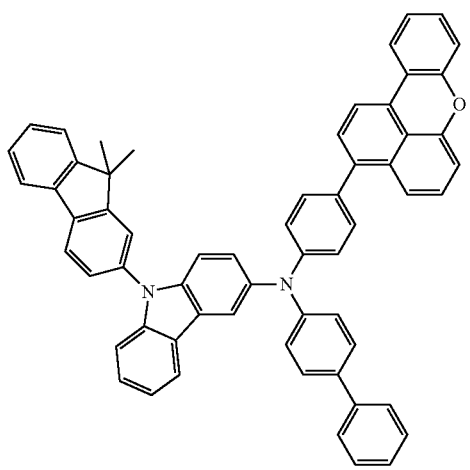
90
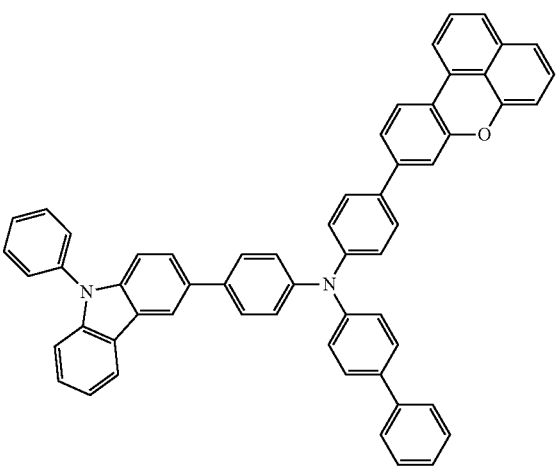
91
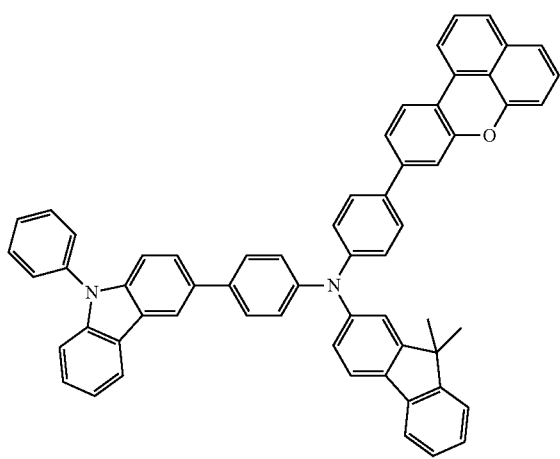
92
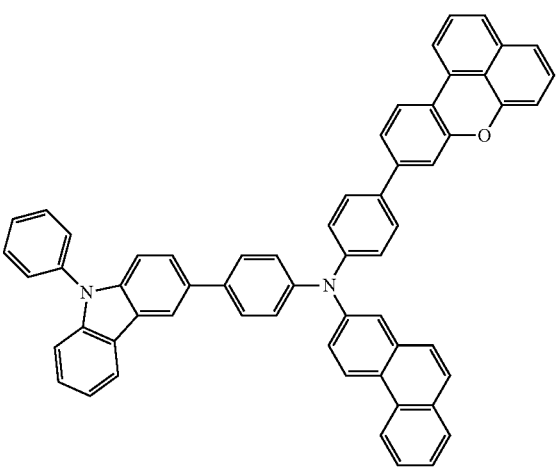

93
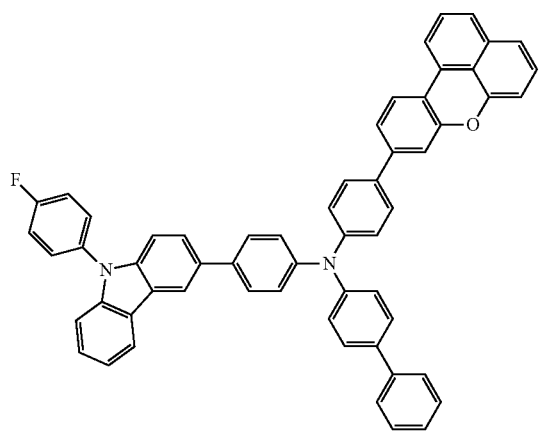
94
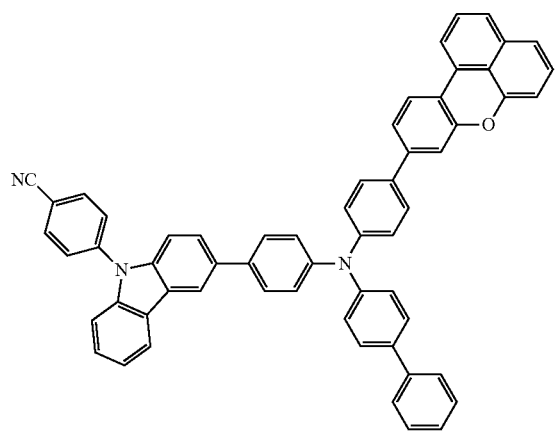
95
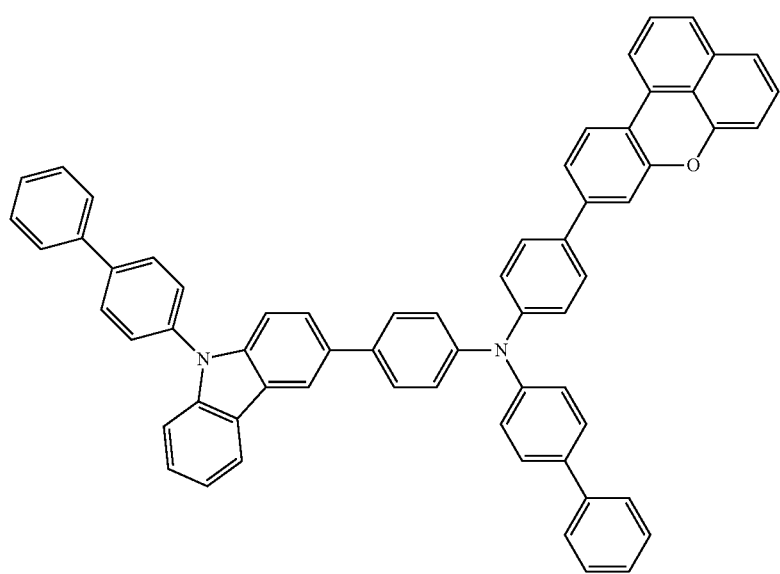
96
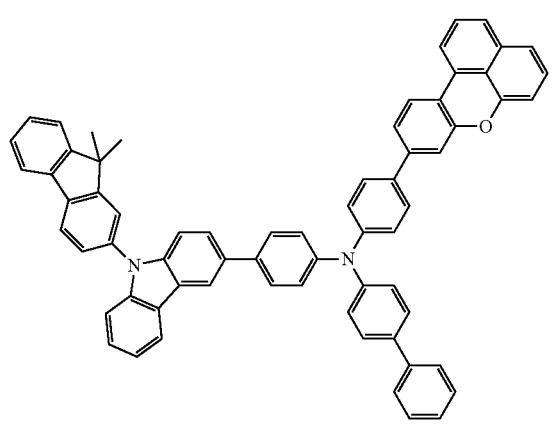
97
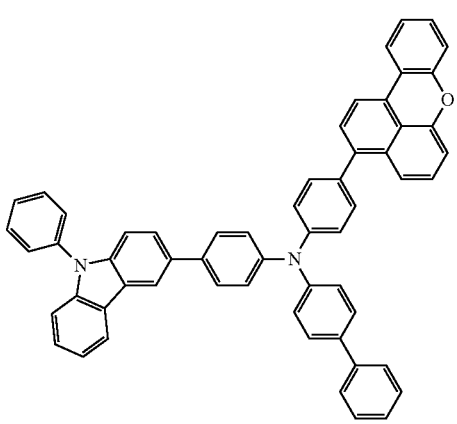

98
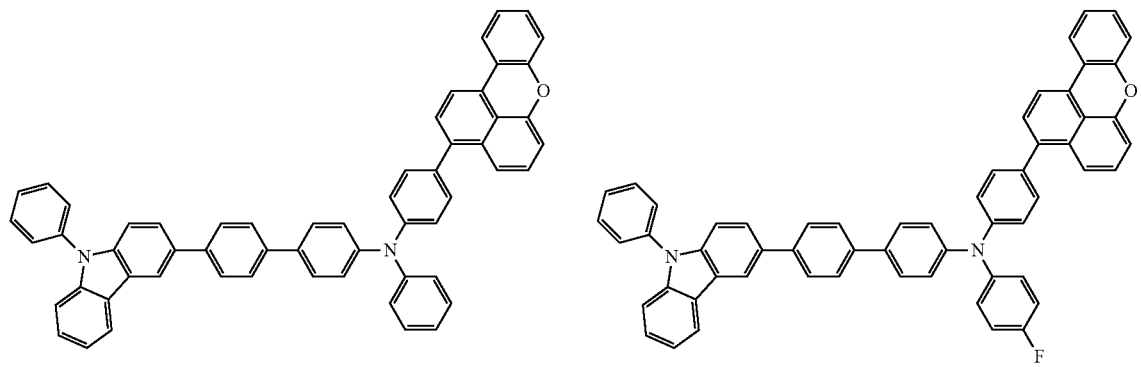
99
100
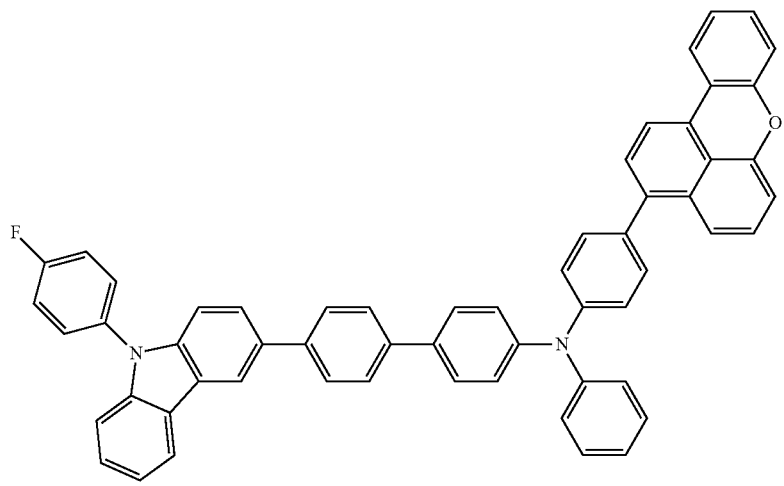
101
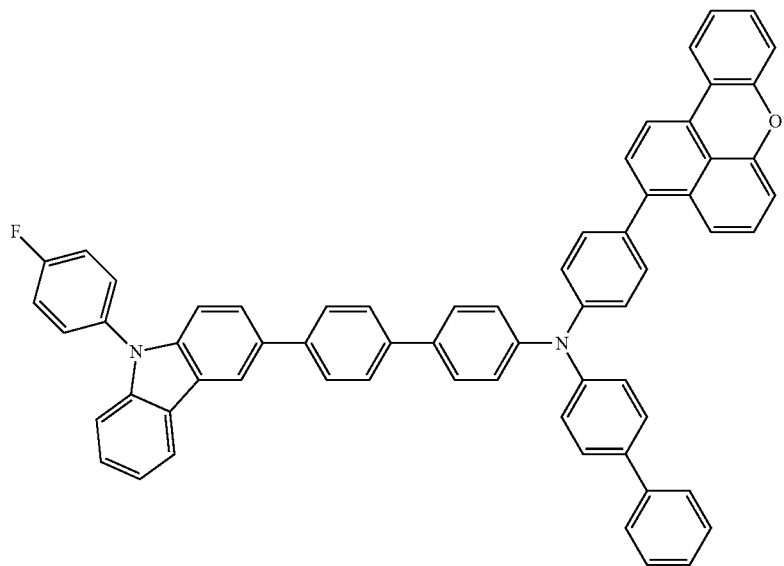

-continued
102
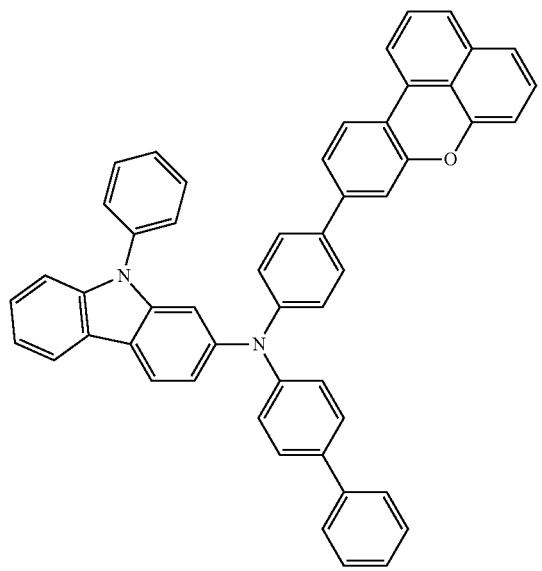
103
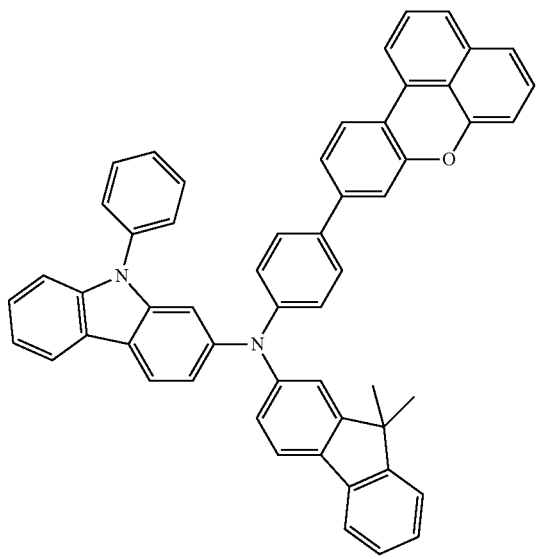
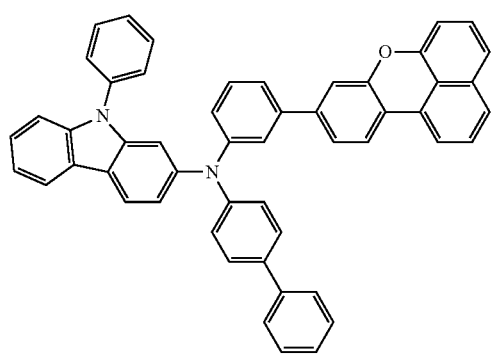
105
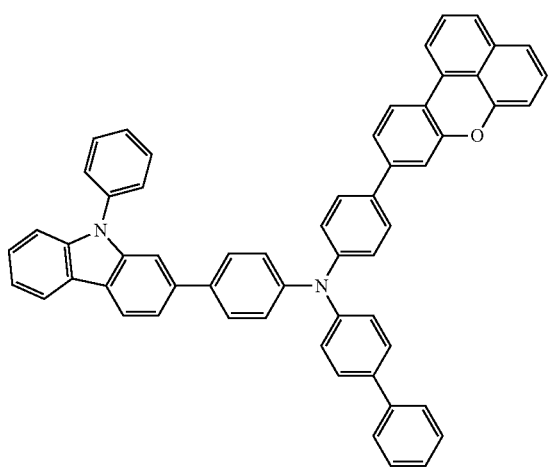
106
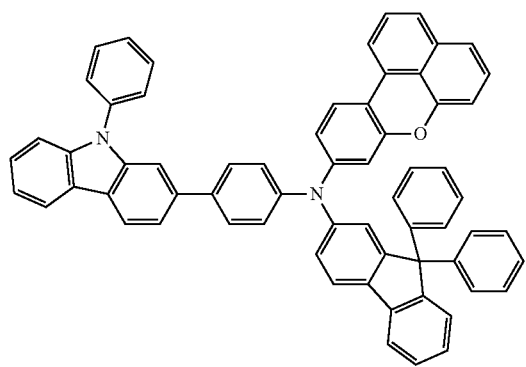
107
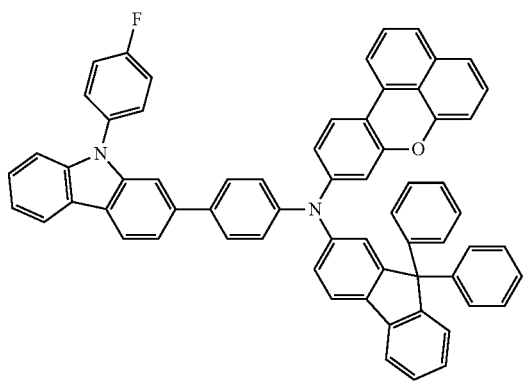

-continued

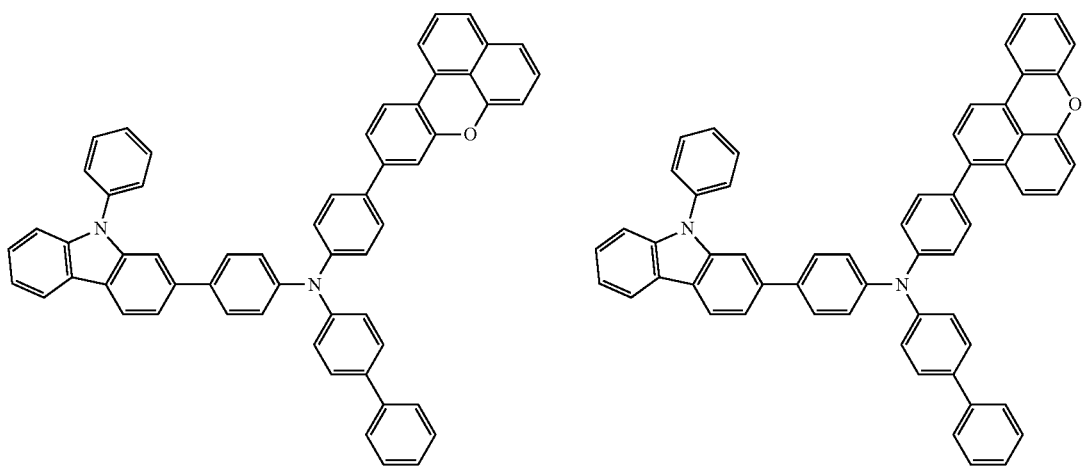

108

109

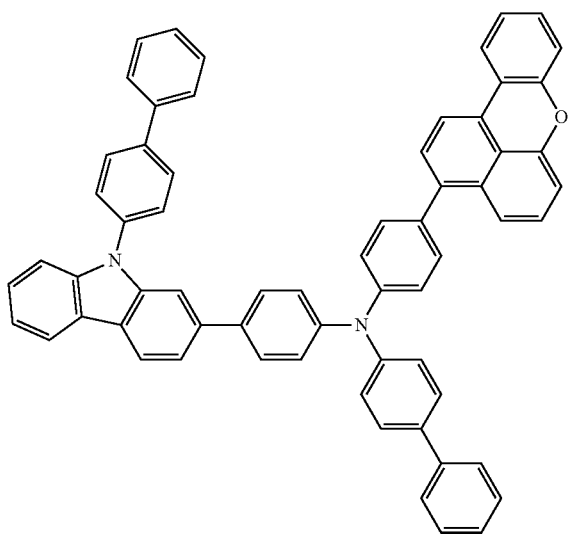

110

17. An organic light-emitting device, comprising:
a first electrode;
a second electrode opposite the first electrode; and
an organic layer between the first electrode and the second electrode, the organic layer including an emission layer, and the organic layer including at least one amine-based compound represented by Formula 1 as claimed in claim 1.

18. The organic light-emitting device as claimed in claim 17, wherein the first electrode is an anode, the second electrode is a cathode, and the organic layer includes i) a hole transport region between the first electrode and the emission layer, the hole transport layer including at least one of a hole injection layer, a hole transport layer, a buffer layer, and an electron blocking layer, and ii) an electron transport region between the emission layer and the second electrode, the electron transport layer including at least one of a hole blocking layer, an electron transport layer, and an electron injection layer, wherein the at least one amine-based compound represented by Formula 1 is in the hole transport region.

19. The organic light-emitting device as claimed in claim 18, wherein:
the hole transport region includes a hole transport layer, and
the hole transport layer includes the at least one amine-based compound represented by Formula 1.

20. The organic light-emitting device as claimed in claim 17, further comprising at least one of a first capping layer and a second capping layer, the first capping layer being disposed on an optical path along which light generated in the emission layer passes outwards through the first electrode, and the second capping layer being disposed on an optical path along which the light generated in the emission layer passes outwards through the second electrode, wherein at least one of the first and second capping layers includes the at least one amine-based compound represented by Formula 1.

* * * * *